US012734251B2

(12) United States Patent
Shi et al.

(10) Patent No.: US 12,734,251 B2
(45) Date of Patent: Sep. 15, 2026

(54) COMPOSITIONS AND METHODS FOR THE TREATMENT OF EYE DISEASES

(71) Applicant: FTGEN Corp, Watertown, MA (US)

(72) Inventors: Zhongdong Shi, Bedford, MA (US); Wei Zhao, Boston, MA (US)

(73) Assignee: FTGEN Corp, Watertown, MA (US)

( * ) Notice: Subject to any disclaimer, the term of this patent is extended or adjusted under 35 U.S.C. 154(b) by 650 days.

(21) Appl. No.: 18/157,589

(22) Filed: Jan. 20, 2023

(65) Prior Publication Data

US 2023/0321281 A1 Oct. 12, 2023

Related U.S. Application Data

(63) Continuation of application No. PCT/IB2021/000509, filed on Jul. 20, 2021.

(30) Foreign Application Priority Data

Jul. 21, 2020 (CN) ........................ 202010705069.X

(51) Int. Cl.
*A61K 48/00* (2006.01)
*A61K 38/17* (2006.01)
*A61P 27/02* (2006.01)

(52) U.S. Cl.
CPC ...... *A61K 48/0058* (2013.01); *A61K 38/1709* (2013.01); *A61P 27/02* (2018.01)

(58) Field of Classification Search
CPC .......... A61K 48/0058; C12N 2830/008; C12N 2750/14143
See application file for complete search history.

(56) References Cited

U.S. PATENT DOCUMENTS 9,534,225 B2 * 1/2017 Ye ........................... A61P 43/00
2016/0346359 A1 * 12/2016 Buchlis ................... A61P 27/02
2018/0036385 A1 2/2018 Beltran et al.
2018/0273594 A1 * 9/2018 Maclaren ............. A61K 48/005
2020/0360534 A1 * 11/2020 Rodino-Klapac ........................... C07K 14/4707

FOREIGN PATENT DOCUMENTS

CA 2995656 A1 3/2017
CN 110461368 A 11/2019
EP 4185319 A1 5/2023
JP 2015523379 A 8/2015
JP 2017513484 A 6/2017
WO WO-2014045674 A1 3/2014
WO WO-2015160893 A1 10/2015
WO WO-2015168666 A2 11/2015
WO WO-2017042584 A1 * 3/2017 ............. A61P 43/00
WO WO-2018022905 A2 2/2018
WO WO-2019006182 A1 1/2019
WO WO-2020061574 A1 3/2020
WO WO-2021142447 A1 7/2021
WO WO-2022018518 A1 1/2022

OTHER PUBLICATIONS

Young,J.E.,et al (A short, highly active photoreceptor-specific enhancer/promoter region upstream of the human rhodopsin kinase gene, J, Invest. Opthamol. Vis. Sci. 44 (9), 4076-4085 (2003)) (Year: 2003).*

Dufour; Valérie L. et al.: Toxicity and Efficacy Evaluation of an Adeno-Associated Virus Vector Expressing Codon-Optimized RPGR Delivered by Subretinal Injection in a Canine Model of X-linked Retinitis Pigmentosa. Human Gene Therapy 31(3-4):253-267 (2020). doi: 10.1089/hum.2019.297.

Deng et al. Stability and Safety of an AAV Vector for Treating RPGR-ORF15 X-Linked Retinitis Pigmentosa. Human Gene Therapy 26(9):593-602 (2015).

Giacalone et al. Development of a Molecularly Stable Gene Therapy Vector for the Treatment of RPGR-Associated X-Linked Retinitis Pigmentosa. Human Gene Therapy 30(8):967-974 (2019).

Ou et al. Research progress in the treatment of retinitis pigmentosa. International Eye Science 18(9):1608-1611 (2018) (English Abstract).

PCT/IB2021/000509 International Search Report and Written Opinion dated Dec. 8, 2021.

Smith et al.: Production of human beta interferon in insect cells infected with a baculovirus expression vector. Mol Cell Biol. 3(12):2156-2165 (1983).

Cevec: ASGCT 23rd Annual Meeting, Boston 1-14 (MA), USA—Virtual Format May 12, 2020: Abstract 454. Development of a Stable Helper Virus Free Producer Cell Line for Scalable Adeno Associated Virus Vectors Production Based on Human Suspension Cells (p. 201).

EP21845856.0 Extended European Search Report dated Nov. 4, 2024.

De La Camara, Cristina Martinez-Fernandez et al.: RPGR gene therapy presents challenges in cloning the coding sequence. Expert Opinion on Biological Therapy 20(1):1-17 (2020). https://doi.org/10.1080/14712598.2020.1680635.

(Continued)

*Primary Examiner* — Jane J Zara

(74) *Attorney, Agent, or Firm* — Wilson Sonsini Goodrich & Rosati

(57) ABSTRACT

Provided herein are compositions for treating or preventing Retinitis Pigmentosa. The compositions comprise a first polynucleotide and a second polynucleotide. The compositions may further comprise a third sequence and a fourth sequence. Also provided herein are the recombinant adeno-associated virus particles, systems, methods, and kits for practicing or using the same.

13 Claims, 3 Drawing Sheets

Specification includes a Sequence Listing.

(56) References Cited

OTHER PUBLICATIONS

Smith, Jacob M. et al.: Overcoming Bottlenecks in AAV Manufacturing for Gene Therapy. Cell & Gene Therapy, pp. 815-827 (2018). DOI: 10.18609/cgti.2018.083.
Third Party Observation dated Aug. 7, 2025 issued in European Patent Application No. 2185856.0.
Kurasawa, James H. et al.: Chemically Defined, High-Density Insect Cell-Based Expression System for Scalable AAV Vector Production. Molecular Therapy—Methods & Development 19:330-340 (2020).

* cited by examiner

COMPOSITIONS AND METHODS FOR THE TREATMENT OF EYE DISEASES

CROSS REFERENCE

This application is a continuation of International Application No. PCT/IB2021/000509, filed Jul. 20, 2021, which claims the benefit of Chinese Disclosure Patent Application No. 202010705069.X, filed on Jul. 21, 2020, which is hereby incorporated by reference in its entirety.

BACKGROUND

Retinitis Pigmentosa (RP) is a hereditary eye disease that can lead to vision loss, with symptoms including difficulties in night vision and loss in peripheral vision (side view). Although usually appearing in childhood, the symptoms gradually worsen. X-linked retinitis pigmentosa (XLRP) is a type of RP caused by mutations in retinitis pigmentosa GTPase regulators (RPGR) located on the X chromosome. The disease patient begins with night blindness, then gradual reduction of the vision, and eventually complete blindness.

SEQUENCE LISTING

The instant application contains a Sequence Listing which has been submitted electronically in XML format and is hereby incorporated by reference in its entirety. Said copy, created on Jan. 20, 2023, is named 57837-708301_SL.xml and is 36,671 bytes in size.

BRIEF SUMMARY

Currently, there are needs in the development of effective drugs and methods in treating the XLRP. The compositions, recombinant adeno-associated virus (rAAV) particles, systems, methods, and kits of the present disclosure solve the needs thereof.

Disclosed herein, are compositions. In an aspect, a composition comprises (i) a first polynucleotide, wherein the first polynucleotide comprises a first sequence operably linked to a first promoter and a second sequence operably linked to a second promoter, the first sequence encoding an adeno-associated virus (AAV) capsid protein, the second sequence encoding an AAV rep protein, the first promoter and the second promoter are suitable for expression in insect cells, and (ii) a second polynucleotide, wherein the second polynucleotide comprises a third sequence operably linked to a CMV promoter, a CAG promoter, a MNDU3 promoter, a PGK promoter, a EF1a promoter, or an eye-specific promoter, and wherein the third sequence encodes a retinitis pigmentosa GTPase regulator (RPGR) polypeptide.

In some embodiments, the third sequence encodes an RPGR ORF15 polypeptide. In some embodiments, the third sequence is codon optimized. In some embodiments, the third sequence comprises SEQ ID NO: 2 or a sequence comprising at least 90% identity to SEQ ID NO: 2. In some embodiments, the third sequence comprises SEQ ID NO: 3 or a sequence comprising at least 90% identity to SEQ ID NO: 3. In some embodiments, the third sequence comprises SEQ ID NO: 4 or a sequence comprising at least 90% identity to SEQ ID NO: 4. In some embodiments, the third sequence comprises SEQ ID NO: 5 or a sequence comprising at least 90% identity to SEQ ID NO: 5. In some embodiments, the third sequence comprises SEQ ID NO: 6 or a sequence comprising at least 90% identity to SEQ ID NO: 6.

In some embodiments, the insect cells are Sf9 cells. In some embodiments, the first promoter or the second promoter is a p10 promoter or a polh promoter. In some embodiments, the first promoter or the second promoter is the p10 promoter. In some embodiments, the first promoter or the second promoter is the polh promoter. In some embodiments, the eye-specific promoter is selected from the group consisting of a RPE 65 gene promoter, a cellular retinaldehyde-binding protein (CRALBP), a murine 11-cis-retinol dehydrogenase (RDH) promoter, a rhodopsin promoter, a Rhodoposin kinase (GRK1) promoter, a tissue inhibitor of metalloproteinase-3 (TIMP3) promoter, a photoreceptor retinol binding protein promoter, a vitelliform macular dystrophy 2 promoter, and an Interphotoreceptor retinoid-binding protein (IRBP) promoter.

In some embodiments, the Rhodopsin kinase (GRK1) promoter comprises any one of SEQ ID NOs: 7-8 or a sequence having at least 90% identity to any one of SEQ ID NOs: 7-8. In some embodiments, the Rhodopsin kinase (GRK1) promoter comprises SEQ ID NO: 7 or a sequence having at least 90% identity to SEQ ID NO: 7. In some embodiments, the Rhodopsin kinase (GRK1) promoter comprises SEQ ID NO: 8 or a sequence having at least 90% identity to SEQ ID NO: 8.

In some embodiments, the 3' end of the first sequence further comprises a poly A sequence. In some embodiments, the 3' end of the second sequence further comprises a poly A sequence. In some embodiments, the first sequence and the second sequence are connected by a sequence encoding a linker. In some embodiments, the linker is a cleavable linker. In some embodiments, the linker comprises a sequence encoding a 2A peptide. In some embodiments, the sequence encoding the linker further comprises a promoter. In some embodiments, the promoter is a FMDV promoter. In some embodiments, the 3' end of the third sequence further comprises a poly A sequence.

In some embodiments, the poly A sequence comprises any one of SEQ ID NOs: 9-12 or a sequence having at least 90% identity to any one of SEQ ID NOs: 9-12. In some embodiments, the poly A sequence comprises SEQ ID NO: 9 or a sequence having at least 90% identity to SEQ ID NO: 9. In some embodiments, the poly A sequence comprises SEQ ID NO: 10 or a sequence having at least 90% identity to SEQ ID NO: 10. In some embodiments, the poly A sequence comprises SEQ ID NO: 11 or a sequence having at least 90% identity to SEQ ID NO: 11. In some embodiments, the poly A sequence comprises SEQ ID NO: 12 or a sequence having at least 90% identity to SEQ ID NO: 12.

In some embodiments, the second polynucleotide further comprises a stuffer sequence. In some embodiments, the second polynucleotide further comprises an inverted terminal repeat (ITR) sequence. In some embodiments, the Inverted terminal repeat (ITR) sequence is an adeno-associated virus (AAV) serotype 2 ITR sequence. In some embodiments, the second polynucleotide further comprises a fourth sequence encoding a therapeutic protein. In some embodiments, the therapeutic protein is selected from the group consisting of: RPGRIP1, RPGRIP1L, SMC1, SMC3, Whirlin, PDEδ, and RAB8.

In some embodiments, the third sequence and the fourth sequence are connected by a sequence encoding a linker. In some embodiments, the linker is a cleavable linker. In some embodiments, the linker comprises a sequence encoding a 2A peptide.

In some cases, the composition further comprises an intron sequence. In some cases, the intron sequence comprises SEQ ID NO: 13 or a sequence having at least 90% identity to SEQ ID NO: 13. In some cases, the first polynucleotide comprises an adeno-associated virus (AAV) serotype 5 sequence.

Disclosed herein, are recombinant adeno-associated virus (rAAV) particles. In an aspect, a recombinant adeno-associated virus (rAAV) particle is prepared by introducing any composition described thereof into an insect cell. In some embodiments, the insect cell is a Sf9 cell.

Disclosed herein, are systems for treating X linked retinitis pigmentosa. In an aspect, a system for treating X linked retinitis pigmentosa comprises any recombinant adeno-associated virus (rAAV) particle described thereof and a pharmaceutically acceptable carrier.

Disclosed herein, are methods for treating X linked retinitis pigmentosa. In an aspect, a method for treating X linked retinitis pigmentosa comprises administering to the subject in need thereof any system described thereof.

Disclosed herein, are kits. In an aspect, a kit comprises any system described thereof and instructions.

BRIEF DESCRIPTION OF THE DRAWINGS

The features of the disclosure are set forth with particularity in the appended claims. A better understanding of the features and the disclosure will be obtained by reference to the following detailed description that sets forth illustrative embodiments, in which the principles of the disclosure are utilized, and the accompanying drawings (also "Figure" and "FIG." herein), of which:

FIG. 1A shows a representative image of a western blot of the recombinant RPGR ORF15 proteins expressed from various codon-optimized RPGR ORF15 cDNA constructs in the HEK293T cells. The cells were transfected with the plasmids carrying a set of expression constructs listed in TABLE 2. The lysates of the transfected cells were analyzed by western blot. The RPGR ORF15 (ORF15) protein was identified using an anti-RPGR antibody. The glutamylated RPGR ORF15 protein (ORF15) glutamylation was identified using an anti-GT335 antibody. All constructs expressed a higher level of RPGR ORF15 proteins relative to that of the no plasmid control group. The recombinant RPGR ORF15 protein expressed were also glutamylated, suggesting that they had normal post-translational modification of a wild-type protein. FIG. 1B shows a representative image of a western blot of the recombinant RPGR ORF15 proteins expressed from various codon-optimized RPGR ORF15 cDNA constructs in the HEK293T cells. The cells were transfected with recombinant AAV (rAAV) particles carrying another set of constructs listed in TABLE 2. The lysates of the transfected cells were analyzed by western blot. The RPGR protein ORF15 (ORF15) protein was identified using anti-RPGR antibody. All constructs expressed a higher level of RPGR ORF15 relative to that of the control cells. In FIGS. 1A-B, actin was used as a control (anti-b-actin) protein. For the expression analysis, untransfected cell (no plasmid) was used as a negative control.

FIG. 2A shows the scotopic A-wave defects of the RPGR knockout mice could be statistically significantly rescued when injected with various recombinant AAV (rAAV) particles expressing the recombinant RPGR recombinant proteins. FIG. 2B shows the scotopic B-wave defect of the RPGR knockout mice could be statistically significantly rescued when injected with various recombinant AAV (rAAV) particles expressing the recombinant RPGR recombinant proteins. FIG. 2C shows the photopic B-wave defect of the RPGR knockout mice could be rescued when injected with several recombinant AAV (rAAV) particles expressing the recombinant RPGR recombinant proteins. In FIGS. 2A-C, the mice were injected with the same number of viral particles containing the codon-optimized RPGR constructs. Wild type mice (C57) and RPGR knockout mice injected with a formulation buffer (Vehicle) were used as a positive and negative control, respectively. The injection was carried out using bilateral subretinal injection. The number of eyes injected are summarized in TABLE 3. The scotopic A-wave, scotopic B-wave, and photopic B-wave were measured by electroretinography (ERG) one-month post-injection. Statistical analysis was carried out using one-way ANOVA against Vehicle followed by Bonferroni's multiple comparison test. *$p<0.023$, $p<0.01$, *$p<0.0008$, ****$p<0.0001$.

DETAILED DESCRIPTION

Figure 1A:
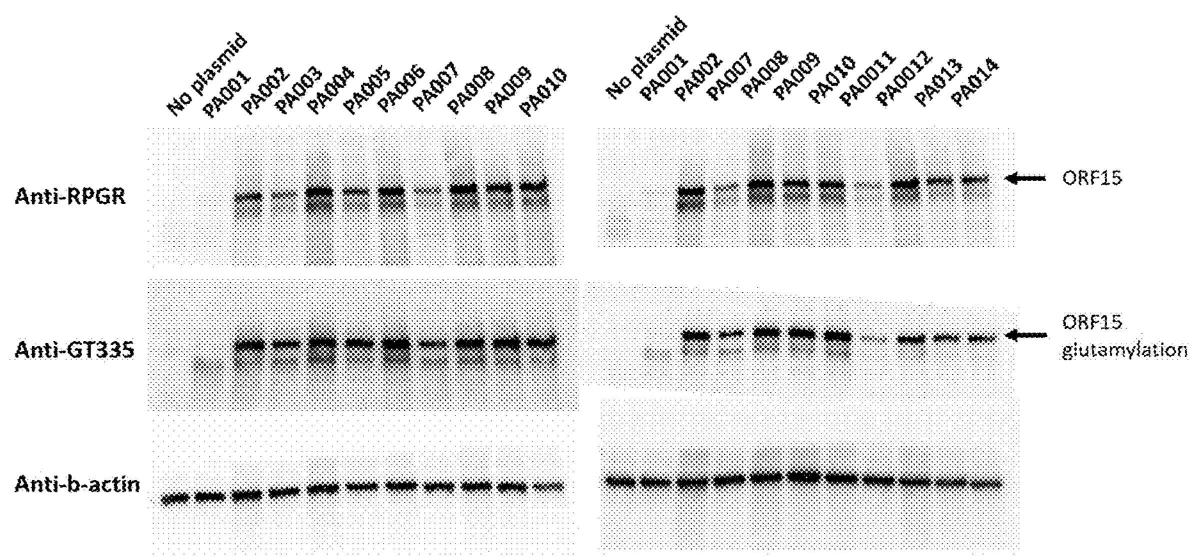
FIGS. 1A-B show that the codon-optimized RPGR polynucleotide sequence can express recombinant RPGR ORF15 protein in a high level in vitro.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

Unless otherwise indicated, the practice of some embodiments disclosed herein comprises conventional techniques of immunology, biochemistry, chemistry, molecular biology, microbiology, cell biology, genomics, and recombinant DNA technologies. See, e.g., Sambrook and Green, Molecular Cloning: A Laboratory Manual, 4th Edition (2012); The Current Protocols in Molecular Biology series (F. M. Ausubel, et al. eds.); The Methods In Enzymology series (Academic Press, Inc.); PCR 2: A Practical Approach (M. J. MacPherson, B. D. Hames and G. R. Taylor eds (1995)), Harlow and Lane, eds. (1988) Antibodies, A Laboratory Manual; and Culture of Animal Cells: A Manual of Basic Technique and Specialized Applications, 6th Edition (R. I. Freshney, ed. (2010)).

Definitions

As used in the specification and claims, the singular forms "a", "an," and "the" include plural references unless the context clearly dictates otherwise. For example, the term "rAAV particle" includes one or more rAAV particles.

The term "about" or "approximately" refers to a particular value within the acceptable error range determined by a person of ordinary skill in the art, which will depend in part on how the value is measured or determined, i.e., the limitations of the measurement system. For example, according to the practice in the art, "about" can mean within 1 or more than 1 standard deviation. Alternatively, "about" can mean a range of up to 20%, up to 10%, up to 5%, or up to 1% of a given value. Alternatively, particularly with respect to biological systems or processes, the term can mean within an order of magnitude, up to 5-fold, or up to 2-fold, of a value. Where particular values can be described in the application and claims, unless otherwise stated the term "about" meaning up to an acceptable error range for the particular value should be assumed.

As used herein, the terms "polypeptide," "peptide," and "protein" are used interchangeably herein to refer to polymers of amino acids of any length. The polymer can be linear, cyclic or branched. The polymer can contain modified amino acids and can be interrupted by non-amino acids. The term also includes amino acid polymers that have been modified, such as by sulfation, glycosylation, lipidation, acetylation, phosphorylation, iodination, methylation, oxidation, proteolytic treatment, phosphorylation, isoprenylation, racemization, selenization, transfer RNA-mediated addition of amino acids to proteins (such as arginylation), ubiquitination, or any other operations, such as conjugation with labeling components. A polypeptide or amino acid sequence "derived" from a given protein refers to the origin of the polypeptide. Preferably, the polypeptide has an amino acid sequence that is substantially the same as the amino acid sequence of the polypeptide encoded in the sequence, or a part thereof, wherein the part consists of at least 10-20 amino acids, at least 20-30 amino acids, at least 30-50 amino acids, or it can be identified immunologically with the polypeptide encoded in the sequence. The term also includes polypeptides expressed from a designated nucleic acid sequence. As used herein, the term "domain" refers to a part of a protein that is physically or functionally distinguished from other parts of the protein or peptide. Physically defined domains include amino acid sequences that are extremely hydrophobic or hydrophilic, such as those that are membrane-bound or cytoplasmic-bound. The domain can also be defined by internal homology caused by gene duplication, for example. Functionally defined domains have different biological functions. For example, the protein-binding domain refers to the part of the protein-binding unit that binds to the protein. The functionally defined domain does not need to be encoded by a continuous amino acid sequence, and the functionally defined domain may contain one or more physically defined domains.

As used herein, the term "amino acid" refers to natural and/or unnatural or synthetic amino acids, including but not limited to D or L optical isomers, as well as amino acid analogs and peptidomimetics. Standard one-letter or three-letter codes are used to designate amino acids. In this context, amino acids are usually represented by one-letter and three-letter abbreviations well known in the art. For example, alanine can be represented by A or Ala.

As used herein, in the case of a polypeptide, a "sequence" is the sequence of amino acids in the polypeptide in the direction from the amino terminal to the carboxy terminal, wherein the residues adjacent to each other in the sequence are in the polypeptide. It is continuous in the primary structure. The sequence can also be a linear sequence of a part of a polypeptide known to contain additional residues in one or two directions.

As used herein, in the case of a polynucleotide, a "sequence" is the sequence of nucleotides in the polynucleotide in the direction from the 5' end to the 3' end, wherein the nucleotides adjacent to each other in the sequence are in the polynucleotide. It is continuous in the primary structure. The sequence can also be a linear sequence of a part of a polynucleotide known to contain additional nucleotides in one or two directions.

As used herein, "identity," "homology," or "sequence identity" refers to the similarity or interchangeability between two or more polynucleotide sequences or between two or more polypeptide sequences. When using program such as Emboss Needle or BestFit to determine the sequence identity, homology, or similarity between two different amino acid sequences, the default settings may be used, or an appropriate scoring matrix may be selected, such as blosum45 or BLOSUM80, to optimize the identity, similarity, or homology score. Preferably, homologous polynucleotides are those that hybridize under stringent conditions as defined herein and have at least 70%, preferably at least 80%, more preferably at least 90%, more preferably at least 95%, more preferably at least 97%, more preferably at least 98%, and even more preferably at least 99% sequence identity. When a sequence of comparable length is optimally aligned, homologous polypeptide preferably has at least 80%, at least 90%, at least 95%, at least 97%, at least 98% sequence identity, or at least 99% sequence identity.

With regard to the polypeptide or polynucleotide herein, the "percent sequence identity (%)" is defined as the percentage of amino acid residues or nucleotides in the query sequence that are identical to the amino acid residues or nucleotides of the second, reference polypeptide/polynucleotide sequence or part thereof calculated after aligning the sequences and introducing gaps if necessary to obtain the maximum sequence identity percentage, and not removing any conservative substitutions that are regarded as part of sequence. The alignment aimed at determining the percentage of amino acid sequence identity can be achieved in various ways within the skill of the art, such as using publicly available computer software, such as the BLAST, BLAST-2, ALIGN, NEEDLE, or Megalign (DNASTAR) software. Those skilled in the art can determine appropriate parameters for measuring alignment, including the full length of the sequences being compared is eligible for any algorithms needed to obtain maximal alignment. The percent identity can be measured over the length of the entire defined polypeptide/polynucleotide sequence, or can be measured over a shorter length, for example, the length of a fragment taken from a larger, defined polypeptide/polynucleotide sequence, such as A fragment of at least 5, at least 10, at least 15, at least 20, at least 50, at least 100, or at least 200 consecutive residues/nucleotides. These lengths are exemplary only, and it should be understood that the forms herein shown in the drawings, or the sequence supported in the Sequence Listing can be used to describe any fragment length thereon may be measured with a percentage of the length.

The proteins described herein may have one or more modifications relative to the reference sequence. The modification may be deletion, insertion or addition, or substitution or substitution of amino acid residues. "Deletion" refers to a change in amino acid sequence due to the lack of one or more amino acid residues. "Insertion" or "addition" refers to an amino acid sequence change that results in the addition of one or more amino acid residues compared to a reference sequence. "Substitution" or "substitution" refers to the replacement of one or more amino acids with different amino acids. In the present disclosure, the mutation of the polypeptide relative to the reference sequence can be determined by comparing the polypeptide with the reference sequence. The optimal alignment of sequences for comparison can be performed according to any known method in the art.

As used herein, the term "extracted" refers to the isolation and/or separation of cellular or other components that are associated with, in nature, polynucleotides, peptides, polypeptides, proteins, antibodies or fragments thereof under normal circumstances. Those skilled in the art should understand that non-naturally occurring polynucleotides, peptides, polypeptides, proteins, antibodies, or fragments thereof do not need to be "isolated" to be distinguished from their naturally occurring counterparts. In addition, "concentrated", "isolated" or "diluted" polynucleotides, peptides, polypeptides, proteins, antibodies, or fragments thereof are distinguishable from their naturally occurring counterparts because of their concentration or number of molecules per unit volume is greater than ("concentrated") or less than its naturally occurring counterpart ("isolated"). Enrichment can be measured based on absolute amounts, such as the weight of solution per unit volume, or it can be measured relative to the second, potentially reference species present in the source mixture.

The terms "polynucleotide", "nucleic acid", "nucleotide" and "oligonucleotide" are used interchangeably. They refer to polymeric forms of nucleotides of any length (whether they ae deoxyribonucleotides or ribonucleotides) or their analogs. A polynucleotide can have any three-dimensional structure and can perform any known or unknown function. The following are non-limiting examples of polynucleotides: coding or non-coding regions of genes or gene fragments, loci determined from linkage analysis, exons, introns, messenger RNA (mRNA), transfer RNA, ribosomal RNA, ribozymes, cDNA, recombinant polynucleotides, branched polynucleotides, isolated plasmids, vectors, any DNA isolated sequence, any RNA sequence, nucleic acid probes, primers, or a synthetic oligonucleotide DNA. Polynucleotides may contain modified nucleotides, such as methylated nucleotides and nucleotide analogs. If present, modifications to the nucleotide structure can be imparted before or after polymer assembly. The sequence of nucleotides can be interrupted by non-nucleotide components. The polynucleotide can be further modified after polymerization, for example, by conjugation with a labeling component. When referring to a DNA/RNA, A can mean adenine, C can mean cytosine, G can mean guanine, T can mean thymine, U can mean uracil. U and T can be used interchangeably when referring to a DNA or an RNA.

When applied to polynucleotides, "recombinant" means that the polynucleotide is the product of cloning, restriction digestion, ligation, other procedures that produce constructs different from those found in nature, or any combinations thereof. When applied to polypeptides, "recombinant" means that the polypeptide is the expressed/translated product of a recombinant polynucleotide.

The terms "gene" or "gene fragment" are used interchangeably herein. They refer to a polynucleotide containing at least one open reading frame, the open reading frame capable of encoding a particular protein after transcription and translation. Gene or gene fragment may be a gene group, the cDNA, or synthetic, as long as the polynuclear nucleotide comprises at least one open reading frame, the open reading frame may cover the entire coding region or a section thereof.

The term "operably connected" or "effectively connected" refers to the juxtaposition of the components to allow them to function in their intended manner. For example, if a promoter sequence promotes transcription of a coding sequence, the promoter sequence is operably linked to the coding sequence.

As used herein, "expression" refers to the process by which polynucleotides are transcribed into mRNAs, and/or the process by which transcribed mRNAs (also referred to as "transcripts") is subsequently translated into peptides, polypeptides, or proteins. The transcripts and the encoded polypeptides are collectively referred to as gene products. If the polynucleotide is derived from genomic DNA, expression may include splicing of mRNA in eukaryotic cells.

As used herein, the term "vector" refers to a nucleic acid delivery vehicle into which polynucleotides can be inserted. When the vector can express the protein encoded by the inserted polynucleotide, the vector is called an expression vector. The vector can be introduced into the host cell through transformation, transduction or transfection, so that the genetic material it carries can be expressed in the host cell. Vectors are well known to those skilled in the art, including but not limited to: plasmids; phagemids; artificial chromosomes, such as yeast artificial chromosomes (YAC), bacterial artificial chromosomes (BAC) or artificial chromosomes (PAC) derived from P1; bacteriophages such as lambda phage or M13 phage body and animal viruses. Animal viruses that can be used as vectors include, but are not limited to, retroviruses (including lentiviruses), adenoviruses, adeno-associated viruses, herpes viruses (such as herpes simplex virus), poxviruses, baculoviruses, papillomaviruses, and papillae Polyoma vacuole virus (such as SV40). A vector can contain a variety of elements that control expression, including but not limited to promoter sequences, transcription initiation sequences, enhancer sequences, selection elements, and reporter genes. In addition, the vector may also contain an origin of replication site.

The term "codon optimization" as used herein refers to the use of redundancy in the genetic code to change the nucleotide sequence while maintaining the same protein sequence it encodes. In some cases, codon optimization may be increased or decreased to promote the expression of the protein encoded. This is done by selecting the preference for codon usage for specific cell types such as the relative abundance of tRNA in the cell type. In some cases, a rare tRNA codon may be selected to reduce the expression in a particular cell type. In some cases, codon optimization can also increase the fidelity of sequence replication, that is, less mutations occur during the polynucleotide replication cycle, such as during cloning.

As used herein, the term "host cell" refers to a cell that can be used to be introduced with a vector, which includes, but is not limited to, prokaryotic cells such as *Escherichia coli* or *Bacillus subtilis*, or yeast or fungal cells such as *Aspergillus*, or insect cells such as *Drosophila* S2 cells or Sf9 cells, or animal cells such as fibroblasts, CHO cells, COS cells, NSO cells, HeLa cells, BHK cells, HEK293 cells or human cells.

An "effective amount" as used herein refers to at least the minimum amount required to achieve a measurable improvement or prevention of a particular condition. The effective amount herein can vary with the patient's disease state, age, sex, weight and other factors. An effective amount is also an amount in which the therapeutic benefit exceeds any toxic or adverse effects of the treatment. In the treatment of cancer or tumor, the effective dose of the drug can have the following effects: reduce the number of cancer cells, reduce tumor size, inhibit the infiltration of cancer cells into peripheral organs, inhibit tumor metastasis, inhibit tumor growth to a certain extent alleviate one or more symptoms related to the disease, or any combinations thereof. The effective amount can be administered in one or more applications or doses.

As used herein, the terms "recipient," "individual," "subject," "host," and "patient" are used interchangeably herein, and refer to any mammalian subject to be diagnosed, medicated, or treated, especially humans.

As used herein, the terms "treatment" and "medication" refer to obtaining a desired pharmacological and/or physiological effect. The effect may be prophylactic in terms of completely or partially preventing the disease or its symptoms, and/or may be therapeutic in terms of partially or completely stabilizing or curing the disease and/or adverse reactions attributed to the disease. "Treatment" as used herein encompasses any treatment of diseases in mammals, such as mice, rats, rabbits, pigs, primates, including humans and other apes, especially humans, and the term includes: (a) preventing a disease or symptom from occurring in subjects who may be susceptible to the disease or symptom but not yet diagnosed; (b) inhibiting disease symptoms; (c) preventing the development of the disease; (d) relieving symptoms of the disease; (e) causing the disease or symptoms to subside; or any combination thereof. The term "kit" as used herein refers to a combination packaged for common use or commercially available. For example, the kit of the present disclosure may include the composition of the present disclosure, and instructions for using the composition or the kit. The term "instructions" refers to the explanatory inserts usually contained in commercial packages of therapeutic products, which contain information about indications, use, dosage, administration, combination therapy, contraindications, warnings about the use of such therapeutic products, or any combination thereof.

While various embodiments of the disclosure have been shown and described herein, it will be obvious to those skilled in the art that such embodiments are provided by way of example only. Numerous variations, changes, and substitutions may occur to those skilled in the art without departing from the disclosure. It should be understood that various alternatives to the embodiments of the disclosure described herein may be employed.

X-Linked Retinitis Pigmentosa (XLRP)

X-linked Retinitis Pigmentosa (XLRP) is the most serious form of retinal degeneration. The disease has an early onset, appearing in the first ten years of life, and rapidly develops afterwards. Since the disease is X-linked, the disease primarily affects male and is less likely to occur in female. However, in some cases, multiple forms of retinal degeneration may be manifested in females carrying heterozygous mutant allele.

Retinitis pigmentosa GTP enzyme regulator (RPGR) is a GTPase binding protein, encoded by RPGR gene in human. Although the function of this protein is not well understood, studies have shown that it plays an important role in the structure of the cilia of the cell. Cilia are tiny, finger-like protrusions that protrude from the surface of many cell types and participate in cell movement and many different signaling pathways. Cilia are necessary for hearing, smell and visual perception. The RPGR gene can produce several RPGR isoforms, one of which is called RPGR ORF15 (1152 amino acids). RPGR ORF15 is mainly expressed in the retina, especially in the photoreceptor cells, and may participate in the photoreceptive process by regulating the function of cilia. RPGR ORF15 has a highly repetitive, purine rich region encoding a glycine/glutamic acid-rich domain in the C-terminal. Codon-optimization may be suitable for generating a stable DNA sequence encoding ORF15 for gene therapy. Functional defects of RPGR are observed in more than 70% of XLRP patients.

Recombinant AAV Vector

Adeno-associated virus (AAV) belong to the parvovirus, a single strand DNA (ssDNA) virus. The full-length genome of the AAV contains approximately 4.7 kilobases (kb), comprising inverted terminal repeats (ITR) DNA sequences at both ends of the virus encompassing two open reading frames (ORF) called rep and cap.

The "AAV inverted terminal repeat (ITR)" sequence is a sequence of about 145 nucleotides that exists at both ends of the natural single-stranded AAV genome. ITR is required for the efficient replication of the genome nucleic acid sequences of the symmetrical AAV particles, which can be used as a viral DNA synthesis origin of replication and are necessary structural components for the recombinant AAV vector.

"rep" gene contains polynucleotide sequences encoding four rep proteins rep78, rep68, rep52, and rep40 required for the life cycle of AAV. "cap" gene contains polynucleotide sequences encoding the AAV capsid proteins VP1, VP2, and VP3 proteins. The AAV capsid proteins VP1, VP2 and VP3 are capable to form a 24-subunit symmetrical AAV capsid through interaction between them.

AAV can effectively infect dividing and non-dividing human cells, and its genome can be integrated into a single chromosomal site in the host genome. Most importantly, although AAV already exists in humans, current research believes that AAV is not related to any disease. Based on its high safety, low immunogenicity, broad host range, ability to mediate stable long-term expression of exogenous genes in vivo, AAV has become the most promising vector system in gene therapy.

To date, 13 AAV serotypes has been identified according to the tissues or different cell types they infect. Further, according to the TABLE 1 below, different AAVs have been developed as advantageous vector systems for transfection of specific cell types. Among the many AAV serotypes, serotype 2 (AAV2) is the most widely studied and used AAV. It can infect, including but not limited to, retinal epithelium, photoreceptor cells, skeletal muscle, central nervous system and liver cells; and has been used as a carrier for many clinical tails in progress.

TABLE 1

AAV Serotypes and the Target Tissues Used in Gene Therapy

| AAV Serotype | Target tissue |
|---|---|
| AAV1, AAV2, AAV4, AAV5, AAV8, AAV9 | Central nervous system |
| AAV1, AAV8, AAV9 | Heart |
| AAV2 | Kidney |
| AAV7, AAV8, AAV9 | Liver |
| AAV4, AAV5, AAV6, AAV9 | Lung |
| AAV8 | Pancreas |
| AAV2, AAV5, AAV8 | Photoreceptors |
| AAV1, AAV2, AAV4, AAV5, AAV8 | Retinal epithelium |
| AAV1, AAV6, AAV7, AAV8, AAV9 | Skeletal muscle |

The term "recombinant AAV vector (rAAV vector)" as used herein refers to a polynucleotide vector containing one or more heterologous sequences (i.e., nucleic acid sequences not derived from AAV) flanked by two AAV ITR sequences. When present in host cells expressing AAV rep and cap proteins, the rAAV vector can replicate and be packaged into AAV virus particles.

The term "recombinant AAV (rAAV) virus" or "rAAV viral particle" as used herein refers to rAAV vector encapsulated by at least one AAV capsid protein into AAV viral particles. Currently used host cells for rAAV viral particle production is derived from mammalian cell types, such as 293 cells, COS cells, HeLa cells, KB cells, and other mammalian cell lines. The rAAV virus particles can be produced in the mammalian cell culture system by providing the rAAV plasmid to the mammalian cell. However, the productivity of the virus of most of the above mammalian cell culture systems is insufficient in meeting the requirements of clinical trials and commercial scale production. To this end, an rAAV virus particle production system using insect cells such as Sf9 cells has recently been developed.

However, to produce AAV in insect cells, some modifications must be made to obtain the correct stoichiometric ratio of the AAV capsid protein.

Baculovirus is a double-stranded circular DNA virus, belonging to Baculoviridae virus family, and has a genome size of 90 kb-230 kb. Baculoviruses are parasites exclusive to arthropods and known to infect more than 600 species of insects. Using Autographa Californica Multicapsid Nuclear Polyhedrosis Virus (AcMNPV), Smith et al. successfully expressed human beta-interferon in the Sf9 cell line in 1983, developing the first baculovirus expression system (Mol. Cell Biol., 1983, 3: 2156-2165). Since then, the baculovirus expression system has been continuously improved and developed, and it has become a very widely used eukaryotic expression system. In 2002, Urabe et al. showed that the baculovirus-infected Sf9 insect cell can support AAV replication, using three recombinant baculoviruses carrying AAV's rep gene, cap gene, and ITR core expression elements to co-infect the Sf9 cells and successfully prepared rAAV virus particles. On this basis, researchers have successively developed systems that are more suitable for large-scale preparation of rAAV virus particles.

At present, there are mainly two methods for large-scale preparation of rAAV virus particles using the baculovirus expression system: Two Bac system and One Bac system. The main process of the two baculovirus systems prepared rAAV viral particles is that the rep gene and the cap gene of the AAV is integrated into one baculovirus genome, and the ITR core element expressing the gene of interest is integrated into another baculovirus genome. The above two recombinant baculoviruses are then used to co-infect host cells to produce rAAV virus particles carrying the target gene. The main process of using One Bac system relies on packaging cell lines to prepare rAAV virus particles. A packaging cell line that can induce the expression of rep genes and cap genes is first established. This packaging cell line is integrated with the rep genes and cap gene expression elements. The rep gene and the cap gene are both placed under the control of the strong baculovirus late gene expression promoter polyhedrin (polh). The hr2 enhancer sequence and the AAV rep protein binding sequence are further inserted upstream of the polh promoter. After being infected with a recombinant baculovirus containing AAV ITR and the target gene, the rep gene and cap gene in the packaging cell line are induced, and the rAAV virus particles containing the target gene insert are produced.

In some embodiments, the rAAV vector used to carry the gene of interest in the rAAV virus particle may also include one or more "expression control elements" The term "expression control element" as used herein refers to a nucleic acid sequence that affects the expression of an operably linked polynucleotide, including polynucleotide sequences that promote the transcription and translation of heterologous polynucleotides. The expression control elements that can be used in the present disclosure include, but are not limited to, promoters, enhancers, intron splicing signals, poly A sequences, or inverted terminal repeats (ITR).

A "promoter" is a DNA sequence located adjacent to a heterologous polynucleotide sequence encoding a target product, which is usually operably linked to an adjacent sequence, such as a heterologous polynucleotide. Compared to the amount expressed in the absence of a promoter, a promoter generally increases the amount of heterologous polynucleotide expression.

An "enhancer" is a sequence that enhances the activity of a promoter. Different from the promoter, an enhancer does not have the promoter activity, and may generally depend on its location relative to the promoter (i.e., upstream or downstream of the promoter). Non-limiting examples of enhancer elements (or portions thereof) that can be used in the present disclosure include baculovirus enhancers and enhancer elements found in insect cells.

A "stuffer sequence" refers to a nucleotide sequence of a larger nucleic acid molecule (such as, but not limited, to a vector), and is usually to create a desired gap or separation between two nucleic acid features (such as, but not limited, between a promoter and a coding sequence) or to extend the nucleic acid molecule a desired length. The stuffer sequence does not contain protein coding information and may have unknown or synthetic origin, not related to other nucleic acid sequences within the larger nucleic acid molecule, or any combination thereof.

Compositions

In one aspect, the present disclosure provides a combination thereof, comprising a first polynucleotide and a second polynucleotide, wherein said first polynucleotide comprises a first promoter operably linked to a first sequence and a second promoter operably linked to a second sequence.

In some embodiments, the first sequence encodes an adeno-associated virus (AAV) cap protein. The cap protein can be any structural protein known in the art that can form a functional AAV capsid (i.e., packaging DNA and infecting target cells). In some embodiments, the cap protein includes VP1, VP2, and VP3. In some embodiments, the cap protein does not need to comprise all of VP1, VP2, and VP3, as long as it can produce a functional AAV capsid. In some embodiments, the cap protein includes VP1 and VP2. In some embodiments, the cap protein comprises VP1 and VP3. In some embodiments, the cap protein includes VP2 and VP3. In some embodiments, the case, the cap protein comprises VP1. In some embodiments, the cap protein includes VP2. In some embodiments, the cap protein includes VP3.

VP1, VP2, or VP3 may be derived from any AAV serotype. In some embodiments, the VP1 may be derived from AAV serotype 1 (AAV1), AAV serotype 2 (AAV2), AAV2 variants (e.g., AAV2.7m8, AAV2(quad Y-F), or AAV2tYF), AAV serotype 3 (AAV3, including serotypes 3A and 3B), AAV serotype 4 (AAV4), the AAV serotype. 5 (AAV5), the AAV serotype. 6 (AAV6), the AAV serotype. 7 (AAV7), the AAV serotype. 8 (AAV8), the AAV serotype. 9 (AAV9), the AAV serotype 10 (AAV10), AAV serotype 11 (AAV11), AAV serotype 12 (AAV12), AAV serotype 13 (AAV13), AAV-Rh10, AAV-Rh74, AAV-2i8 or any other known AAVs. In some embodiments, the VP1 and the wildtype VP1 derived from AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74, or AAV2i8 may have at least 75%, 80%, 85%, 90%, 95%, or more sequence identity. In some embodiments case, the VP1 has one or more amino acid substitutions, deletions, additions, or any combination thereof compared to the wildtype VP1 derived from AAV1, AAV2, AAV3 (including AAV3A and 3B), AAV4, AAV5, AAV6, AAV7, AAV8, of AAV9, AAV10, AAV11, AAV12, AAV13, AAV-Rh10, AAV-Rh74 or AAV-2i8.

In some embodiments, the VP2 may be derived from AAV serotype 1 (AAV1), AAV serotype 2 (AAV2), AAV2 variants (e.g., AAV2.7m8, AAV2(quad Y-F), or AAV2tYF), AAV serotype 3 (AAV3, including serotypes 3A and 3B), AAV serotype 4 (AAV4), the AAV serotype. 5 (AAV5), the AAV serotype. 6 (AAV6), the AAV serotype. 7 (AAV7), the AAV serotype. 8 (AAV8), the AAV serotype. 9 (AAV9), the AAV serotype 10 (AAV10), AAV serotype 11 (AAV11), AAV serotype 12 (AAV12), AAV serotype 13 (AAV13), AAV-Rh10, AAV-Rh74, AAV-2i8 or any other known AAVs. In some embodiments, the VP2 and the wildtype VP2 derived from AAV1, AAV2, AAV3, (including AAV3A and 3B), AAV4, AAV5, AAV6, AAV7, AAV8, AAV9, AAV10, AAV11, AAV12, AAV13, AAV-Rh10, AAV-Rh74, or AAV2i8 may have at least 75%, 80%, 85%, 90%, 95%, or more sequence identity. In some embodiments case, the VP2 has one or more amino acid substitutions, deletions, additions, or any combination thereof compared to the wildtype VP2 derived from AAV1, AAV2, AAV3 (including AAV3A and 3B), AAV4, AAV5, AAV6, AAV7, AAV8, of AAV9, AAV10, AAV11, AAV12, AAV13, AAV-Rh10, AAV-Rh74 or AAV-2i8.

The VP3 may be derived from AAV serotype 1 (AAV1), AAV serotype 2 (AAV2), AAV2 variants (e.g., AAV2.7m8, AAV2(quad Y-F), or AAV2tYF), AAV serotype 3 (AAV3, including serotypes 3A and 3B), AAV serotype 4 (AAV4), the AAV serotype. 5 (AAV5), the AAV serotype. 6 (AAV6), the AAV serotype. 7 (AAV7), the AAV serotype. 8 (AAV8), the AAV serotype. 9 (AAV9), the AAV serotype 10 (AAV10), AAV serotype 11 (AAV11), AAV serotype 12 (AAV12), AAV serotype 13 (AAV13), AAV-Rh10, AAV-Rh74, AAV-2i8 or any other known AAVs. In some embodiments, the VP3 and the wildtype VP3 derived from AAV1, AAV2, AAV2 variants (e.g., AAV2.7m8, AAV2(quad Y-F), or AAV2tYF), AAV3, (including AAV3A and 3B), AAV4, AAV5, AAV6, AAV7, AAV8, AAV9, AAV10, AAV11, AAV12, AAV13, AAV-Rh10, AAV-Rh74, or AAV2i8 may have at least 75%, 80%, 85%, 90%, 95%, or more sequence identity. In some embodiments case, the VP3 has one or more amino acid substitutions, deletions, additions, or any combination thereof compared to the wildtype VP3 derived from AAV1, AAV2, AAV2 variants (e.g., AAV2.7m8, AAV2 (quad Y-F), or AAV2tYF), AAV3 (including AAV3A and 3B), AAV4, AAV5, AAV6, AAV7, AAV8, of AAV9, AAV10, AAV11, AAV12, AAV13, AAV-Rh10, AAV-Rh74 or AAV-2i8.

In some embodiments, the cap protein comprises VP1, VP2, VP3, or any combinations thereof derived from AAV of the same serotype; for example, the cap protein may comprise VP1, VP2, VP3, or any combinations thereof derived from AAV2, AAV2 variants (e.g., AAV2.7m8, AAV2 (quad Y-F), or AAV2tYF), AAV5, or AAV8. In some embodiments, the cap comprises VP1, VP2, VP3, or any combinations thereof derived from different serotypes of AAV; for example, the cap protein may comprise any one or more of VP1, VP2, VP3, or any combination thereof of AAV1, AAV2, AAV2 variants (e.g., AAV2.7m8, AAV2(quad Y-F), or AAV2tYF), AAV3, (including AAV3A and 3B), AAV4, AAV5, AAV6, AAV7, AAV8, AAV9, AAV10, AAV11, AAV12, AAV13, AAV-Rh10, AAV-Rh74, or AAV-2i8.

In some embodiments, the cap protein may be cloned into pUC57, pFastBac1, modified pUC57, or modified pFastBac1. In some embodiments, the cap protein may be cloned into pUC57. In some embodiments, the cap protein may be cloned into pFastBac1. In some embodiments, the cap protein may be cloned into modified pUC57. In some embodiments, the cap protein may be cloned into modified pFastBac1.

In some embodiments, the first sequence encoding the cap protein is operably linked to a first promoter. The first promoter may be any suitable promoter known in the art that can drive the expression of the cap protein. In some embodiments, the first promoter may be a tissue-specific promoter, a constitutive promoter, or a regulatable promoter. In some embodiments, the first promoter can be selected from different sources, for example, the first promoter can be a viral promoter, a plant promoter, or a mammalian promoter.

The first promoter can include, but are not limited to, a human cytomegalovirus (CMV) immediate-early enhancer or promoter, a SV40 early enhancer or promoter, a JC polyomavirus promoter, a myelin basic Protein (MBP) or a glial fibrillary acidic protein (GFAP) promoter, a herpes simplex virus (HSV-1) latency-related promoter (LAP), a Rous sarcoma virus (RSV) long terminal repeat (LTR) promoter, a neuron specific promoter (NSE), a platelet-derived growth factor (PDGF) promoter, hSYN, a melanin aggregation hormone (MCH) promoter, CBA, a matrix metal protein promoter (MPP), a chicken β-actin promoter, CAG, MNDU3, PGK and an EF1a promoter.

In some embodiments, the first promoter is a promoter suitable for expression in insect cells. In some embodiments, the promoter suitable for expression in insect cells include, but are not limited to a polh promoter, a p10 promoter, a basic promoter, an inducible promoter, an E1 promoter, or a ΔE1 promoter. In some embodiments, the first promoter is a polh promoter. In some embodiments, the first promoter is a p10 promoter.

In some embodiments, the 3' end of a first sequence further comprises a polyadenylation sequence or "poly A sequence". In some embodiments, the 3' end of a second sequence further comprises a polyadenylation sequence or "poly A sequence". In some embodiments, the polyadenylation sequence or "poly A sequence" may range from about 1-500 base pairs (bp). In some embodiments, the polyadenylation sequence or "poly A sequence" may be, but is not limited to, 1, 2, 3, 4, 5, 6, 7, 8, 9, 10, 20, 30, 50, 100, 200, or 500 nucleotides.

In some embodiments, the poly A sequence comprises a sequence encoding a human RPGR ORF15 polypeptide. In some embodiments, the poly A sequence comprises a sequence having at least 75% identity with any one of SEQ ID NOs: 9-12. In some embodiments, the poly A sequence comprises a sequence having at least 80% identity with any one of SEQ ID NOs: 9-12. In some embodiments, the poly A sequence comprises a sequence having at least 85% identity with any one of SEQ ID NOs: 9-12. In some embodiments, the poly A sequence comprises a sequence having at least 90% identity with any one of SEQ ID NOs: 9-12. In some embodiments, the poly A sequence comprises a sequence having at least 95% identity with any one of SEQ ID NOs: 9-12. In some embodiments, the poly A sequence comprises a sequence having at least 96% identity with any one of SEQ ID NOs: 9-12. In some embodiments, the poly A sequence comprises a sequence having at least 97% identity with any one of SEQ ID NOs: 9-12. In some embodiments, the poly A sequence comprises a sequence having at least 98% identity with any one of SEQ ID NOs: 9-12. In some embodiments, the poly A sequence comprises a sequence having at least 99% identity with any one of SEQ ID NOs: 9-12. In some embodiments, the poly A sequence comprises the sequence of SEQ ID NOs: 9-12. In some embodiments, the poly A sequence comprises a sequence having one or more nucleotide mutations, substitutions, deletions or additions compared to SEQ ID NOs: 9-12.

In some embodiments, the poly A sequence comprises a sequence encoding a human RPGR ORF15 polypeptide. In some embodiments, the poly A sequence comprises a sequence having at least 75% identity with SEQ ID NO: 9. In some embodiments, the poly A sequence comprises a sequence having at least 80% identity with SEQ ID NO: 9.

In some embodiments, the poly A sequence comprises a sequence having at least 85% identity with SEQ ID NO: 9. In some embodiments, the poly A sequence comprises a sequence having at least 90% identity with SEQ ID NO: 9. In some embodiments, the poly A sequence comprises a sequence having at least 95% identity with SEQ ID NO: 9. In some embodiments, the poly A sequence comprises a sequence having at least 96% identity with SEQ ID NO: 9. In some embodiments, the poly A sequence comprises a sequence having at least 97% identity with SEQ ID NO: 9. In some embodiments, the poly A sequence comprises a sequence having at least 98% identity with SEQ ID NO: 9. In some embodiments, the poly A sequence comprises a sequence having at least 99% identity with SEQ ID NO: 9. In some embodiments, the poly A sequence comprises the sequence of SEQ ID NO: 9. In some embodiments, the poly A sequence comprises a sequence having one or more nucleotide mutations, substitutions, deletions or additions compared to SEQ ID NO: 9.

In some embodiments, the poly A sequence comprises a sequence encoding a human RPGR ORF15 polypeptide. In some embodiments, the poly A sequence comprises a sequence having at least 75% identity with SEQ ID NO: 10. In some embodiments, the poly A sequence comprises a sequence having at least 80% identity with SEQ ID NO: 10. In some embodiments, the poly A sequence comprises a sequence having at least 85% identity with SEQ ID NO: 10. In some embodiments, the poly A sequence comprises a sequence having at least 90% identity with SEQ ID NO: 10. In some embodiments, the poly A sequence comprises a sequence having at least 95% identity with SEQ ID NO: 10. In some embodiments, the poly A sequence comprises a sequence having at least 96% identity with SEQ ID NO: 10. In some embodiments, the poly A sequence comprises a sequence having at least 97% identity with SEQ ID NO: 10. In some embodiments, the poly A sequence comprises a sequence having at least 98% identity with SEQ ID NO: 10. In some embodiments, the poly A sequence comprises a sequence having at least 99% identity with SEQ ID NO: 10. In some embodiments, the poly A sequence comprises the sequence of SEQ ID NO: 10. In some embodiments, the poly A sequence comprises a sequence having one or more nucleotide mutations, substitutions, deletions or additions compared to SEQ ID NO: 10.

In some embodiments, the poly A sequence comprises a sequence encoding a human RPGR ORF15 polypeptide. In some embodiments, the poly A sequence comprises a sequence having at least 75% identity with SEQ ID NO: 11. In some embodiments, the poly A sequence comprises a sequence having at least 80% identity with SEQ ID NO: 11. In some embodiments, the poly A sequence comprises a sequence having at least 85% identity with SEQ ID NO: 11. In some embodiments, the poly A sequence comprises a sequence having at least 90% identity with SEQ ID NO: 11. In some embodiments, the poly A sequence comprises a sequence having at least 95% identity with SEQ ID NO: 11. In some embodiments, the poly A sequence comprises a sequence having at least 96% identity with SEQ ID NO: 11. In some embodiments, the poly A sequence comprises a sequence having at least 97% identity with SEQ ID NO: 11. In some embodiments, the poly A sequence comprises a sequence having at least 98% identity with SEQ ID NO: 11. In some embodiments, the poly A sequence comprises a sequence having at least 99% identity with SEQ ID NO: 11. In some embodiments, the poly A sequence comprises the sequence of SEQ ID NO: 11. In some embodiments, the poly A sequence comprises a sequence having one or more nucleotide mutations, substitutions, deletions or additions compared to SEQ ID NO: 11.

In some embodiments, the poly A sequence comprises a sequence encoding a human RPGR ORF15 polypeptide. In some embodiments, the poly A sequence comprises a sequence having at least 75% identity with SEQ ID NO: 12. In some embodiments, the poly A sequence comprises a sequence having at least 80% identity with SEQ ID NO: 12. In some embodiments, the poly A sequence comprises a sequence having at least 85% identity with SEQ ID NO: 12. In some embodiments, the poly A sequence comprises a sequence having at least 90% identity with SEQ ID NO: 12. In some embodiments, the poly A sequence comprises a sequence having at least 95% identity with SEQ ID NO: 12. In some embodiments, the poly A sequence comprises a sequence having at least 96% identity with SEQ ID NO: 12. In some embodiments, the poly A sequence comprises a sequence having at least 97% identity with SEQ ID NO: 12. In some embodiments, the poly A sequence comprises a sequence having at least 98% identity with SEQ ID NO: 12. In some embodiments, the poly A sequence comprises a sequence having at least 99% identity with SEQ ID NO: 12. In some embodiments, the poly A sequence comprises the sequence of SEQ ID NO: 12. In some embodiments, the poly A sequence comprises a sequence having one or more nucleotide mutations, substitutions, deletions or additions compared to SEQ ID NO: 12.

In some embodiments, the second sequence encodes an AAV rep protein, where the rep protein can be a replication protein necessary for any rAAV vector to replicate and be packaged into rAAV viral particles. In some embodiments, the rep protein comprises rep78, rep68, rep52 or rep40. In some embodiments, the rep protein may not comprise all of rep78, rep68, rep52, or rep40, as long as it can allow the rAAV vector to replicate or be packaged into rAAV virus particles. In some embodiment, the rep protein comprises any three of rep78, rep 68, rep52 or rep 40. In some embodiment, the rep protein comprises any two of rep78, rep 68, rep52 or rep 40. In some embodiment, the rep protein comprises any one of rep78, rep 68, rep52 or rep 40. In some embodiment, the rep protein comprises rep78 or rep52. In some embodiment, the rep protein comprises rep78 or rep 40. In some embodiment, the rep protein comprises rep68 or rep52. In some embodiment, the rep protein comprises rep68 or rep40.

rep78, rep68, rep52, or rep40 may be derived from any AAV serotype. In some embodiments, the rep78 may be derived from AAV serotype 1 (AAV1), AAV serotype 2 (AAV2), AAV2 variants (e.g., AAV2.7m8, AAV2(quad Y-F), or AAV2tYF), AAV serotype 3 (AAV3, including serotypes 3A and 3B), AAV serotype 4 (AAV4), the AAV serotype. 5 (AAV5), the AAV serotype. 6 (AAV6), the AAV serotype. 7 (AAV7), the AAV serotype. 8 (AAV8), the AAV serotype. 9 (AAV9), the AAV serotype 10 (AAV10), AAV serotype 11 (AAV11), AAV serotype 12 (AAV12), AAV serotype 13 (AAV13), AAV-Rh10, AAV-Rh74, AAV-2i8 or any other known AAVs. In some embodiments, the rep78 and the wildtype rep78 derived from AAV1, AAV2, AAV2 variants (e.g., AAV2.7m8, AAV2(quad Y-F), or AAV2tYF), AAV3, (including AAV3A and 3B), AAV4, AAV5, AAV6, AAV7, AAV8, AAV9, AAV10, AAV11, AAV12, AAV13, AAV-Rh10, AAV-Rh74, or AAV2i8 may have at least 75%, 80%, 85%, 90%, 95%, or more sequence identity. In some embodiments case, the rep78 has one or more amino acid substitutions, deletions, additions, or any combination thereof compared to the wildtype rep78 derived from AAV1, AAV2, AAV2 variants (e.g., AAV2.7m8, AAV2(quad Y-F), or AAV2tYF), AAV3 (including AAV3A and 3B), AAV4, AAV5, AAV6, AAV7, AAV8, of AAV9, AAV10, AAV11, AAV12, AAV13, AAV-Rh10, AAV-Rh74 or AAV-2i8.

In some embodiments, the rep68 may be derived from AAV serotype 1 (AAV1), AAV serotype 2 (AAV2), AAV2 variants (e.g., AAV2.7m8, AAV2(quad Y-F), or AAV2tYF), AAV serotype 3 (AAV3, including serotypes 3A and 3B), AAV serotype 4 (AAV4), the AAV serotype. 5 (AAV5), the AAV serotype. 6 (AAV6), the AAV serotype. 7 (AAV7), the AAV serotype. 8 (AAV8), the AAV serotype. 9 (AAV9), the AAV serotype 10 (AAV10), AAV serotype 11 (AAV11), AAV serotype 12 (AAV12), AAV serotype 13 (AAV13), AAV-Rh10, AAV-Rh74, AAV-2i8 or any other known AAVs. In some embodiments, the rep68 and the wildtype rep68 derived from AAV1, AAV2, AAV2 variants (e.g., AAV2.7m8, AAV2(quad Y-F), or AAV2tYF), AAV3, (including AAV3A and 3B), AAV4, AAV5, AAV6, AAV7, AAV8, AAV9, AAV10, AAV11, AAV12, AAV13, AAV-Rh10, AAV-Rh74, or AAV2i8 may have at least 75%, 80%, 85%, 90%, 95%, or more sequence identity. In some embodiments case, the rep68 has one or more amino acid substitutions, deletions, additions, or any combination thereof compared to the wildtype rep68 derived from AAV1, AAV2, AAV2 variants (e.g., AAV2.7m8, AAV2(quad Y-F), or AAV2tYF), AAV3 (including AAV3A and 3B), AAV4, AAV5, AAV6, AAV7, AAV8, of AAV9, AAV10, AAV11, AAV12, AAV13, AAV-Rh10, AAV-Rh74 or AAV-2i8.

In some embodiments, the rep52 may be derived from AAV serotype 1 (AAV1), AAV serotype 2 (AAV2), AAV2 variants (e.g., AAV2.7m8, AAV2(quad Y-F), or AAV2tYF), AAV serotype 3 (AAV3, including serotypes 3A and 3B), AAV serotype 4 (AAV4), the AAV serotype. 5 (AAV5), the AAV serotype. 6 (AAV6), the AAV serotype. 7 (AAV7), the AAV serotype. 8 (AAV8), the AAV serotype. 9 (AAV9), the AAV serotype 10 (AAV10), AAV serotype 11 (AAV11), AAV serotype 12 (AAV12), AAV serotype 13 (AAV13), AAV-Rh10, AAV-Rh74, AAV-2i8, or any other known AAVs. In some embodiments, the rep52 and the wildtype rep52 derived from AAV1, AAV2, AAV2 variants (e.g., AAV2.7m8, AAV2(quad Y-F), or AAV2tYF), AAV3, (including AAV3A and 3B), AAV4, AAV5, AAV6, AAV7, AAV8, AAV9, AAV10, AAV11, AAV12, AAV13, AAV-Rh10, AAV-Rh74, or AAV2i8 may have at least 75%, 80%, 85%, 90%, 95%, or more sequence identity. In some embodiments case, the rep52 has one or more amino acid substitutions, deletions, additions, or any combination thereof compared to the wildtype rep52 derived from AAV1, AAV2, AAV2 variants (e.g., AAV2.7m8, AAV2(quad Y-F), or AAV2tYF), AAV3 (including AAV3A and 3B), AAV4, AAV5, AAV6, AAV7, AAV8, of AAV9, AAV10, AAV11, AAV12, AAV13, AAV-Rh10, AAV-Rh74 or AAV-2i8.

In some embodiments, the rep protein comprises rep78, rep68, rep52, or rep40, or any combinations thereof derived from AAV of the same serotype; for example, the rep protein may comprise rep78, rep68, rep52, rep40, or any combinations thereof derived from AAV2. In some embodiments, the rep protein may also comprise rep78, rep68, rep52, rep40, or any combinations thereof derived from AAV2 variants (e.g., AAV2.7m8, AAV2(quad Y-F), or AAV2tYF). In some embodiments, the rep protein comprises rep78, rep68, rep52, rep40, or any combinations thereof derived from different serotypes of AAVs; for example, the rep protein may comprise any one or more of rep78, rep68, rep52, rep40, or any combination thereof of AAV1, AAV2, AAV2 variants (e.g., AAV2.7m8, AAV2(quad Y-F), or AAV2tYF), AAV3, (including AAV3A and 3B), AAV4, AAV5, AAV6, AAV7, AAV8, AAV9, AAV10, AAV11, AAV12, AAV13, AAV-Rh10, AAV-Rh74, or AAV-2i8.

In some embodiments, the second sequence encoding the rep protein is operably linked to a second promoter. The second promoter may be any suitable promoter known in the art that can drive the expression of the rep protein. In some embodiments, the second promoter may be a tissue-specific promoter, a constitutive promoter, or a regulatable promoter. In some embodiments, the second promoter can be selected from different sources, for example, the second promoter can be a viral promoter, a plant promoter, or a mammalian promoter.

In some embodiments, the rep protein may be cloned into pUC57, pFastBac1, modified pUC57, or modified pFastBac1. In some embodiments, the rep protein may be cloned into pUC57. In some embodiments, the rep protein may be cloned into pFastBac1. In some embodiments, the rep protein may be cloned into modified pUC57. In some embodiments, the rep protein may be cloned into modified pFastBac1.

The second promoter can include, but are not limited to, a human cytomegalovirus (CMV) immediate-early enhancer or promoter, a SV40 early enhancer or promoter, a JC polyomavirus promoter, a myelin basic protein (MBP) or a glial fibrillary acidic protein (GFAP) promoter, a herpes simplex virus (HSV-1) latency-related promoter (LAP), a Rous sarcoma virus (RSV) long terminal repeat (LTR) promoter, a neuron specific promoter (NSE), a platelet-derived growth factor (PDGF) promoter, hSYN, a melanin aggregation hormone (MCH) promoter, CBA, a matrix metal protein promoter (MPP), a chicken β-actin promoter, CAG, MNDU3, PGK and an EF1a promoter.

In some embodiments, the second promoter is a promoter suitable for expression in insect cells. In some embodiments, the promoter suitable for expression in insect cells include, but are not limited to a polh promoter, a p10 promoter, a basic promoter, an inducible promoter, an E1 promoter, or a ΔE1 promoter. In some embodiments, the second promoter is a polh promoter. In some embodiments, the second promoter is a p10 promoter.

In some embodiments, the cap protein and rep protein are derived from AAV of the same serotype; for example, the cap protein and rep protein may be derived from AAV1, AAV2, AAV2 variants (e.g., AAV2.7m8, AAV2(quad Y-F), or AAV2tYF), AAV3 (including AAV3A and 3B), AAV4, AAV5, AAV6, AAV7, AAV8, of AAV9, AAV10, AAV11, AAV12, AAV13, AAV-Rh10, AAV-Rh74, AAV-2i8, or any other known AAVs.

In some embodiments, the cap protein and the rep protein are derived from different serotypes of AAV; for example, the cap protein and the rep protein may be derived from AAV1, AAV2, AAV2 variants (e.g., AAV2.7m8, AAV2(quad Y-F), or AAV2tYF), AAV3, (including AAV3A and 3B), AAV4, AAV5, AAV6, AAV7, AAV8, AAV9, AAV10, AAV11, AAV12, AAV13, AAV-Rh10, AAV-Rh74, AAV-2i8, or any other known AAVs. For example, in some embodiments, the cap protein may be derived from AAV2, and the rep protein is derived from the AAV5. In some embodiments, the cap protein may be derived from AAV2 variants (e.g., AAV2.7m8, AAV2(quad Y-F), or AAV2tYF), and the rep protein is derived from the AAV5.

In some embodiments, the first promoter and the second promoter may be the same promoter. For example, the first promoter and the second promoter may be selected from the group consisting of a polh promoter, a p10 promoter, a basic promoter, an inducible promoter, an E1 promoters, and a ΔE1 promoter. For example, in some embodiments, the first promoter and the second promoter are both polh promoters. In some embodiments, the first promoter and the second promoter are both p10 promoters.

In some embodiments, the first promoter and the second promoter may comprise different promoters. For example, the first promoter and the second promoter may be from the group consisting of a polh promoter, a p10 promoter, a basic promoter, an inducible promoter, an E1 promoters, and a ΔE1 promoter. For example, in some embodiments, the first promoter is the polh promoter and the second promoter is the p10 promoter. In some embodiments, the first promoter is the p10 promoter and the second promoter is the polh promoter.

In some embodiments, the first or second promoter may be cloned into pUC57, pFastBac1, modified pUC57, or modified pFastBac1. In some embodiments, the first or second promoter may be cloned into pUC57. In some embodiments, the first or second promoter may be cloned into pFastBac1. In some embodiments, the first or second promoter may be cloned into modified pUC57. In some embodiments, the first or second promoter may be cloned into modified pFastBac1.

In some embodiments, the cap protein, rep protein, first promoter, and second promoter may be cloned into pUC57, pFastBac1, modified pUC57, or modified pFastBac1. In some embodiments, the cap protein, rep protein, first promoter, and second promoter may be cloned into pUC57. In some embodiments, the cap protein, rep protein, first promoter, and second promoter may be cloned into pFastBac1. In some embodiments, the cap protein, rep protein, first promoter, and second promoter may be cloned into modified pUC57. In some embodiments, the cap protein, rep protein, first promoter, and second promoter may be cloned into modified pFastBac1.

In some embodiments, the first sequence and the second sequence are linked by a sequence encoding a linker. In some embodiments, the cleavable linker is a sequence comprising a 2A peptide. In some embodiments, the 2A peptide may be selected from the 2A peptides derived from Aphthorvirus or Cardiovirus, such as foot-and-mouth disease virus (FMDV), Equine rhinitis A virus (ERAV), *Thosea asigna* virus (TaV) or porcine teschovirus (PTV-1). In some embodiments, the sequence encoding the linker further comprises a promoter sequence. In some embodiments, the promoter is an FMDV promoter.

In some embodiments, the second polynucleotide in the composition of the present disclosure comprises a third polynucleotide operably linked to a CMV, CAG, MNDU3, PGK, EFla promoter or an eye-specific promoter, wherein the third sequence encodes an RPGR ORF15 polypeptide. In some embodiments, the 3' end of a third sequence further comprise the poly A sequence. The sequence may comprise any poly A sequences described elsewhere in this disclosure.

The RPGR polypeptides described herein may be RPGR and variants thereof derived from any mammal. In some embodiments, the mammal includes, but is not limited to, primates (e.g., humans), cows, dogs, cats, or rodents (e.g., guinea pigs, rats, or mice). In some embodiments, the RPGR polypeptide described herein is a human derived RPGR or a variant thereof. In some embodiments, the RPGR polypeptide described herein is RPGR ORF15 or a variant thereof. In some embodiments, the RPGR ORF15 polypeptide described herein is a human derived RPGR ORF15 or a variant thereof.

In some embodiments, the RPGR polypeptides described herein comprise a sequence that is at least 75% identical to the human RPGR. In some embodiments, the RPGR polypeptides described herein comprise a sequence that is at least 80% identical to the human RPGR. In some embodiments, the RPGR polypeptides described herein comprise a sequence that is at least 85% identical to the human RPGR. In some embodiments, the RPGR polypeptides described herein comprise a sequence that is at least 90% identical to the human RPGR. In some embodiments, the RPGR polypeptides described herein comprise a sequence that is at least 95% identical to the human RPGR. In some embodiments, the RPGR polypeptides described herein comprise a sequence that is at least 96% identical to the human RPGR. In some embodiments, the RPGR polypeptides described herein comprise a sequence that is at least 97% identical to the human RPGR. In some embodiments, the RPGR polypeptides described herein comprise a sequence that is at least 98% identical to the human RPGR. In some embodiments, the RPGR polypeptides described herein comprise a sequence that is at least 99% identical to the human RPGR. In some embodiments, the RPGR polypeptides described herein comprise a sequence of the human RPGR. In some embodiments, the RPGR polypeptide described herein comprises a sequence that has one or more amino acid mutations, substitutions, deletions, or additions compared to the RPGR.

In some embodiments, the RPGR polypeptide described herein comprise a sequence that is at least 75% identical to the human RPGR ORF15. In some embodiments, the RPGR polypeptide described herein comprise a sequence that is at least 80% identical to the human RPGR ORF15. In some embodiments, the RPGR polypeptide described herein comprise a sequence that is at least 85% identical to the human RPGR ORF15. In some embodiments, the RPGR polypeptide described herein comprise a sequence that is at least 90% identical to the human RPGR ORF15. In some embodiments, the RPGR polypeptide described herein comprise a sequence that is at least 95% identical to the human RPGR ORF15. In some embodiments, the RPGR polypeptide described herein comprise a sequence that is at least 96% identical to the human RPGR ORF15. In some embodiments, the RPGR polypeptide described herein comprise a sequence that is at least 97% identical to the human RPGR ORF15. In some embodiments, the RPGR polypeptide described herein comprise a sequence that is at least 98% identical to the human RPGR ORF15. In some embodiments, the RPGR polypeptide described herein comprise a sequence that is at least 99% identical to the human RPGR ORF15. In some embodiments, the RPGR polypeptides described herein comprise a sequence of the human RPGR ORF15. In some embodiments, the RPGR ORF15 polypeptide described herein comprises a sequence that has one or more amino acid mutations, substitutions, deletions, or additions compared to the human RPGR ORF15.

In some embodiments, the RPGR ORF15 polypeptide comprises the sequence of SEQ ID NO: 1. In some embodiments, the RPGR ORF15 polypeptide comprises a sequence that is at least 75% identical to SEQ ID NO: 1. In some embodiments, the RPGR ORF15 polypeptide comprises a sequence that is at least 80% identical to SEQ ID NO: 1. In some embodiments, the RPGR ORF15 polypeptide comprises a sequence that is at least 85% identical to SEQ ID NO: 1. In some embodiments, the RPGR ORF15 polypeptide comprises a sequence that is at least 90% identical to SEQ ID NO: 1. In some embodiments, the RPGR ORF15 polypeptide comprises a sequence that is at least 95% identical to SEQ ID NO: 1. In some embodiments, the RPGR ORF15 polypeptide comprises a sequence that is at least 96% identical to SEQ ID NO: 1. In some embodiments, the RPGR ORF15 polypeptide comprises a sequence that is at least 97% identical to SEQ ID NO: 1. In some embodiments, the RPGR ORF15 polypeptide comprises a sequence that is at least 98% identical to SEQ ID NO: 1. In some embodiments, the RPGR ORF15 polypeptide comprises a sequence that is at least 99% identical to SEQ ID NO: 1. In some embodiments, the RPGR ORF15 polypeptide comprises a sequence with one or more amino acid mutations, substitutions, deletions or additions compared to SEQ ID NO: 1.

In some embodiments, the third sequence comprises a sequence encoding a human RPGR ORF15 polypeptide. In some embodiments, the third sequence comprises a sequence having at least 75% identity with SEQ ID NO: 2. In some embodiments, the third sequence comprises a sequence having at least 80% identity with SEQ ID NO: 2. In some embodiments, the third sequence comprises a sequence having at least 85% identity with SEQ ID NO: 2. In some embodiments, the third sequence comprises a sequence having at least 90% identity with SEQ ID NO: 2. In some embodiments, the third sequence comprises a sequence having at least 95% identity with SEQ ID NO: 2. In some embodiments, the third sequence comprises a sequence having at least 96% identity with SEQ ID NO: 2. In some embodiments, the third sequence comprises a sequence having at least 97% identity with SEQ ID NO: 2. In some embodiments, the third sequence comprises a sequence having at least 98% identity with SEQ ID NO: 2. In some embodiments, the third sequence comprises a sequence having at least 99% identity with SEQ ID NO: 2. In some embodiments, the third sequence comprises the sequence of SEQ ID NO: 2. In some embodiments, the third sequence comprises a sequence having one or more nucleotide mutations, substitutions, deletions or additions compared to SEQ ID NO: 2.

In some embodiments, the third sequence comprises a sequence encoding a human RPGR ORF15 polypeptide and is codon optimized. In some embodiments, the third sequence comprises a sequence having at least 75% identity with any one of SEQ ID NOs: 3-6. In some embodiments, the third sequence comprises a sequence having at least 80% identity with any one of SEQ ID NOs: 3-6. In some embodiments, the third sequence comprises a sequence having at least 85% identity with any one of SEQ ID NOs: 3-6. In some embodiments, the third sequence comprises a sequence having at least 90% identity with any one of SEQ ID NOs: 3-6. In some embodiments, the third sequence comprises a sequence having at least 95% identity with any one of SEQ ID NOs: 3-6. In some embodiments, the third sequence comprises a sequence having at least 96% identity with any one of SEQ ID NOs: 3-6. In some embodiments, the third sequence comprises a sequence having at least 97% identity with any one of SEQ ID NOs: 3-6. In some embodiments, the third sequence comprises a sequence having at least 98% identity with any one of SEQ ID NOs: 3-6. In some embodiments, the third sequence comprises a sequence having at least 99% identity with any one of SEQ ID NOs: 3-6. In some embodiments, the third sequence comprises the sequence of any one of SEQ ID NOs: 3-6. In some embodiments, the third sequence comprises a sequence having one or more nucleotide mutations, substitutions, deletions or additions compared to SEQ ID NOs: 3-6.

In some embodiments, the third sequence comprises a sequence having at least 75% identity with SEQ ID NO: 3. In some embodiments, the third sequence comprises a sequence having at least 80% identity with SEQ ID NO: 3. In some embodiments, the third sequence comprises a sequence having at least 85% identity with SEQ ID NO: 3. In some embodiments, the third sequence comprises a sequence having at least 90% identity with SEQ ID NO: 3. In some embodiments, the third sequence comprises a sequence having at least 95% identity with SEQ ID NO: 3. In some embodiments, the third sequence comprises a sequence having at least 96% identity with SEQ ID NO: 3. In some embodiments, the third sequence comprises a sequence having at least 97% identity with SEQ ID NO: 3. In some embodiments, the third sequence comprises a sequence having at least 98% identity with SEQ ID NO: 3. In some embodiments, the third sequence comprises a sequence having at least 99% identity with SEQ ID NO: 3. In some embodiments, the third sequence comprises the sequence of SEQ ID NO: 3. In some embodiments, the third sequence comprises a sequence having one or more nucleotide mutations, substitutions, deletions or additions compared to SEQ ID NO: 3.

In some embodiments, the third sequence comprises a sequence having at least 75% identity with SEQ ID NO: 4. In some embodiments, the third sequence comprises a sequence having at least 80% identity with SEQ ID NO: 4. In some embodiments, the third sequence comprises a sequence having at least 85% identity with SEQ ID NO: 4. In some embodiments, the third sequence comprises a sequence having at least 90% identity with SEQ ID NO: 4. In some embodiments, the third sequence comprises a sequence having at least 95% identity with SEQ ID NO: 4. In some embodiments, the third sequence comprises a sequence having at least 96% identity with SEQ ID NO: 4. In some embodiments, the third sequence comprises a sequence having at least 97% identity with SEQ ID NO: 4. In some embodiments, the third sequence comprises a sequence having at least 98% identity with SEQ ID NO: 4. In some embodiments, the third sequence comprises a sequence having at least 99% identity with SEQ ID NO: 4. In some embodiments, the third sequence comprises the sequence of SEQ ID NO: 4. In some embodiments, the third sequence comprises a sequence having one or more nucleotide mutations, substitutions, deletions or additions compared to SEQ ID NO: 4.

In some embodiments, the third sequence comprises a sequence having at least 75% identity with SEQ ID NO: 5. In some embodiments, the third sequence comprises a sequence having at least 80% identity with SEQ ID NO: 5. In some embodiments, the third sequence comprises a sequence having at least 85% identity with SEQ ID NO: 5. In some embodiments, the third sequence comprises a sequence having at least 90% identity with SEQ ID NO: 5. In some embodiments, the third sequence comprises a sequence having at least 95% identity with SEQ ID NO: 5. In some embodiments, the third sequence comprises a sequence having at least 96% identity with SEQ ID NO: 5. In some embodiments, the third sequence comprises a sequence having at least 97% identity with SEQ ID NO: 5. In some embodiments, the third sequence comprises a sequence having at least 98% identity with SEQ ID NO: 5. In some embodiments, the third sequence comprises a sequence having at least 99% identity with SEQ ID NO: 5. In some embodiments, the third sequence comprises the sequence of SEQ ID NO: 5. In some embodiments, the third sequence comprises a sequence having one or more nucleotide mutations, substitutions, deletions or additions compared to SEQ ID NO: 5.

In some embodiments, the third sequence comprises a sequence having at least 75% identity with SEQ ID NO: 6. In some embodiments, the third sequence comprises a sequence having at least 80% identity with SEQ ID NO: 6. In some embodiments, the third sequence comprises a sequence having at least 85% identity with SEQ ID NO: 6. In some embodiments, the third sequence comprises a sequence having at least 90% identity with SEQ ID NO: 6. In some embodiments, the third sequence comprises a sequence having at least 95% identity with SEQ ID NO: 6. In some embodiments, the third sequence comprises a sequence having at least 96% identity with SEQ ID NO: 6. In some embodiments, the third sequence comprises a sequence having at least 97% identity with SEQ ID NO: 6. In some embodiments, the third sequence comprises a sequence having at least 98% identity with SEQ ID NO: 6. In some embodiments, the third sequence comprises a sequence having at least 99% identity with SEQ ID NO: 6. In some embodiments, the third sequence comprises the sequence of SEQ ID NO: 6. In some embodiments, the third sequence comprises a sequence having one or more nucleotide mutations, substitutions, deletions or additions compared to SEQ ID NO: 6.

In some embodiments, the third sequence comprises a sequence having at least 75% identity with any sequence comprising any construct design of TABLE 2 and any sequence of SEQ ID NOs: 2-12. In some embodiments, the third sequence comprises a sequence having at least 80% identity with any sequence comprising any construct design of TABLE 2 and any sequence of SEQ ID NOs: 2-12. In some embodiments, the third sequence comprises a sequence having at least 85% identity with any sequence comprising any construct design of TABLE 2 and any sequence of SEQ ID NOs: 2-12. In some embodiments, the third sequence comprises a sequence having at least 90% identity with any sequence comprising any construct design of TABLE 2 and any sequence of SEQ ID NOs: 2-12. In some embodiments, the third sequence comprises a sequence having at least 95% identity with any sequence comprising any construct design of TABLE 2 and any sequence of SEQ ID NOs: 2-12. In some embodiments, the third sequence comprises a sequence having at least 96% identity with any sequence comprising any construct design of TABLE 2 and any sequence of SEQ ID NOs: 2-12. In some embodiments, the third sequence comprises a sequence having at least 97% identity with any sequence comprising any construct design of TABLE 2 and any sequence of SEQ ID NOs: 2-12. In some embodiments, the third sequence comprises a sequence having at least 98% identity with any sequence comprising any construct design of TABLE 2 and any sequence of SEQ ID NOs: 2-12. In some embodiments, the third sequence comprises a sequence having at least 99% identity with any sequence comprising any construct design of TABLE 2 and any sequence of SEQ ID NOs: 2-12. In some embodiments, the third sequence comprises the sequence of sequences comprising any construct design of TABLE 2 and any sequence of SEQ ID NOs: 2-12. In some embodiments, the third sequence comprises a sequence having one or more nucleotide mutations, substitutions, deletions or additions compared to sequences comprising any construct design of TABLE 2 and any sequence of SEQ ID NOs: 2-12.

In some embodiments, the third sequence is operably linked to a CMV, CAG, MNDU3, PGK, EF1a promoter or an eye-specific promoter. In some embodiments, the eye-specific promoter is a retinal pigment epithelial (RPE) cell-specific promoter. The RPE cell-specific promoters include, but are not limited to, an RPE65 gene promoter, a human retinal binding protein (CRALBP) promoter, a murine 11-cis retinol dehydrogenase (RDH) promoter, a Rhodopsin promoter, a Rhodopsin kinase (GRK1) promoter, a tissue inhibitor of metalloproteinase 3 (Timp3) promoter, a photoreceptor retinol binding protein promoter and a vitelliform macular dystrophy 2 promoter, or an interphotoreceptor retinoid-binding protein (IRBP) promoter.

In some embodiments, the third sequence is operably linked to the Rhodopsin kinase (GRK1) promoter. In some embodiments, the Rhodopsin kinase (GRK1) promoter comprises a sequence having at least 75% identity with any one of SEQ ID NOs: 7-8. In some embodiments, the Rhodopsin kinase (GRK1) promoter comprises a sequence having at least 80% identity with any one of SEQ ID NOs: 7-8. In some embodiments, the Rhodopsin kinase (GRK1) promoter comprises a sequence having at least 85% identity with any one of SEQ ID NOs: 7-8. In some embodiments, the Rhodopsin kinase (GRK1) promoter comprises a sequence having at least 90% identity with any one of SEQ ID NOs: 7-8. In some embodiments, the Rhodopsin kinase (GRK1) promoter comprises a sequence having at least 95% identity with any one of SEQ ID NOs: 7-8. In some embodiments, the Rhodopsin kinase (GRK1) promoter comprises a sequence having at least 96% identity with any one of SEQ ID NOs: 7-8. In some embodiments, the Rhodopsin kinase (GRK1) promoter comprises a sequence having at least 97% identity with any one of SEQ ID NOs: 7-8. In some embodiments, the Rhodopsin kinase (GRK1) promoter comprises a sequence having at least 98% identity with any one of SEQ ID NOs: 7-8. In some embodiments, the Rhodopsin kinase (GRK1) promoter comprises a sequence having at least 99% identity with any one of SEQ ID NOs: 7-8. In some embodiments, the Rhodopsin kinase (GRK1) promoter comprises the sequence of SEQ ID NOs: 7-8. In some embodiments, the Rhodopsin kinase (GRK1) promoter comprises a sequence having one or more nucleotide mutations, substitutions, deletions or additions compared to SEQ ID NOs: 7-8.

In some embodiments, the Rhodopsin kinase (GRK1) promoter comprises a sequence having at least 75% identity with SEQ ID NO: 7. In some embodiments, the Rhodopsin kinase (GRK1) promoter comprises a sequence having at least 80% identity with SEQ ID NO: 7. In some embodiments, the Rhodopsin kinase (GRK1) promoter comprises a sequence having at least 85% identity with SEQ ID NO: 7. In some embodiments, the Rhodopsin kinase (GRK1) promoter comprises a sequence having at least 90% identity with SEQ ID NO: 7. In some embodiments, the Rhodopsin kinase (GRK1) promoter comprises a sequence having at least 95% identity with SEQ ID NO: 7. In some embodiments, the Rhodopsin kinase (GRK1) promoter comprises a sequence having at least 96% identity with SEQ ID NO: 7. In some embodiments, the Rhodopsin kinase (GRK1) promoter comprises a sequence having at least 97% identity with SEQ ID NO: 7. In some embodiments, the Rhodopsin kinase (GRK1) promoter comprises a sequence having at least 98% identity with SEQ ID NO: 7. In some embodiments, the Rhodopsin kinase (GRK1) promoter comprises a sequence having at least 99% identity with SEQ ID NO: 7. In some embodiments, the Rhodopsin kinase (GRK1) promoter comprises the sequence of SEQ ID NO: 7. In some embodiments, the Rhodopsin kinase (GRK1) promoter comprises a sequence having one or more nucleotide mutations, substitutions, deletions or additions compared to SEQ ID NO: 7.

In some embodiments, the Rhodopsin kinase (GRK1) promoter comprises a sequence having at least 75% identity with SEQ ID NO: 8. In some embodiments, the Rhodopsin kinase (GRK1) promoter comprises a sequence having at least 80% identity with SEQ ID NO: 8. In some embodiments, the Rhodopsin kinase (GRK1) promoter comprises a sequence having at least 85% identity with SEQ ID NO: 8. In some embodiments, the Rhodopsin kinase (GRK1) promoter comprises a sequence having at least 90% identity with SEQ ID NO: 8. In some embodiments, the Rhodopsin kinase (GRK1) promoter comprises a sequence having at least 95% identity with SEQ ID NO: 8. In some embodiments, the Rhodopsin kinase (GRK1) promoter comprises a sequence having at least 96% identity with SEQ ID NO: 8. In some embodiments, the Rhodopsin kinase (GRK1) promoter comprises a sequence having at least 97% identity with SEQ ID NO: 8. In some embodiments, the Rhodopsin kinase (GRK1) promoter comprises a sequence having at least 98% identity with SEQ ID NO: 8. In some embodiments, the Rhodopsin kinase (GRK1) promoter comprises a sequence having at least 99% identity with SEQ ID NO: 8. In some embodiments, the Rhodopsin kinase (GRK1) promoter comprises the sequence of SEQ ID NO: 8. In some embodiments, the Rhodopsin kinase (GRK1) promoter comprises a sequence having one or more nucleotide mutations, substitutions, deletions or additions compared to SEQ ID NO: 8.

In some embodiments, the second polynucleotide further comprises other regulatory sequences, including but not limited to inverted terminal repeats (ITR), enhancers, splicing signals, polyadenylation signals, stuffer sequences, terminators, protein degradation signals, internal ribosome entry elements (IRES), or 2A sequences.

In some embodiments, the second polynucleotide further comprises an enhancer region. In some embodiments, the enhancer region includes an SV40 enhancer, an immediate early cytomegalovirus enhancer, an IRBP enhancer, and an enhancer derived from an immunoglobulin gene. In some embodiments, the enhancer region is located upstream of the CMV, CAG, MNDU3, PGK, EF1a promoter. In some embodiments, the enhancer is located upstream of the eye-specific promoter. In some embodiments, the enhancer region is located downstream of the CMV, CAG, MNDU3, PGK, EF1a promoter. In some embodiments, the enhancer is located downstream of the eye-specific promoter.

In some embodiments, the second polynucleotide further comprises an inverted terminal repeat (ITR). In some embodiments, the second polynucleotide comprises at least one inverted terminal repeat (ITR). In some embodiments, the second polynucleotide comprises two inverted terminal repeats (ITR). In some embodiments, the two ITRs are the same. In some embodiments, the two ITRs are different. In some embodiments, the inverted terminal repeat (ITR) is an ITR derived from AAV. In some embodiments, the ITR may be derived from AAV1, AAV2, AAV2 variant (e.g., AAV2.7m8, AAV2(quad Y-F), or AAV2tYF), AAV3, (including AAV3A and 3B), AAV4, AAV5, AAV6, AAV7, AAV8, AAV9, AAV10, AAV11, AAV12, AAV13, AAV-Rh10, AAV-Rh74, AAV-2i8 and any other known ITRs of AAVs. In some embodiments, the ITR may have one or more base mutations, insertions or deletions, compared to the one derived from AAV1, AAV2, AAV2 variant (e.g., AAV2.7m8, AAV2(quad Y-F), or AAV2tYF), AAV3, (including AAV3A and 3B), AAV4, AAV5, AAV6, AAV7, AAV8, AAV9, AAV10, AAV11, AAV12, AAV13, AAV-Rh10, AAV-Rh74, AAV-2i8 and any other known wild-type ITRs of AAVs, wherein the ITR retain the desired terminal repeat function, such as target gene replication, virus packaging, viral genome integration, or any combination thereof. In some cases, the ITR sequence is an AAV2 sequence. In some cases, the ITR sequence is an AAV2 variant (e.g., AAV2.7m8, AAV2(quad Y-F), or AAV2tYF) sequence. In some cases, the first polypeptide comprises an AAV5 sequence.

In some embodiments, the second polynucleotide further comprises one or more stuffer sequences. In some embodiments, the stuffer sequence is located upstream of the CMV, CAG, MNDU3, PGK, EF1a promoter sequence. In some embodiments, the stuffer sequence is located downstream of the CMV, CAG, MNDU3, PGK, EF1a promoter sequence. In some embodiments, the stuffer sequence is located upstream of the eye-specific promoter. In some embodiments, the stuffer sequence is located downstream of the eye-specific promoter. In some embodiments, the stuffer sequence is located at the 5' end of the 5' ITR sequence. In some embodiments, the stuffer sequence is located at the 3' end of the 5' ITR sequence. In some embodiments, the stuffer sequence is located at the 5' end of the 3' ITR sequence. In some embodiments, the stuffer sequence is located at the 5' end of the 3' ITR sequence. In some embodiments, the stuffer sequence is located at the 3'end of the 3'ITR sequence In some embodiments, the length of the stuffing sequence may be about 0.1 kb-5 kb, such as but not limited to 0.1 kb, 0.2 kb, 0.3 kb, 0.4 kb, 0.5 kb, 0.6 kb, 0.7 kb, 0.8 kb, 0.9 kb, 1 kb, 1.1 kb, 1.2 kb, 1.3 kb, 1.4 kb, 1.5 kb, 1.6 kb, 1.7 kb, 1.8 kb, 1.9 kb, 2 kb, 2.1 kb, 2.2 kb, 2.3 kb, 2.4 kb, 2.5 kb, 2.6 kb, 2.7 kb, 2.8 kb, 2.9 kb, 3 kb, 3.1 kb, 3.2 kb, 3.3 kb, 3.4 kb, 3.5 kb, 3.6 kb, 3.7 kb, 3.8 kb, 3.9 kb, 4.0 kb, 4.1 kb, 4.2 kb, 4.3 kb, 4.4 kb, 4.5 kb, 4.6 kb, 4.7 kb, 4.8 kb, 4.9 kb or 5.0 kb.

In some embodiments, the second polynucleotide further comprises a fourth sequence encoding another therapeutic protein. In some embodiments, the therapeutic protein is selected from the group consisting of RPGR Interacting Protein 1 (RPGRIP1), RPGR Interacting Protein 1-like protein (RPGRIP1L), structure maintenance protein 1 (SMC1), structure maintenance protein 3 (SMC3), Whirlin, phosphodiesterase δ (PDEδ), and Ras-related proteins in brain 8 (RAB8)

In some embodiments, the fourth sequence and the third sequence are connected by a sequence encoding a linker. In some embodiments, the linker is a cleavable linker. In some embodiments, the cleavable linker comprises the sequence of the 2A peptide. In some embodiments, the 2A peptide may be selected from 2A peptides derived from Aphthorvirus or Cardiovirus, such as foot-and-mouth disease virus (FMDV), Equine rhinitis A virus (ERAV), *Thosea asigna* virus (TaV) or porcine teschovirus (PTV-1). In some embodiments, the sequence encoding the linker further comprises a promoter sequence. In some embodiments, the promoter is an FMDV promoter.

In some embodiments, the composition may comprise an intron. In some embodiments, the intron comprises a sequence having at least 75% identity with SEQ ID NO: 13. In some embodiments, the intron comprises a sequence having at least 80% identity with SEQ ID NO: 13. In some embodiments, the intron comprises a sequence having at least 85% identity with SEQ ID NO: 13. In some embodiments, the intron comprises a sequence having at least 90% identity with SEQ ID NO: 13. In some embodiments, the intron comprises a sequence having at least 95% identity with SEQ ID NO: 13. In some embodiments, the intron comprises a sequence having at least 96% identity with SEQ ID NO: 13. In some embodiments, the intron comprises a sequence having at least 97% identity with SEQ ID NO: 13. In some embodiments, the intron comprises a sequence having at least 98% identity with SEQ ID NO: 13. In some embodiments, the intron comprises a sequence having at least 99% identity with SEQ ID NO: 13. In some embodiments, the intron comprises the sequence of SEQ ID NO: 13. In some embodiments, the intron comprises a sequence having one or more nucleotide mutations, substitutions, deletions or additions compared to SEQ ID NO: 13.

Recombinant AAV Virus Particles

In another aspect, the present disclosure provides a recombinant adeno-associated virus (rAAV) particle prepared by introducing the composition of the present disclosure into mammalian cells. In some embodiments, the mammalian cell is HEK293 cell or its derivatives such as 293T cells.

In some embodiments, the method includes, but is not limited to, electroporation, calcium phosphate precipitation, liposome-mediated transfection. In some embodiments, the composition is transfected into the 293T cells with a helper plasmid. In some embodiments, the 293T cells are used to produce the rAAV virus particles.

In another aspect, the present disclosure provides a recombinant adeno-associated virus (rAAV) particle prepared by introducing the composition of the present disclosure into insect cells and a method for preparing a recombinant adeno-associated virus (rAAV) particle by introducing the composition of the present disclosure into insect cells. In some embodiments, the insect cells are Sf9 cells.

In some embodiments, the composition of the present disclosure may be delivered into the insect cell by any method known in the art. In some embodiments, the method includes, but is not limited to, electroporation, calcium phosphate precipitation, liposome-mediated transfection, and/or infection. In some embodiments, the composition is infected into the insect cell. In some embodiments, the composition is stably transfected into the insect cell.

In some embodiments, the method for preparing recombinant AAV virus particles may comprise generating bacmid DNA and/or baculovirus. In some embodiments, the method for preparing recombinant AAV virus particles may comprise generating RPGR expression sequence bacmid DNA. In some embodiments, the method for preparing recombinant AAV virus particles may comprise generating rAAV cap expression sequence bacmid DNA. In some embodiments, the method for preparing recombinant AAV virus particles may comprise transfecting a host cell with the bacmid DNA to produce baculoviruses. In some embodiments, the method for preparing recombinant AAV virus particles may comprise transfecting a host cell with the RPGR expression sequence bacmid DNA to produce baculoviruses. In some embodiments, the method for preparing recombinant AAV virus particles may comprise transfecting a host cell with the rAAV cap expression sequence bacmid DNA to produce baculoviruses. In some embodiments, the method for preparing recombinant AAV virus particles may further comprise mixing the two baculoviruses to infect a host cell (such as the Sf9 cell) to obtain packaged rAAV/RPGR-optimized virus particles of the present disclosure.

In some embodiments, the method for preparing recombinant AAV virus particles may comprise (1) generating RPGR expression sequence bacmid DNA, (2) generating rAAV cap expression sequence bacmid DNA, (3) transfecting a host cell with the bacmid DNA to produce baculoviruses, (4) transfecting a host cell with the RPGR expression sequence bacmid DNA to produce baculoviruses, (5) transfecting a host cell with the rAAV cap expression sequence bacmid DNA to produce baculoviruses, and (6) mixing the two baculoviruses to infect a host cell (such as the Sf9 cell) to obtain packaged rAAV/RPGR-optimized virus particles of the present disclosure.

In some embodiments, the method for preparing recombinant AAV virus particles may comprise generating bacmid DNA and/or baculovirus. In some embodiments, the method for preparing recombinant AAV virus particles may comprise generating RPGR ORF15 expression sequence bacmid DNA. In some embodiments, the method for preparing recombinant AAV virus particles may comprise generating rAAV cap expression sequence bacmid DNA. In some embodiments, the method for preparing recombinant AAV virus particles may comprise transfecting a host cell with the bacmid DNA to produce baculoviruses. In some embodiments, the method for preparing recombinant AAV virus particles may comprise transfecting a host cell with the RPGR ORF15 expression sequence bacmid DNA to produce baculoviruses. In some embodiments, the method for preparing recombinant AAV virus particles may comprise transfecting a host cell with the rAAV cap expression sequence bacmid DNA to produce baculoviruses. In some embodiments, the method for preparing recombinant AAV virus particles may further comprise mixing the two baculoviruses to infect a host cell (such as the Sf9 cell) to obtain packaged rAAV/RPGR ORF15-optimized virus particles of the present disclosure.

In some embodiments, the method for preparing recombinant AAV virus particles may comprise (1) generating RPGR ORF15 expression sequence bacmid DNA, (2) generating rAAV cap expression sequence bacmid DNA, (3) transfecting a host cell with the bacmid DNA to produce baculoviruses, (4) transfecting a host cell with the RPGR ORF15 expression sequence bacmid DNA to produce baculoviruses, (5) transfecting a host cell with the rAAV cap expression sequence bacmid DNA to produce baculoviruses, and (6) mixing the two baculoviruses to infect a host cell (such as the Sf9 cell) to obtain packaged rAAV/RPGR ORF15-optimized virus particles of the present disclosure.

If necessary, in some cases, the rAAV virus particles can be isolated and purified from the insect cells according to conventional methods known to those skilled in the art. For example, the rAAV can be purified using centrifugation, HPLC, hydrophobic interaction chromatography (HIC), anion exchange chromatography, cation exchange chromatography, size exclusion chromatography, ultrafiltration, gel electrophoresis, affinity chromatography, other purification techniques, or any combinations thereof.

Systems

In another aspect, the present disclosure provides a system for treating XLRP in a subject in need thereof, which comprises the rAAV particles of the present disclosure and a pharmaceutically acceptable carrier or excipient.

As used herein, "pharmaceutically or therapeutically acceptable carrier or excipient" refers to a carrier medium that does not interfere with the effectiveness of the biological activity of the active ingredient and is non-toxic to the host or patient. The type of carrier used in the pharmaceutical formulation will depend on the method of administration of the therapeutic compound. Many methods of preparing pharmaceutical compositions for multiple routes of administration are well known in the art. "Pharmaceutically acceptable ophthalmic carrier" refers to a pharmaceutically acceptable carrier or excipient that can be used to directly or indirectly deliver the rAAV virus particles of the present disclosure to the eye, on or near the eye.

In some embodiments of the present disclosure, the system is prepared by dissolving the rAAV virus particles of the present disclosure in a suitable solvent. Suitable solvents include, but are not limited to, water, salt solutions (e.g., NaCl), buffer solutions, ointments, gels, or other solvents. In certain embodiments, the solvent is sterile.

The aqueous solution and diluent for suspension used in the preparation of eye drops may include distilled water or physiological saline. Various additives may be included in the eye drops, ophthalmic gels and/or ophthalmic ointments. These additives may include additional ingredients, additives or carriers suitable for contact with or around the eyes without excessive toxicity, incompatibility, instability, irritation, or allergy. Additives such as solvents, bases, cosolvents, suspending agents, thickeners, emulsifiers, stabilizers, buffers, isotonicity regulators, pH regulators, chelating agents, soothing agents, preservatives, flavoring agents, flavoring agents, coloring agents, excipients, binders, lubricants, surfactants, absorption promoters, dispersants, or solubilizers.

For example, the eye drops can be formulated by dissolving rAAV virus particles in sterile water with surfactants dissolved and optionally adding appropriate pharmaceutical additives such as preservatives, stabilizers, buffers, antioxidants, and viscosity modifiers.

For example, a buffer is added to maintain a constant pH for the buffer, and the buffer may include a pharmaceutically acceptable buffer, such as borate buffer, citrate buffer, tartrate buffer, phosphate buffer, acetate buffer or Tris-HCl buffer (containing tris(hydroxymethyl)aminomethane and HCl).

In addition to the buffer, an isotonic agent that is isotonic with tear fluid may be added to the eye. Isotonic agents include, but are not limited to, sugars, such as dextrose, glucose, sucrose, and fructose; sugar alcohols, such as mannitol and sorbitol; polyhydric alcohols, such as glycerol, polyethylene glycol, and propylene glycol; and salts, such as chlorinated sodium, sodium citrate, benzalkonium chloride, ephedrine chloride, potassium chloride, procaine chloride, chloramphenicol, and sodium succinate. The isotonic agent is added in such an amount that the osmotic pressure of the eye drops is equal to the osmotic pressure of the tear fluid.

Preservatives may be added to maintain the integrity of the eye drops and/or ophthalmic ointment. Examples of preservatives include, but are not limited to, sorbic acid, benzalkonium chloride, benzododecinium bromide, parabens, chlorobutanol, benzyl alcohol, phenethyl alcohol, benzene disodium oleate, sorbic acid, polyquaternium-1 or other reagents known to those skilled in the art.

In some embodiments, thickeners are used to increase the viscosity of ophthalmic formulations such as eye drops, ophthalmic gels, and/or ophthalmic ointments. Thickeners that can be used include, but are not limited to, glycerin, polyethylene glycol, carboxymethyl cellulose, and carboxyvinyl polymers.

In addition to the reagents thereof, in some embodiments, it is also desirable to use additional reagents, including but not limited to stabilizers such as sodium sulfite, sodium carbonate and propylene glycol; antioxidants, such as ascorbic acid, sodium ascorbate, butylated hydroxytoluene (BHT), butylated hydroxyanisole (BHA), tocopherol, sodium thiosulfate; and/or chelating agents, such as ethylenediaminetetraacetic acid (EDTA), ethylene glycol-bis-(2-aminoethyl)-N, N,N,N-tetraacetic acid (EGTA) and sodium citrate Eye drops, ophthalmic gels, ophthalmic ointments, or any combination thereof may be prepared by aseptic operations, or alternatively, sterilized at a suitable stage of preparation. For example, a sterile pharmaceutical composition can be prepared by aseptically mixing sterile ingredients. Alternatively, the sterile pharmaceutical composition can be prepared by first mixing the ingredients and then sterilizing the final formulation. Sterilization methods can include, but are not limited to, heat sterilization, radiation, and filtration Ophthalmic ointment (eye ointment) can be aseptically prepared by mixing the active ingredients into a base for preparing ophthalmic ointment, and then formulating it into a pharmaceutical preparation by any method known in the art. Examples of typical bases used for eye ointments are petrolatum, jelene 50, plastibase, and polyethylene glycol. In addition, surfactants can be added to increase hydrophilicity A variety of effective methods for the controlled release of active agents can be used. See, for example, Wagh V. D., Inamdar B., Samanta M. K., "Polymers used in ocular dosage form and drug delivery systems." Asian J Pharm 2, 2008, 12-17 and references cited therein, the contents of which are incorporated herein by reference. Special consideration is given to the use of polymers (for example, cellulose derivatives such as hydroxypropyl methylcellulose (HPMC) and hydroxypropyl cellulose (HPC), poly(acrylic acid) (PAA), polyacrylates, cyclodextrins, and natural gums, polyorthoesters (POE) and mucoadhesive polymers); semi-solids, such as gels, membranes, and other inserts; resins, such as ion exchange resins; iontophoretic delivery; and colloidal particles, such as microspheres and nanoparticles.

The rAAV virus particles of the present disclosure can also be provided in combination with other therapeutic agents. In some embodiments, the drug or composition of the present disclosure may be co-formulated with other active agents, including but not limited to anti-infective agents, antibiotics, antiviral agents, antifungal agents, antiprotozoal agents, anti-inflammatory agents, antiallergic agents (including antihistamines), artificial tear vasoconstrictors, vasodilators, local anesthetics, analgesics, intraocular pressure lowering agents, immunomodulators, antioxidants, vitamins and minerals, enzyme inhibitors or alternative proteases and peptidase, or cytokine inhibitor.

In various embodiments, the drugs or compositions of the present disclosure may also be provided in combination with ocular therapeutics, wherein the ocular therapeutics can comprise Acular (ketorolac tromethamine ophthalmic solution) 0.5%, Acuvail (ketorolac tromethamine), AK-Con-A (naphazoline eye drops), Akten (lidocaine hydrochloride), Alamast, Alphagan (brimonidine), Alrex, Astepro (azelastine hydrochloride nasal spray), AzaSite (azithromycin), Bepreve (bepotastine besilate ophthalmic solution), Besivance (besifloxacin eye Use suspension), Betaxon, BSS sterile lavage solution, Cosopt, Durezol (difluprednate), Eylea (afibercept), Lotemax, Lucentis (Ranibizumab), Lumigan (Bimatoprost eye Solution), Macugen (pegantanib), Ocuflox (ofloxacin ophthalmic solution) 0.3%, OcuHist, Ozurdex (dexamethasone), Quixin (levofloxacin), Rescula (unoprostone isopropyl ophthalmic solution) 0.15%, Restasis (cyclosporin ophthalmic emulsion), Salagen tablets, Travatan (travoprost ophthalmic solution), Valcyte (valganciclovir hydrochloride), Trifluorothymidine (Viroptic), Vistide (Cidofovir), Visudyne (Verteporfin for injection), Vitrasert implant, Fomivirson injection, ZADITOR, Zioptan (tafluprost ophthalmic solution), Zirgan (Ganciclovir ophthalmic gel), Zymaxid (Gatifloxacin ophthalmic solution), Atropine, Flurbiprofen, Physostimine, Azopt, Gentamicin, Pilocarpine (Proparacaine), bacitracin, hypromellose eye drops (Goniosol), polymyxin B, povidone iodine (Betadine), gramicidin, prednisolone, betaolol, Humorsol, proparacaine, betalol eye drops (Betoptic), Hylartin, Propine, Brinzolamide, Hypertonic NaCl, Puralube, BSS, Indocycanine Green, Rose Bengal, Carbachol, Itraconazole, Sodium Hyaluronate, Cefazolin, Latanoprost, Suprofen, Celluvisc, Mannitol, Oxytetracycline, Chloramphenicol, Metazolamide, Timolol, Ciloxan, Miconazole, Tobramycin, Cypro Floxacin, Miostat, Triamcinolone, Cosopt, Muro 128, Trifluridine, Demecarium, Neomycin, Toppicamide, Dexamethasone, Metazolamide (Neptazane), Trusopt, Dipiforin, Ocuflox, Vidarabine, Dorzolamide, Ofloxacin, Vira-A, Epinephrine, Oxotetracycline, Trifluorothymidine, Fluorescein, Phenylephrine, or Xalatan.

Examples of the drug may include anti-angiogenic agents such as angiostatin, anecort acetate, thrombospondin, VEGF receptor tyrosine kinase inhibitor, and anti-vascular endothelial growth factor (anti-VEGF) Drugs such as ranibizumab and bevacizumab, pegaptanib, sunitinib, and sorafenib, and any number of known antibacterial drugs. Small molecules and transcription inhibitors of angiogenesis; various known ophthalmological drugs, including: glaucoma agents, such as adrenergic antagonists, including, for example, β-blockers such as acetbutolol, attenolol, bisoprolol, carvedilol, asmolol, labetalol, nadolol, pembrolol, pindolol, propranolol, metenolol, betaxolol, carteolol, levobetaxolol, levobunolol, and timolol; adrenergic agonists or sympathomimetic nerve drugs such as epinephrine, dipivefrin, clonidine, araclonidine, and brimonidine; parasympathetic drugs or cholinergic receptor agonists such as pilocarpine, carbachol, phospholine iodine, physostigmine, salicylic acid, acetylcholine chloride, eserine, diiso propyl fluorophosphate, demecarium bromide; muscarinic; carbonic anhydrase inhibitor agents, including topical and/or systemic agents, such as acetozolamide, brinzolamide, dorzolamide, and methazolamide, ethoxzolamide, diamox, and dichlorphenamide; mydriatic-cycloplegic agent such as atropine, cyclopentolate, succinylcholine, homatropine, phenylephrine, scopolamine and tropicamide; prostaglandins such as prostaglandin F2α, anti-prostaglandins, prostaglandin precursors, or prostaglandin analog agents such as bimatoprost, latanoprost, travoprost, and unoprostone Additional drug examples may also include anti-inflammatory drugs, including, for example, glucocorticoids and corticosteroids, such as betamethasone, cortisone, dexamethasone, dexamethasone 21-phosphate, methylprednisolone, prednisolone 21-phosphate, prednisolone acetate, prednisolone, fluorometholone, loteprednol, metoxysone, fluocinolone acetate, triamcinolone acetonide, triamcinolone, triamcinolone acetate, beclomethasone, budesonide, flunisolide, fluorometholone, fluticasone, fludrocortisone, hydrocortisone, hydrocortisone acetate, loteprednol, rimexolone and non-steroidal antibiotics inflammatory drugs include, for example, aspirin, diclofenac (diclofenac), flurbiprofen, ibuprofen, bromfenac (bromfenac), nepafenac, and ketorolac, salicylate, indomethacin, naxopren, piroxicam and nabumetone diflunisal, etodolac, fenoprofen, flurbiprofen, indomethacin, ketoprofen, clofenamic acid, mefenamic acid, meloxicam, nabumetone, oxaprazine (oxaprozin), piroxicam, salicylate, sulindac and tolmetin; COX-2 inhibitors such as celecoxib, rofecoxib and valdecoxib; anti-infective or antimicrobial agent such as antibiotics include, for example, tetracycline, chlortetracycline, bacitracin, neomycin, polymyxin, gramicidin, cephalexin, oxytetracycline, chloramphenicol, rifampicin, ciprofloxacin, tobramycin, gentamicin, erythromycin, penicillin, sulfa drugs, sulfadiazine, sulfacetamide, sulfamethizole, sulfisoxazole, nitrofurazone, sodium propionate, aminoglycosides such as gentamicin, tobramycin, amikacin and streptomycin; fluoroquinolones such as ciprofloxacin, gatifloxacin, levofloxacin, moxifloxacin, norfloxacin, ofloxacin; bacitracin, erythroblast element, fusidic acid, neomycin, polymyxin b, gramicidin, trimethoprim and sulfacetamide; antifungal agents such as amphotericin b, caspofungin, clotrimazole, fluconazole, itraconazole, ketoconazole, voriconazole, terbinafine, nystatin and miconazole; anti-malarial agents such as chloroquine, atovaquinone, mefloquine, primaquine, quinidine and quinine; anti-mycobacterial agents such as ethambutol, isoniazid, pyrazine amides, rifampicin and rifabutin; antiparasitic agents such as albendazole, mebendazole, thiobendazole, diazotide suppository, pyrantel, atovaquone, iodoquinaol, ivermectin, paromomycin, praziquantel, and trimatrexate.

Methods

In another aspect, the present application provides a method for treating X-linked retinitis pigmentosa (XLRP), which comprises administering a therapeutically effective amount of the system of the present disclosure to a subject in need thereof.

In some embodiments, the system can be administered to the subject by any suitable method known in the art. In some embodiments, the system may be administered locally to the eye, for example, subconjunctival, retrobulbar, periocular, subretinal, suprachoroidal, or intraocular administration.

In some embodiments, the system comprising the rAAV virus particles is provided in a therapeutically effective amount that achieves the desired biological effect at a medically acceptable level of toxicity. The dosage can vary according to the route of administration and the severity of the disease. The dosage can also be adjusted according to the weight, age, sex, degree of symptoms of each patient to be treated, or any combinations thereof. The precise dosage and route of administration will ultimately be determined by the treating doctor or veterinarian. Understandably, the dosage may need to be routinely changed according to the age and weight of the patient and the severity of the condition to be treated In some embodiments, the therapeutically effective amount is generally about 1×10^5 to 1×10^13 rAAV virus particles. In some embodiments, the therapeutically effective amount is generally about 1×10^6 to 1×10^12 rAAV virus particles. In some embodiments, the therapeutically effective amount is generally about 1×10^7 to 1×10^12 rAAV virus particles. In some embodiments, the therapeutically effective amount is generally about 1×10^8 to 1×10^12 rAAV virus particles. In some embodiments, the therapeutically effective amount is generally about 1×10^9 to 1×10^12 rAAV virus particles. In some embodiments, the therapeutically effective amount is generally about 1×10^10 to 1×10^12 rAAV virus particles.

In some embodiments, the volume delivered is about 0.005 millimeter (mL)-0.5 mL per eye. In some embodiments, the volume delivered is about 0.05 mL-0.5 mL per eye. In some embodiments, the volume delivered is about 0.1 mL-0.5 mL per eye. In some embodiments, the volume delivered is about 0.2 mL-0.5 mL per eye. In some embodiments, the delivered volume is from about 0.01 mL-1 mL per eye. In some embodiments, the volume delivered is about 0.15 mL-0.5 mL per eye. In some embodiments, the volume delivered is about 0.25 mL-0.5 mL per eye. In some embodiments, the volume delivered is about 0.3 mL-0.5 mL per eye. In some embodiments, the volume delivered is about 0.35 mL-0.5 mL per eye. In some embodiments, the volume delivered is about 0.4 mL-0.5 mL per eye. In some embodiments, the volume delivered is about 0.45 mL-0.5 mL per eye. In some embodiments, the volume delivered is about 0.005 mL per eye. In some embodiments, the volume delivered is about 0.05 mL per eye. In some embodiments, the volume delivered is about 0.1 mL per eye. In some embodiments, the volume delivered is about 0.15 mL per eye. In some embodiments, the volume delivered is about 0.2 mL per eye. In some embodiments, the volume delivered is about 0.25 mL per eye. In some embodiments, the volume delivered is about 0.3 mL per eye. In some embodiments, the volume delivered is about 0.35 mL per eye. In some embodiments, the volume delivered is about 0.4 mL per eye. In some embodiments, the volume delivered is about 0.45 mL per eye. In some embodiments, the volume delivered is about 0.5 mL per eye. In some embodiments, the volume delivered is about 0.005 mL-0.05 mL per eye. In some embodiments, the volume delivered is about 0.005 mL-0.1 mL per eye. In some embodiments, the volume delivered is about 0.005 mL-0.15 mL per eye. In some embodiments, the volume delivered is about 0.005 mL-0.2 mL per eye. In some embodiments, the volume delivered is about 0.005 mL-0.25 mL per eye. In some embodiments, the volume delivered is about 0.005 mL-0.3 mL per eye. In some embodiments, the volume delivered is about 0.005 mL-0.35 mL per eye. In some embodiments, the volume delivered is about 0.005 mL-0.4 mL per eye. In some embodiments, the volume delivered is about 0.005 mL-0.45 mL per eye.

In some embodiments, the frequency of administration may be applied at least once a day, including 2, 3, 4, or 5 times a day. In some embodiments, the treatment can last for 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 60 days, 70 days, 80 days, 90 days, 100 days, 150 days, 200 days, 250 days, 300 days, 400 days, 500 days, 750 days, 1000 days, or more than 1000 days.

Kits

In another aspect, the present disclosure provides a kit for treating XLRP, which includes the system and instructions of the present disclosure. In some embodiments, the instructions are used to teach a method of administering the system to treat XLRP.

In some embodiments, the kit further comprises a container. In some embodiments, the container is configured to deliver the system described herein. In some embodiments, the container includes vials, droppers, bottles, tubes, and syringes. In some embodiments, the container is a dropper used to apply the system. In some embodiments, the container is a syringe used to administer the system.

EMBODIMENTS

1. A composition comprising:
   (i) a first polynucleotide, wherein said first polynucleotide comprises a first sequence operably linked to a first promoter and a second sequence operably linked to a second promoter, said first sequence encoding an adeno-associated virus (AAV) capsid protein, said second sequence encoding an AAV rep protein, said first promoter and said second promoter are suitable for expression in insect cells, and
   (ii) a second polynucleotide, wherein said second polynucleotide comprises a third sequence operably linked to a CMV promoter, a CAG promoter, a MNDU3 promoter, a PGK promoter, a EF1a promoter, or an eye-specific promoter, and wherein said third sequence encodes a retinitis pigmentosa GTPase regulator (RPGR) polypeptide.
2. The composition of embodiment 1, wherein said third sequence encodes an RPGR ORF15 polypeptide.
3. The composition of embodiment 1 or 2, wherein said third sequence is codon optimized.
4. The composition of any one of embodiments 1-3, wherein said third sequence comprises SEQ ID NO: 2 or a sequence having at least 90% identity to SEQ ID NO: 2.
5. The composition of any one of embodiments 1-3, wherein said third sequence comprises any one of SEQ ID NOs: 3-6 or a sequence having at least 90% identity to any one of SEQ ID NOs: 3-6.
6. The composition of embodiment 5, wherein said third sequence comprises SEQ ID NO: 3 or a sequence having at least 90% identity to SEQ ID NO: 3.
7. The composition of embodiment 5, wherein said third sequence comprises SEQ ID NO: 4 or a sequence having at least 90% identity to SEQ ID NO: 4.
8. The composition of embodiment 5, wherein said third sequence comprises SEQ ID NO: 5 or a sequence having at least 90% identity to SEQ ID NO: 5.
9. The composition of embodiment 5, wherein said third sequence comprises SEQ ID NO: 6 or a sequence having at least 90% identity to SEQ ID NO: 6.
10. The composition of any one of embodiments 1-9, wherein said insect cells are Sf9 cells.
11. The composition of any one of embodiments 1-10, wherein said first promoter or said second promoter is a p10 promoter or a polh promoter.
12. The composition of embodiment 11, wherein said first promoter or said second promoter is said p10 promoter.
13. The composition of embodiment 11, wherein said first promoter or said second promoter is said polh promoter.
14. The composition of any one of embodiments 1-13, wherein said eye-specific promoter is selected from the group consisting of a RPE 65 gene promoter, a cellular retinaldehyde-binding protein (CRALBP), a murine 11-cis-retinol dehydrogenase (RDH) promoter, a rhodopsin promoter, a Rhodopsin kinase (GRK1) promoter, a tissue inhibitor of metalloproteinase-3 (TIMP3) promoter, a photoreceptor retinol binding protein promoter, a vitelliform macular dystrophy 2 promoter, and an Interphotoreceptor retinoid-binding protein (IRBP) promoter.
15. The composition of embodiment 14, wherein said Rhodopsin kinase (GRK1) promoter comprises any one of SEQ ID NOs: 7-8 or a sequence having at least 90% identity to any one of SEQ ID NOs: 7-8.
16. The composition of embodiment 15, wherein said Rhodopsin kinase (GRK1) promoter comprises SEQ ID NO: 7 or a sequence having at least 90% identity to SEQ ID NO: 7.
17. The composition of embodiment 15, wherein said Rhodopsin kinase (GRK1) promoter comprises SEQ ID NO: 8 or a sequence having at least 90% identity to SEQ ID NO: 8.
18. The composition of any one of embodiments 1-17, wherein the 3' end of said first sequence further comprises a poly A sequence.
19. The composition of any one of embodiments 1-18, wherein the 3' end of said second sequence further comprises a poly A sequence.

20. The composition of any one of embodiments 1-19, wherein said first sequence and said second sequence are connected by a sequence encoding a linker.
21. The composition of embodiment 20, wherein said linker is a cleavable linker.
22. The composition of embodiment 20, wherein said linker comprises a sequence encoding a 2A peptide.
23. The composition of embodiment 20, wherein said sequence encoding said linker further comprises a promoter.
24. The composition of embodiment 23, wherein said promoter is a FMDV promoter.
25. The composition of any one of embodiments 1-24, wherein said the 3' end of said third sequence further comprises a poly A sequence.
26. The composition of any one of embodiments 18-25, wherein said poly A sequence comprises any one of SEQ ID NOs: 9-12 or a sequence having at least 90% identity to any one of SEQ ID NOs: 9-12.
27. The composition of embodiment 26, wherein said poly A sequence comprises SEQ ID NO: 9 or a sequence having at least 90% identity to SEQ ID NO: 9.
28. The composition of embodiment 26, wherein said poly A sequence comprises SEQ ID NO: 10 or a sequence having at least 90% identity to SEQ ID NO: 10.
29. The composition of embodiment 26, wherein said poly A sequence comprises SEQ ID NO: 11 or a sequence having at least 90% identity to SEQ ID NO: 11.
30. The composition of embodiment 26, wherein said poly A sequence comprises SEQ ID NO: 12 or a sequence having at least 90% identity to SEQ ID NO: 12.
31. The composition of any one of embodiments 1-30, wherein said second polynucleotide further comprises a stuffer sequence.
32. The composition of any one of embodiments 1-31, wherein said second polynucleotide further comprises an inverted terminal repeat (ITR) sequence.
33. The composition of embodiment 32, wherein said Inverted terminal repeat (ITR) sequence is an adeno-associated virus (AAV) serotype 2 ITR sequence.
34. The composition of any one of embodiments 1-33, wherein said second polynucleotide further comprises a fourth sequence encoding a therapeutic protein.
35. The composition of embodiment 34, wherein said therapeutic protein is selected from the group consisting of: RPGRIP1, RPGRIP1L, SMC1, SMC3, Whirlin, PDEδ, and RAB8.
36. The composition of embodiment 34, wherein said third sequence and said fourth sequence are connected by a sequence encoding a linker.
37. The composition of embodiment 36, wherein said linker is a cleavable linker.
38. The composition of embodiment 36, wherein said linker comprises a sequence encoding a 2A peptide.
39. The composition of any one of embodiments 1-38, further comprising an intron sequence.
40. The composition of embodiment 39, wherein said intron sequence comprises SEQ ID NO: 13 or a sequence having at least 90% identity to SEQ ID NO: 13.
41. The composition of any one of embodiments 1-40, wherein said first polynucleotide comprises an adeno-associated virus (AAV) serotype 5 sequence.
42. A recombinant adeno-associated virus (rAAV) particle prepared by transfecting the composition of any one of embodiments 1-41 into an insect cell.
43. The recombinant adeno-associated virus (rAAV) particle of embodiment 42, wherein said insect cell is a Sf9 cell.
44. A system for treating X linked retinitis pigmentosa, comprising said recombinant adeno-associated virus (rAAV) particle of embodiment 42 or 43 and a pharmaceutically acceptable carrier.
45. A method for treating X linked retinitis pigmentosa, comprising administering to said subject in need thereof the system of embodiment 44.
46. A kit comprising said system of embodiment 44 and instructions.

Some embodiments of the present disclosure are further illustrated by the following examples, which should not be construed as limiting. Those skilled in the art will understand that the techniques disclosed in the following examples represent techniques that the inventors have found to work well in the implementation of the embodiments of the present disclosure described herein, and can therefore be considered to constitute a useful tool for implementing these embodiments. Preferred way. However, based on the present disclosure, those skilled in the art will understand that without departing from the spirit and scope of the present disclosure, many changes can be made in the specific embodiments disclosed herein, and the same or similar results can still be obtained.

EXAMPLES

These examples are provided for illustrative purposes only and not to limit the scope of the claims provided herein.

Example 1—Design of Recombinant AAV Constructs

The cap and rep coding sequences derived from AAV5 and AAV2, respectively, together with their corresponding promoters were synthesized and cloned into modified pFastBac1 to obtain the first polynucleotide comprising the coding sequences of cap and rep proteins.

The nucleotide sequence encoding the RPGR ORF15 polypeptide shown in SEQ ID NO: 1 and their corresponding promoters were cloned into modified pFastBac1 to obtain the second polynucleotide comprising the coding sequence of RPGR ORF15.

Codon optimization was used to optimize the expression of RPGR ORF15.

To codon optimize the RPGR ORF15 sequence, various expression constructs listed in TABLE 2 were created.

TABLE 2

Designs of Codon-optimized RPGR ORF15 Expression Constructs

| ID | Construct design |
|---|---|
| PA001 | 5'-GRK1S-RPGR ORF15 co1-bGHpA-3' |
| PA002 | 5'-GRK1L-SV40 intron-RPGR ORF15 co2-SV40pA-3' |
| PA003 | 5'-GRK1S-RPGR ORF15 co3-bGHpA-3' |
| PA004 | 5'-GRK1S-SV40 intron-RPGR ORF15 co3-SV40pA-3' |
| PA005 | 5'-GRK1S-SV40 intron-RPGR ORF15 co3-rbGlobpA-3' |
| PA006 | 5'-GRK1S-SV40 intron-RPGR ORF15 co3-hGHpA-3' |
| PA007 | 5'-GRK1L-RPGR ORF15 co3-bGHpA-3' |
| PA008 | 5'-GRK1L-SV40 intron-RPGR ORF15 co3-SV40pA-3' |
| PA009 | 5'-GRK1L-SV40 intron-RPGR ORF15 co3-rbGlobpA-3' |
| PA010 | 5'-GRK1L-SV40 intron-RPGR ORF15 co3-hGHpA-3' |

TABLE 2-continued

Designs of Codon-optimized RPGR ORF15 Expression Constructs

| ID | Construct design |
|---|---|
| PA011 | 5'-GRK1S-RPGR ORF15 co4-bGHpA-3' |
| PA012 | 5'-GRK1S-SV40 intron-RPGR ORF15 co4-SV40pA-3' |
| PA013 | 5'-GRK1S-SV40 intron-RPGR ORF15 co4-rbGlobpA-3' |
| PA014 | 5'-GRK1S-SV40 intron-RPGR ORF15 co4-hGHpA-3' |
| PA122 | 5'-GRK1L-RPGR ORF15 co4-bGHpA-3' |
| PA123 | 5'-GRK1L-SV40 intron-RPGR ORF15 co4-SV40pA-3' |
| PA124 | 5'-GRK1L-SV40 intron-RPGR ORF15 co4-rbGlobpA-3' |
| PA125 | 5'-GRK1L-SV40 intron-RPGR ORF15 co4-hGHpA-3' |

co: codon-optimized; GRK1S: GRK1 short promoter; GRK1L: GRK1 long promoter.

Four codon-optimized RPGR ORF15 cDNA sequences were created (RPGR ORF15 co1-co4; SEQ ID NOs: 3-6). The constructs contained either the long form Rhodopsin kinase 1 (GRK1L; SEQ ID NO: 7) promoter or short form GRK1 promoter (GRK1S; SEQ ID NO: 8). Various constructs also contained different poly A sequences—bGHpA (SEQ ID NO: 9), SV40 pA (SEQ ID NO: 10), rbGlobpA (SEQ ID NO: 11) and hGHpA (SEQ ID NO: 12)—and the SV40 intron sequence (SEQ ID NO: 13).

Figure 1B:
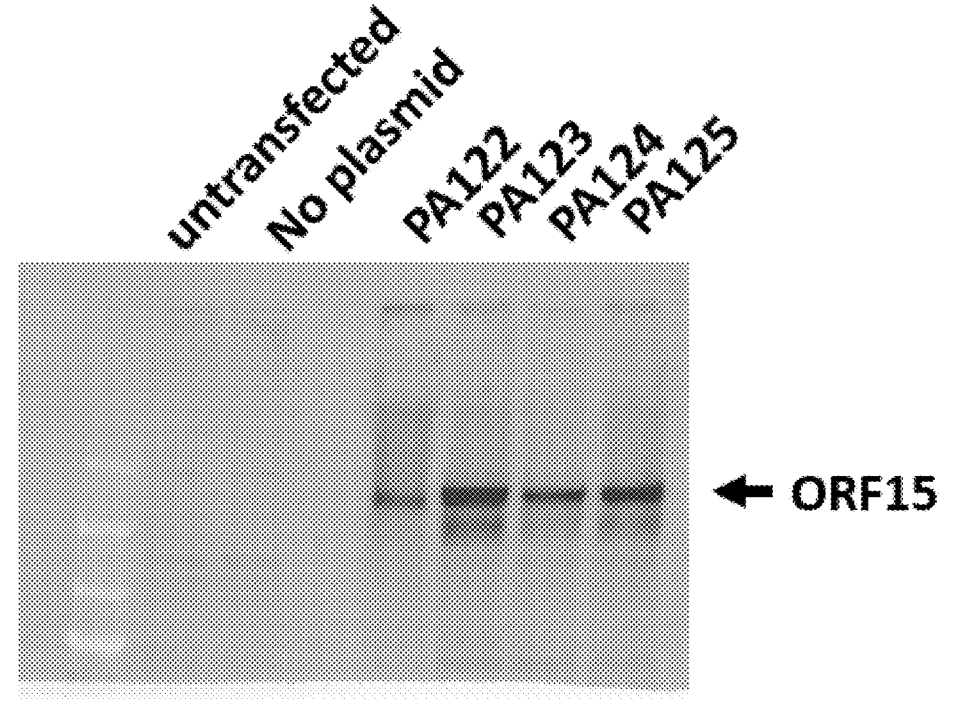

Example 2—Robust Expression of the Codon-Optimized RPGR ORF15 Constructs in Vitro To determine the expression intensity of designed constructs, $2\times10^5$ HEK293T cells were seeded in a 24-well plate and cultured overnight. 0.5 microgram (μg) of each expression construct plasmid was mixed with 1.5 microliter (μL) Mirus TransT-VirusGEN® Transfection Reagent per well in 50 μL Opti-Mem medium (DNA (μg): Mirus reagent (μl)= 1:3). After 48 hours, the expression of RPGR ORF15 protein was detected by a Western blotting. As shown in FIGS. 1A-B, all constructs expressed the recombinant RPGR ORF15 proteins in high levels. These proteins were also glutamylated, suggesting that they had undergone endogenous post-translational modification, similar to that of a wild type RPGR ORF15 protein.

The expression of the recombinant RPGR ORF15 protein from the codon-optimized cDNA construct was analyzed.

These data suggest that the codon-optimized RPGR ORF15 cDNA constructs can express a high level of functional recombinant proteins in vitro.

Example 3—Preparation of Recombinant AAV Virus Particles

The AAV particles were produced by the bac to AAV technology. Specifically, two bacmids containing Rep-Cap and transgene expression cassette, respectively, were generated, and baculoviruses for these two bacmids were then produced. The rAAV was produced by infecting both Rep-Cap and transgene baculoviruses in Sf9 cells. The recombinant AAV2/5/RPGR ORF15 virus particles were isolated and purified using gradient ultracentrifugation or affinity columns.

Example 4—Functional Rpgr Orf15 Proteins in the Eye

The functional properties of the RPGR ORF15 proteins expressed from the constructs in TABLE 2 in the eye were evaluated using a RPGR knockout mouse model.

The mice were injected with selected rAAV5 viral particles of Example 3 according to the schedule listed in TABLE 3 using bilateral subretinal injection.

TABLE 3

Injection Schedule of the RPGR knockout mice

| Construct injected | Number of eyes injected |
|---|---|
| PA001 | 10 |
| PA002 | 26 |
| PA004 | 14 |
| PA011 | 22 |
| PA012 | 22 |
| PA014 | 22 |
| Vehicle: formulation buffer (PBS + 0.001% F-68) | 14 |

For each injection other than the negative control (Vehicle), ~1×10^9 viral particles were injected into each eye.

Figure 2A:
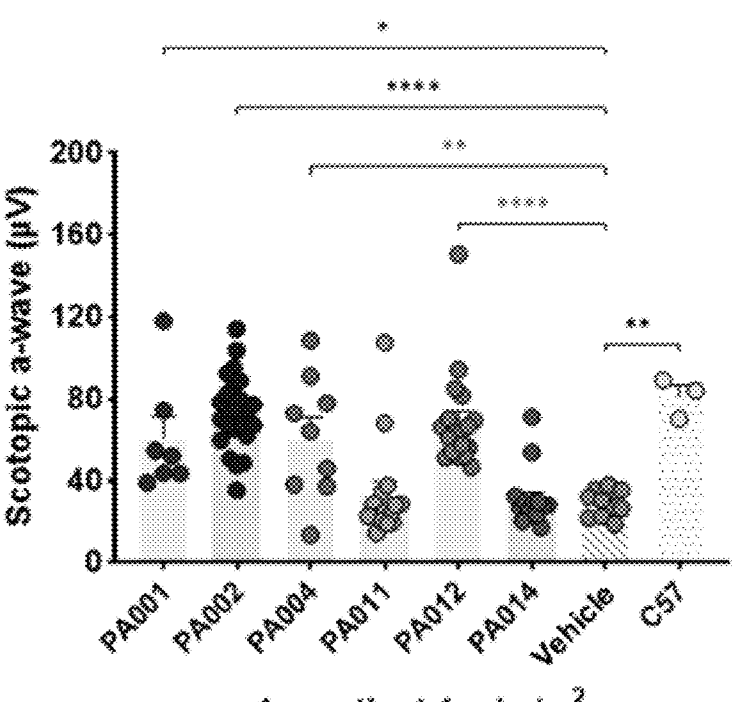
FIGS. 2A-C show that the recombinant RPGR ORF15 protein expressed from the codon-optimized constructs are functional in vivo in the eye.
Figure 2B:
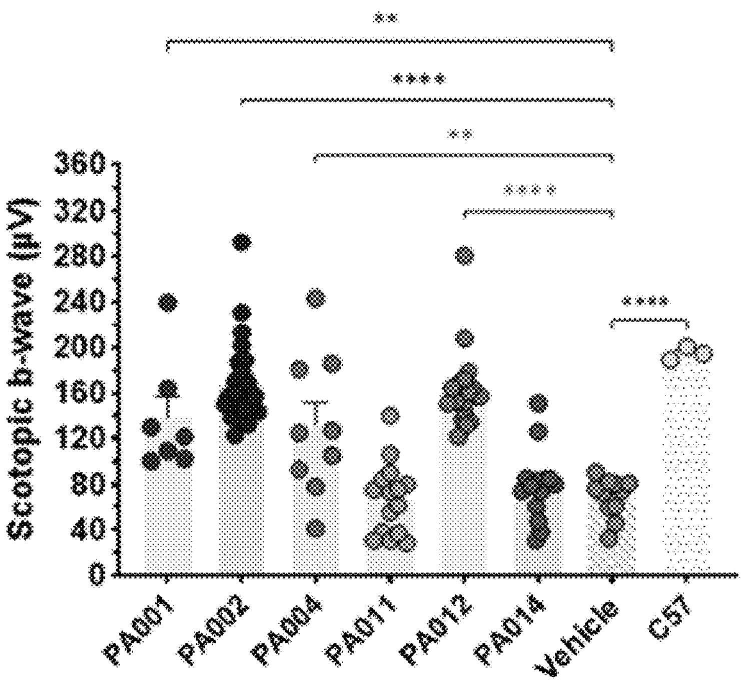
Figure 2C:
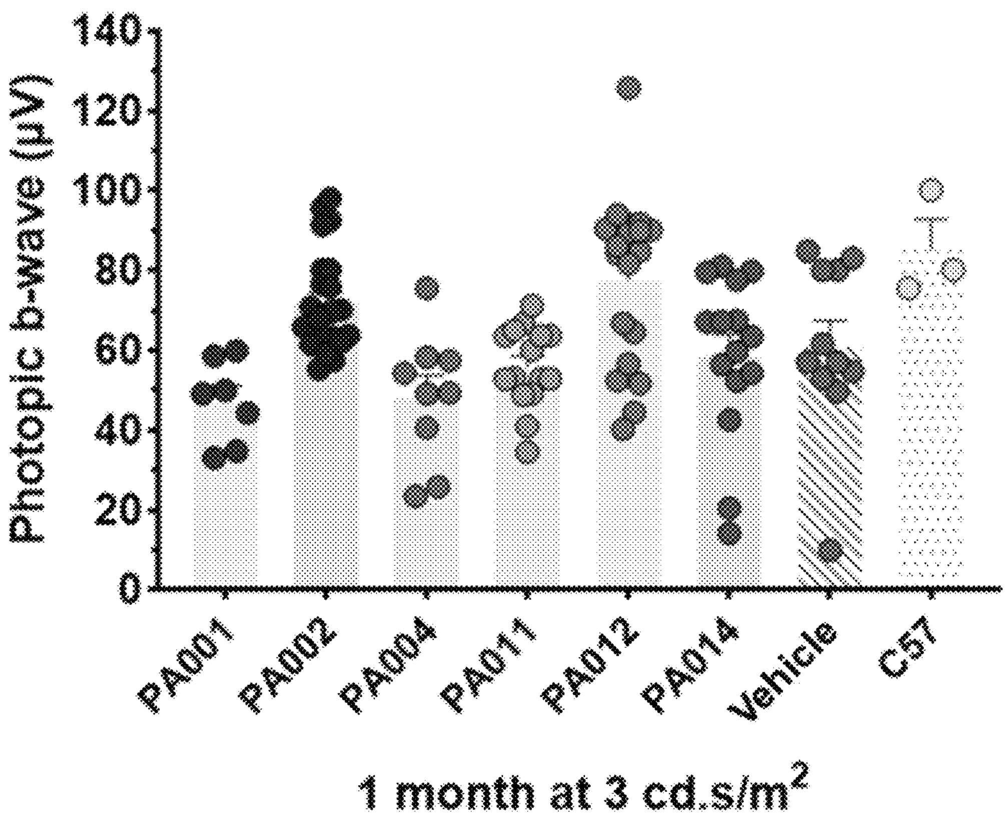

Rolling injections were carried out as mice became available from breeding. The functional properties of the recombinant RPGR ORF15 protein were tested in a visual test using electroretinography (ERG). Wild type mice (C57 mice) was used as a positive control. The first analysis was carried out one month after the injection. As shown in FIGS. 2A-2B, all the constructs except for PA014 were able to statistically significantly rescue the scotopic A-wave and B-wave defect of the RPGR knockout mice. The phenotypes of the mice injected PA002, PA004, and PA012 were similar to that of the positive control mice. Further, the mice injected with PA002 and PA012 also rescued the photopic B-wave phenotype of the RPGR knockout mice, as shown in FIG. 2C.

These data show that the RPGR ORF15 proteins expressed from AAV vectors are functional in vivo.

Example 5—Design and Cloning of Recombinant Aav Vectors

The cap and rep coding sequences and their corresponding promoters derived from AAV2 are cloned into the baculovirus plasmid vector to obtain the first polynucleotide of the present disclosure comprising the coding sequences of the cap and rep proteins.

The nucleotide sequence encoding the green fluorescent protein (GFP) and the nucleotide sequence encoding the RPGR ORF15 polypeptide shown in SEQ ID NO: 1 and their corresponding promoters are cloned into the baculovirus plasmid vector to obtain the second polynucleotide comprising the coding sequence of GFP and RPGR ORF15.

Example 6—Delivery and Expression of Reporter Genes in the Mouse Eyes

In this embodiment, mice are divided into an experimental group and a control group. The purified rAAV2/GFP virus particles obtained by methods described Example 3 and PBS are injected into the eyes of the experimental group and the control group, respectively. After a period of time, the fluorescence expression in the mouse retinal pigment epithelial cells is evaluated.

Compared to the control group, green fluorescence is observed in the retina pigment of the mice in the experimental group. This result shows that the rAAV vector comprising the first polynucleotide containing the GFP coding sequence in this disclosure can be successfully packaged into the rAAV2/GFP viral particles for the delivery, and the delivered GFP coding sequence can be successfully expressed in the mouse retinal pigment epithelium.

Example 7—Delivery and Expression of RPGR ORF15 in Mice

The mice are divided into two groups (control and experiment), wherein the control group and the experimental group are injected intraocularly with rAAV2/GFP and rAAV2/RPGR ORF15 virus particles purified by methods described in Example 3. The eyes of mice are evaluated after the injection. The result shows that GFP can be successfully expressed in the mouse retinal pigment epithelium, indicating that the recombinant RPGR ORF15 coding sequence can be expressed on the retina.

Example 8—the Efficacy of the Composition of the Application In Vivo

A two-arm clinical trial are carried out using the control and system containing rAAV2/RPGR ORF15 virus particles described in this disclosure to test the effectiveness of the system described in this application.

The effectiveness of other virus particles can also be tested using this example.

While preferred embodiments of the present disclosure have been shown and described herein, it will be obvious to those skilled in the art that such embodiments are provided by way of example only. It is not intended that the disclosure be limited by the specific examples provided within the specification. While the disclosure has been described with reference to the aforementioned specification, the descriptions and illustrations of the embodiments herein are not meant to be construed in a limiting sense. Numerous variations, changes, and substitutions will now occur to those skilled in the art without departing from the disclosure. Furthermore, it shall be understood that all aspects of the disclosure are not limited to the specific depictions, configurations or relative proportions set forth herein which depend upon a variety of conditions and variables. It should be understood that various alternatives to the embodiments of the disclosure described herein may be employed in practicing the disclosure. It is therefore contemplated that the disclosure shall also cover any such alternatives, modifications, variations or equivalents. It is intended that the following claims define the scope of the disclosure and that methods and structures within the scope of these claims and their equivalents be covered thereby.

SEQUENCE LISTING

| SEQ ID NO | Sequence | Description |
|---|---|---|
| SEQ ID NO: 1 | MREPEELMPDSGAVFTFGKSKFAENNPGKFWFKNDVPVH<br>LSCGDEHSAVVTGNNKLYMFGSNNWGQLGLGSKSAISKP<br>TCVKALKPEKVKLAACGRNHTLVSTEGGNVYATGGNNEG<br>QLGLGDTEERNTFHVISFFTSEHKIKQLSAGSNTSAALTED<br>GRLFMWGDNSEGQIGLKNVSNVCVPQQVTIGKPVSWISCG<br>YYHSAFVTTDGELYVFGEPENGKLGLPNQLLGNHRTPQLV<br>SEIPEKVIQVACGGEHTVVLTENAVYTFGLGQFGQLGLGT<br>FLFETSEPKVIENIRDQTISYISCGENHTALITDIGLMYTFGD<br>GRHGKLGLGLENFTNHFIPTLCSNFLRFIVKLVACGGCHM<br>VVFAAPHRGVAKEIEFDEINDTCLSVATFLPYSSLTSGNVL<br>QRTLSARMRRRERERSPDSFSMRRTLPPIEGTLGLSACFLP<br>NSVFPRCSERNLQESVLSEQDLMQPEEPDYLLDEMTKEAEI<br>DNSSTVESLGETTDILNMTHIMSLNSNEKSLKLSPVQKQKK<br>QQTIGELTQDTALTENDDSDEYEEMSEMKEGKACKQHVS<br>QGIFMTQPATTIEAFSDEEVEIPEEKEGAEDSKGNGIEEQEV<br>EANEENVKVHGGRKEKTEILSDDLTDKAEVSEGKAKSVG<br>EAEDGPEGRGDGTCEEGSSGAEHWQDEEREKGEKDKGRG<br>EMERPGEGEKELAEKEEWKKRDGEEQEQKEREQGHQKER<br>NQEMEEGGEEEHGEGEEEEGDREEEEEKEGEGKEEGEGEE<br>VEGEREKEEGERKKEERAGKEEKGEEEGDQGEGEEEETEG<br>RGEEKEEGGEVEGGEVEEGKGEREEEEEEGEGEEEEGEGE<br>EEEGEGEEEEGEGKGEEEGEEGEGEEEGEEGEGEGEEEEG<br>EGEGEEEGEGEGEEEEGEGEGEEEGEGEGEEEEGEGKGEE<br>EGEEGEGEGEEEEGEGEGEDGEGEGEEEEGEWEGEEEEGE<br>GEGEEEGEGEGEEGEGEGEEEEGEGEGEEEEGEEEGEEEG<br>EGEEEGEGEGEEEEEEGEVEGEVEGEEGEGEGEEEEGEEEG<br>EEREKEGEGEENRRNREEEEEEEEGKYQETGEEENERQDGE<br>EYKKVSKIKGSVKYGKHKTYQKKSVTNTQGNGKEQRSK<br>MPVQSKRLLKNGPSGSKKFWNNVLPHYLELK | Human RPGR ORF15 protein sequence |
| SEQ ID NO: 2 | ATGAGGGAGCCGGAAGAGCTGATGCCCGATTCGGGTGC<br>TGTGTTTACATTTGGGAAAAGTAAATTTGCTGAAAATAA<br>TCCCGGTAAATTCTGGTTTAAAAATGATGTCCCTGTACA<br>TCTTTCATGTGGAGATGAACATTCTGCTGTTGTTACCGG<br>AAATAATAAACTTTACATGTTTGGCAGTAACAACTGGG<br>GTCAGTTAGGATTAGGATCAAAGTCAGCCATCAGCAAG<br>CCAACATGTGTCAAAGCTCTAAAACCTGAAAAAGTGAA<br>ATTAGCTGCCTGTGGAAGGAACCACACCCTGGTGTCAA<br>CAGAAGGAGGCAATGTATATGCAACTGGTGGAAATAAT<br>GAAGGACAGTTGGGGCTTGGTGACACCGAAGAAAGAA<br>ACACTTTTCATGTAATTAGCTTTTTTACATCCGAGCATA<br>AGATTAAGCAGCTGTCTGCTGGATCTAATACTTCAGCTG<br>CCCTAACTGAGGATGGAAGACTTTTTATGTGGGGTGAC<br>AATTCCGAAGGGCAAATTGGTTTAAAAAATGTAAGTAA<br>TGTCTGTGTCCCTCAGCAAGTGACCATTGGGAAACCTGT<br>CTCCTGGATCTCTTGTGGATATTACCATTCAGCTTTTGTA | Nucleotide sequence encoding wildtype human RPGRORF 15 |

-continued

SEQUENCE LISTING

| SEQ ID NO | Sequence | Description |
|---|---|---|
| | ACAACAGATGGTGAGCTATATGTGTTTGGAGAACCTGA | |
| | GAATGGGAAGTTAGGTCTTCCCAATCAGCTCCTGGGCA | |
| | ATCACAGAACACCCCAGCTGGTGTCTGAAATTCCGGAG | |
| | AAGGTGATCCAAGTAGCCTGTGGTGGAGAGCATACTGT | |
| | GGTTCTCACGGAGAATGCTGTGTATACCTTTGGGCTGGG | |
| | ACAATTTGGTCAGCTGGGTCTTGGCACTTTTCTTTTTGA | |
| | AACTTCAGAACCCAAAGTCATTGAGAATATTAGGGATC | |
| | AAACAATAAGTTATATTTCTTGTGGAGAAAATCACACA | |
| | GCTTTGATAACAGATATCGGCCTTATGTATACTTTTGGA | |
| | GATGGTCGCCACGGAAAATTAGGACTTGGACTGGAGAA | |
| | TTTTACCAATCACTTCATTCCTACTTTGTGCTCTAATTTT | |
| | TTGAGGTTTATAGTTAAATTGGTTGCTTGTGGTGGATGT | |
| | CACATGGTAGTTTTTGCTGCTCCTCATCGTGGTGTGGCA | |
| | AAAGAAATTGAATTCGATGAAATAAATGATACTTGCTT | |
| | ATCTGTGGCGACTTTTCTGCCGTATAGCAGTTTAACCTC | |
| | AGGAAATGTACTGCAGAGGACTCTATCAGCACGTATGC | |
| | GGCGAAGAGAGAGGGAGAGGTCTCCAGATTCTTTTTCA | |
| | ATGAGGAGAACACTACCTCCAATAGAAGGGACTCTTGG | |
| | CCTTTCTGCTTGTTTTCTCCCCAATTCAGTCTTTCCACGA | |
| | TGTTCTGAGAGAAACCTCCAAGAGAGTGTCTTATCTGAA | |
| | CAGGACCTCATGCAGCCAGAGGAACCAGATTATTTGCT | |
| | AGATGAAATGACCAAAGAAGCAGAGATAGATAATTCTT | |
| | CAACTGTAGAAAGCCTTGGAGAAACTACTGATATCTTA | |
| | AACATGACACACATCATGAGCCTGAATTCCAATGAAAA | |
| | GTCATTAAAATTATCACCAGTTCAGAAACAAAAGAAAC | |
| | AACAAACAATTGGGGAACTGACGCAGGATACAGCTCTT | |
| | ACTGAAAACGATGATAGTGATGAATATGAAGAAATGTC | |
| | AGAAATGAAAGAAGGGAAAGCATGTAAACAACATGTG | |
| | TCACAAGGGATTTTCATGACGCAGCCAGCTACGACTATC | |
| | GAAGCATTTTCAGATGAGGAAGTAGAGATCCCAGAGGA | |
| | GAAGGAAGGAGCAGAGGATTCAAAAGGAAATGGAATA | |
| | GAGGAGCAAGAGGTAGAAGCAAATGAGGAAAATGTGA | |
| | AGGTGCATGGAGGAAGAAAGGAGAAAACAGAGATCCT | |
| | ATCAGATGACCTTACAGACAAAGCAGAGGTGAGTGAAG | |
| | GCAAGGCAAAATCAGTGGGAGAAGCAGAGGATGGGCC | |
| | TGAAGGTAGAGGGGATGGAACCTGTGAGGAAGGTAGTT | |
| | CAGGAGCAGAACACTGGCAAGATGAGGAGAGGGAGAA | |
| | GGGGGAGAAAGACAAGGGTAGAGGAGAAATGGAGAGG | |
| | CCAGGAGAGGGAGAGAAGGAACTAGCAGAGAAGGAAG | |
| | AATGGAAGAAGAGGGATGGGGAAGAGCAGGAGCAAAA | |
| | GGAGAGGGAGCAGGGCCATCAGAAGGAAAGAAACCAA | |
| | GAGATGGAGGAGGGAGGGGAGGAGGAGCATGGAGAAG | |
| | GAGAAGAAGAGGAGGGAGACAGAGAAGAGGAAGAAG | |
| | AGAAGGAGGGAGAAGGGAAAGAGGAAGGAGAAGGGG | |
| | AAGAAGTGGAGGGAGAACGTGAAAAGGAGGAAGGAGA | |
| | GAGGAAAAAGGAGGAAAGAGCGGGGAAGGAGGAGAA | |
| | AGGAGAGGAAGAAGGAGACCAAGGAGAGGGGGAAGA | |
| | GGAGGAAACAGAGGGGAGAGGGGAGGAAAAAGAGGA | |
| | GGGAGGGGAAGTAGAGGGAGGGGAAGTAGAGGAGGGG | |
| | AAAGGAGAGAGGGAAGAGGAAGAGGAGGAGGGTGAG | |
| | GGGGAAGAGGAGGAAGGGGAGGGGGAAGAGGAGGAA | |
| | GGGGAGGGGGAAGAGGAGGAAGGAGAAGGGAAAGGG | |
| | GAGGAAGAAGGGGAAGAAGGAGAAGGGGAGGAAGAA | |
| | GGGGAGGAAGGAGAAGGGGAGGGGGAAGAGGAGGAA | |
| | GGAGAAGGGGAGGGAGAAGAGGAAGGAGAAGGGGAG | |
| | GGAGAAGAGGAGGAAGGAGAAGGGGAGGGAGAAGAG | |
| | GAAGGAGAAGGGGAGGGAGAAGAGGAGGAAGGAGAA | |
| | GGGAAAGGGGAGGAGGAAGGAGAGGAAGGAGAAGGG | |
| | GAGGGGGAAGAGGAGGAAGGAGAAGGGGAAGGGGAG | |
| | GATGGAGAAGGGGAGGGGGAAGAGGAGGAAGGAGAAT | |
| | GGGAGGGGGAAGAGGAGGAAGGAGAAGGGGAGGGGG | |
| | AAGAGGAAGGAGAAGGGGAAGGGGAGGAAGGAGAAG | |
| | GGGAGGGGGAAGAGGAGGAAGGAGAAGGGGAGGGGG | |
| | AAGAGGAGGAAGGGGAAGAAGAAGGGGAGGAAGAAG | |
| | GAGAGGGAGAGGAAGAAGGGGAGGGAGAAGGGGAGG | |
| | AAGAAGAGGAAGGGGAAGTGGAAGGGGAGGTGGAAGG | |
| | GGAGGAAGGAGAGGGGGAAGGAGAGGAAGAGGAAGG | |
| | AGAGGAGGAAGGAGAAGAAAGGGAAAAGGAGGGGGA | |
| | AGGAGAAGAAAACAGGAGGAACAGAGAAGAGGAGGA | |
| | GGAAGAAGAGGGGAAGTATCAGGAGACAGGCGAAGAA | |
| | GAGAATGAAAGGCAGGATGGAGAGGAGTACAAAAAAG | |
| | TGAGCAAAATAAAAGGATCTGTGAAATATGGCAAACAT | |
| | AAAACATATCAAAAAAAGTCAGTTACTAACACACAGGG | |
| | AAATGGGAAAGAGCAGAGGTCCAAAATGCCAGTCCAGT | |
| | CAAAACGACTTTTAAAAAACGGGCCATCAGGTTCCAAA | |

-continued

SEQUENCE LISTING

| SEQ ID NO | Sequence | Description |
|---|---|---|
| | AAGTTCTGGAATAATGTATTACCACATTACTTGGAATTG<br>AAGTAA | |
| SEQ ID NO: 3 | ATGAGAGAGCCAGAGGAGCTGATGCCAGACAGTGGAG<br>CAGTGTTTACATTCGGAAAATCTAAGTTCGCTGAAAATA<br>ACCCAGGAAAGTTCTGGTTTAAAAACGACGTGCCCGTC<br>CACCTGTCTTGTGGCGATGAGCATAGTGCCGTGGTCACT<br>GGGAACAATAAGCTGTACATGTTCGGGTCCAACAACTG<br>GGGACAGCTGGGGCTGGGATCCAAATCTGCTATCTCTA<br>AGCCAACCTGCGTGAAGGCACTGAAACCCGAGAAGGTC<br>AAACTGGCCGCTTGTGGCAGAAACCACACTCTGGTGAG<br>CACCGAGGGCGGGAATGTCTATGCCACCGGAGGCAACA<br>ATGAGGGACAGCTGGGACTGGGGGACACTGAGGAAAG<br>GAATACCTTTCACGTGATCTCCTTCTTTACATCTGAGCA<br>TAAGATCAAGCAGCTGAGCGCTGGCTCCAACACATCTG<br>CAGCCCTGACTGAGGACGGGCGCCTGTTCATGTGGGGA<br>GATAATTCAGAGGGCCAGATTGGGCTGAAAAACGTGAG<br>CAATGTGTGCGTCCCTCAGCAGGTGACCATCGGAAAGC<br>CAGTCAGTTGGATTTCATGTGGCTACTATCATAGCGCCT<br>TCGTGACCACAGATGGCGAGCTGTACGTCTTTGGGGAG<br>CCCGAAAACGGAAAACTGGGCCTGCCTAACCAGCTGCT<br>GGGCAATCACCGGACACCCCAGCTGGTGTCCGAGATCC<br>CTGAAAAAGTGATCCAGGTCGCCTGCGGGGGAGAGCAT<br>ACAGTGGTCCTGACTGAGAATGCTGTGTATACCTTCGGA<br>CTGGGCCAGTTTGGCCAGCTGGGGCTGGGAACCTTCCTG<br>TTTGAGACATCCGAACCAAAAGTGATCGAGAACATTCG<br>CGACCAGACTATCAGCTACATTTCCTGCGGAGAGAATC<br>ACACCGCACTGATCACAGACATTGGCCTGATGTATACCT<br>TTGGCGATGGACGACACGGGAAGCTGGGACTGGGACTG<br>GAGAACTTCACTAATCATTTTATCCCCACCCTGTGTTCT<br>AACTTCCTGCGGTTCATCGTGAAACTGGTCGCTTGCGGC<br>GGGTGTCACATGGTGGTCTTCGCTGCACCTCATAGGGGC<br>GTGGCTAAGGAGATCGAATTTGACGAGATTAACGATAC<br>ATGCCTGAGCGTGGCAACTTTCCTGCCATACAGCTCCCT<br>GACTTCTGGCAATGTGCTGCAGAGAACCCTGAGTGCAA<br>GGATGCGGAGAAGGGAGAGGGAACGCTCTCCTGACAGT<br>TTCTCAATGCGACGAACCCTGCCACCTATCGAGGGAAC<br>ACTGGGACTGAGTGCCTGCTTCCTGCCTAACTCAGTGTT<br>TCCACGATGTAGCGAGCGGAATCTGCAGGAGTCTGTCC<br>TGAGTGAGCAGGATCTGATGCAGCCAGAGGAACCCGAC<br>TACCTGCTGGATGAGATGACCAAGGAGGCCGAAATCGA<br>CAACTCTAGTACAGTGGAGTCCCTGGGCGAGACTACCG<br>ATATCCTGAATATGACACACATTATGTCACTGAACAGCA<br>ATGAGAAGAGTCTGAAACTGTCACCAGTGCAGAAGCAG<br>AAGAAACAGCAGACTATTGGCGAGCTGACTCAGGACAC<br>CGCCCTGACAGAGAACGACGATAGCGATGAGTATGAGG<br>AAATGTCCGAGATGAAGGAAGGCAAAGCTTGTAAGCAG<br>CATGTCAGTCAGGGGATCTTCATGACACAGCCAGCCAC<br>AACTATTGAGGCTTTTTCAGACGAGGAAGTGGAGATCC<br>CCGAGGAAAAAGAGGGCGCAGAAGATTCCAAGGGGAA<br>TGGAATTGAGGAACAGGAGGTGGAAGCCAACGAGGAA<br>AATGTGAAAGTCCACGGAGGCAGGAAGGAGAAAACAG<br>AAATCCTGTCTGACGATCTGACTGACAAGGCCGAGGTG<br>TCCGAAGGCAAGGCAAAATCTGTCGGAGAGGCAGAAG<br>ACGGACCAGAGGGACGAGGGGATGGAACCTGCGAGGA<br>AGGCTCAAGCGGGGCTGAGCATTGGCAGGACGAGGAAC<br>GAGAGAAGGGCGAAAAGGATAAAGGCCGCGGGGAGAT<br>GGAACGACCTGGAGAGGGCGAAAAAGAGCTGGCAGAG<br>AAGGAGGAATGGAAGAAAAGGGACGGCGAGGAACAGG<br>AGCAGAAAGAAAGGGAGCAGGGCCACCAGAAGGAGCG<br>CAACCAGGAGATGGAAGAGGGCGGCGAGGAAGAGCAT<br>GGCGAGGGAGAAGAGGAAGAGGGCGATAGAGAAGAGG<br>AAGAGGAAAAAGAAGGCGAAGGGAAGGAGGAAGGAG<br>AGGGCGAGGAAGTGGAAGGCGAGAGGGAAAAGGAGGA<br>AGGAGAACGGAAGAAAGAGGAAAGAGCCGGCAAAGAG<br>GAAAAGGGCGAGGAAGAGGGCGATCAGGGCGAAGGCG<br>AGGAGGAAGAGACCGAGGGCCGCGGGGAAGAGAAAGA<br>GGAGGGAGGAGAGGTGGAGGGCGGAGAGGTCGAAGAG<br>GGAAAGGGCGAGCGCGAAGAGGAAGAGGAAGAGGGCG<br>AGGGCGAGGAAGAAGAGGGCGAGGGGGAAGAAGAGG<br>AGGGAGAGGGCGAAGAGGAAGAGGGGGAGGGAAAGG<br>GCGAAGAGGAAGGAGAGGAAGGGGAGGGAGAGGAAG<br>AGGGGGAGGAGGGCGAGGGGGAAGGCGAGGAGGAAG<br>AAGGAGAGGGGGAAGGCGAAGAGGAAGGCGAGGGGG<br>AAGGAGAGGAGGAAGAAGGGGAAGGCGAAGGCGAAG | Codon-optimized RPGR ORF15 coding sequence #1 |

-continued

SEQUENCE LISTING

| SEQ ID NO | Sequence | Description |
|---|---|---|
| | AGGAGGGAGAAGGAGAGGGGGAGGAAGAGGAAGGAG<br>AAGGGAAGGGCGAGGAGGAAGGCGAAGAGGGAGAGG<br>GGGAAGGCGAGGAAGAGGAAGGCGAGGGCGAAGGAGA<br>GGACGGCGAGGGCGAGGGAGAAGAGGAGGAAGGGGAA<br>TGGGAAGGCGAAGAAGAGGAAGGCGAAGGCGAAGGCG<br>AAGAAGAGGGCGAAGGGGAGGGCGAGGAGGGCGAAGG<br>CGAAGGGGAGGAAGAGGAAGGCGAAGGAGAAGGCGAG<br>GAAGAAGAGGGAGAGGAGGAAGGCGAGGAGGAAGGA<br>GAGGGGGAGGAGGAGGGAGAAGGCGAGGGCGAAGAA<br>GAAGAAGAGGGAGAAGTGGAGGGCGAAGTCGAGGGGG<br>AGGAGGGAGAAGGGGAAGGGGAGGAAGAAGAGGGCG<br>AAGAAGAAGGCGAGGAAAGAGAAAAAGAGGGAGAAG<br>GCGAGGAAAACCGGAGAAATAGGGAAGAGGAGGAAGA<br>GGAAGAGGGAAAGTACCAGGAGACAGGCGAAGAGGAA<br>AACGAGCGGCAGGATGGCGAGGAATATAAGAAAGTGA<br>GCAAGATCAAAGGATCCGTCAAGTACGGCAAGCACAAA<br>ACCTATCAGAAGAAAAGCGTGACCAACACACAGGGGA<br>ATGGAAAAGAGCAGAGGAGTAAGATGCCTGTGCAGTCA<br>AAACGGCTGCTGAAGAATGGCCCATCTGGAAGTAAAAA<br>ATTCTGGAACAATGTGCTGCCCCACTATCTGGAACTGAA<br>ATAA | |
| SEQ ID NO: 4 | ATGAGAGAGCCAGAGGAGCTGATGCCAGATAGCGGAG<br>CAGTGTTTACCTTCGGAAAGTCCAAGTTCGCAGAGAAT<br>AACCCAGGAAAGTTCTGGTTTAAAAACGACGTGCCCGT<br>CCACCTGTCTTGTGGCGATGAGCATAGTGCCGTGGTCAC<br>TGGGAACAATAAGCTGTATATGTTCGGGTCCAACAATT<br>GGGGACAGCTGGGGCTGGGATCCAAATCTGCTATCTCT<br>AAGCCAACCTGCGTGAAGGCACTGAAACCCGAGAAGGT<br>CAAACTGGCCGCTTGTGGCAGAAACCACACTCTGGTGA<br>GCACCGAGGGCGGGAATGTCTATGCCACCGGAGGCAAC<br>AATGAGGGACAGCTGGGACTGGGGGACACTGAGGAAA<br>GGAATACCTTTCACGTGATCTCCTTCTTTACATCTGAGC<br>ATAAGATCAAGCAGCTGAGCGCCGGCTCCAACACATCT<br>GCAGCCCTGACTGAGGACGGGCGCCTGTTCATGTGGGG<br>AGATAATTCAGAGGGCCAGATTGGGCTGAAAAACGTGA<br>GCAACGTGTGCGTGCCTCAGCAGGTGACCATCGGAAAG<br>CCAGTCAGTTGGATTTCATGTGGCTACTATCATAGCGCC<br>TTCGTGACCACAGATGGCGAGCTGTACGTCTTTGGGGA<br>GCCCGAAAACGGAAAACTGGGCCTGCCTAACCAGCTGC<br>TGGGCAATCACCGGACACCCCAGCTGGTGTCCGAGATC<br>CCTGAAAAAGTGATCCAGGTCGCCTGCGGGGGAGAGCA<br>TACAGTGGTCCTGACTGAGAATGCCGTGTACACCTTCGG<br>ACTGGGCCAGTTTGGCCAGCTGGGGCTGGGAACCTTCCT<br>GTTTGAGACATCCGAACCAAAAGTGATCGAGAACATTC<br>GCGACCAGACTATCAGCTACATTTCCTGCGGAGAGAAT<br>CACACCGCACTGATCACAGACATTGGCCTGATGTATACC<br>TTTGGCGATGGGCGGCACGGGAAGCTGGGACTGGGCCT<br>GGAGAACTTCACTAATCACTTCATCCCCACCCTGTGCTC<br>TAACTTCCTGCGGTTCATCGTGAAACTGGTCGCTTGCGG<br>CGGGTGTCACATGGTGGTCTTCGCTGCACCTCATAGGGG<br>CGTGGCTAAGGAGATCGAATTTGACGAGATTAACGATA<br>CATGCCTGAGCGTGGCAACTTTCCTGCCATACAGCTCCC<br>TGACTTCTGGCAATGTGCTGCAGAGAACCCTGAGTGCA<br>AGGATGCGGAGAAGGGAGAGGGAACGCTCTCCTGACA<br>GTTTCTCAATGCGACGAACCCTGCCACCTATCGAGGGG<br>ACACTGGGACTGAGTGCCTGCTTCCTGCCTAACTCAGTG<br>TTTCCACGATGTAGCGAGCGGAATCTGCAGGAGTCTGTC<br>CTGAGTGAGCAGGATCTGATGCAGCCAGAGGAACCCGA<br>CTACCTGCTGGATGAGATGACCAAGGAGGCCGAAATCG<br>ACAACTCTAGTACAGTGGAGTCCCTGGGCGAGACTACC<br>GATATCCTGAATATGACACACATTATGTCACTGAACAGC<br>AATGAGAAGAGTCTGAAACTGTCACCAGTGCAGAAGCA<br>GAAGAAACAGCAGACTATTGGCGAGCTGACTCAGGACA<br>CCGCCCTGACAGAGAACGACGATAGCGATGAGTATGAG<br>GAAATGTCCGAGATGAAGGAAGGCAAAGCTTGTAAGCA<br>GCATGTGAGTCAGGGGATCTTCATGACACAGCCAGCCA<br>CAACTATTGAGGCTTTTTCAGACGAGGAAGTGGAGATC<br>CCCGAGGAAAAAGAGGGCGCAGAAGATTCCAAGGGGA<br>ATGGAATTGAGGAACAGGAGGTGGAAGCCAACGAGGA<br>AAATGTGAAAGTCCACGGAGGCAGGAAGGAGAAAACA<br>GAAATCCTGTCTGACGATCTGACTGACAAGGCCGAGGT<br>GTCCGAAGGCAAGGCAAAATCTGTCGGAGAGGCAGAA<br>GACGGACCAGAGGGACGAGGGGATGGAACCTGCGAGG<br>AAGGCTCAAGCGGGGCTGAGCATTGGCAGGACGAGGA | Codon-optimized RPGR ORF15 coding sequence #2 |

-continued

SEQUENCE LISTING

| SEQ ID NO | Sequence | Description |
|---|---|---|
| | ACGAGAGAAGGGCGAAAAGGATAAAGGCCGCGGGGAG<br>ATGGAACGACCTGGAGAGGGCGAAAAAGAGCTGGCAG<br>AGAAGGAGGAATGGAAGAAAAGGGACGGCGAGGAACA<br>GGAGCAGAAAGAAAGGGAGCAGGGCCACCAGAAGGAG<br>CGCAACCAGGAGATGGAAGAGGGCGGCGAGGAAGAGC<br>ATGGCGAGGGAGAAGAGGAAGAGGGCGATAGAGAAGA<br>GGAAGAGGAAAAAGAAGGCGAAGGGAAGGAGGAAGG<br>AGAGGGCGAGGAAGTGGAAGGCGAGAGGGAAAAGGAG<br>GAAGGAGAACGGAAGAAAGAGGAAAGAGCCGGCAAAG<br>AGGAAAAGGGCGAGGAAGAGGGCGATCAGGGCGAAGG<br>CGAGGAGGAAGAGACCGAGGGCCGCGGGGAAGAGAAA<br>GAGGAGGGAGGAGAGGTGGAGGGCGGAGAGGTCGAAG<br>AGGGAAAGGGCGAGCGCGAAGAGGAAGAGGAAGAGGG<br>CGAGGGCGAGGAAGAAGAGGGCGAGGGGGAAGAAGAG<br>GAGGGAGAGGGCGAAGAGGAAGAGGGGGAGGGAAAG<br>GGCGAAGAGGAAGGAGAGGAAGGGGAGGGAGAGGAA<br>GAGGGGGAGGAGGGCGAGGGGGAAGGCGAGGAGGAA<br>GAAGGAGAGGGGGAAGGCGAAGAGGAAGGCGAGGGG<br>GAAGGAGAGGAGGAAGAAGGGGAAGGCGAAGGCGAA<br>GAGGAGGGAGAAGGAGAGGGGGAGGAAGAGGAAGGA<br>GAAGGGAAGGGCGAGGAGGAAGGCGAAGAGGGAGAG<br>GGGGAAGGCGAGGAAGAGGAAGGCGAGGGCGAAGGAG<br>AGGACGGCGAGGGCGAGGGAGAAGAGGAGGAAGGGGA<br>ATGGGAAGGCGAAGAAGAGGAAGGCGAAGGCGAAGGC<br>GAAGAAGAGGGCGAAGGGGAGGGCGAGGAGGGCGAAG<br>GCGAAGGGGAGGAAGAGGAAGGCGAAGGAGAAGGCGA<br>GGAAGAAGAGGGAGAGGAGGAAGGCGAGGAGGAAGG<br>AGAGGGGGAGGAGGAGGGAGAAGGCGAGGGCGAAGA<br>AGAAGAAGAGGGAGAAGTGGAGGGCGAAGTCGAGGGG<br>GAGGAGGGAGAAGGGGAAGGGGAGGAAGAAGAGGGC<br>GAAGAAGAAGGCGAGGAAAGAGAAAAAGAGGGAGAA<br>GGCGAGGAAAACCGGAGAAATAGGGAAGAGGAGGAAG<br>AGGAAGAGGGAAAGTACCAGGAGACAGGCGAAGAGGA<br>AAACGAGCGGCAGGATGGCGAGGAATATAAGAAAGTG<br>AGCAAGATCAAAGGATCCGTCAAGTACGGCAAGCACAA<br>AACCTATCAGAAGAAAAGCGTGACCAACACACAGGGG<br>AATGGAAAAGAGCAGCGAAGTAAAATGCCTGTGCAGTC<br>AAAACGGCTGCTGAAGAATGGCCCAAGCGGGTCTAAAA<br>AATTCTGGAACAATGTCCTGCCACACTATCTGGAACTGA<br>AGTGA | |
| SEQ ID NO: 5 | ATGAGAGAGCCCGAGGAACTGATGCCCGATAGCGGAGC<br>CGTCTTCACCTTTGGGAAATCTAAATTCGCAGAGAACAA<br>CCCTGGAAAATTCTGGTTTAAGAACGACGTGCCCGTGC<br>ACCTGAGCTGTGGCGATGAGCACTCCGCCGTGGTGACA<br>GGCAACAATAAGCTGTACATGTTCGGCTCTAACAATTG<br>GGGACAGCTGGGCCTGGGAAGCAAGTCCGCCATCAGCA<br>AGCCAACCTGCGTGAAGGCCCTGAAGCCCGAGAAGGTG<br>AAGCTGGCCGCCTGTGGCAGAAACCACACACTGGTGAG<br>CACCGAGGGCGGCAATGTGTATGCCACAGGCGGCAACA<br>ATGAAGGACAGCTGGGCCTGGGCGACACAGAGGAGAG<br>GAATACCTTTCACGTGATCAGCTTCTTTACCTCCGAGCA<br>CAAGATCAAGCAGCTGTCCGCCGGCTCTAACACATCTG<br>CAGCACTGACAGAGGATGGAAGACTGTTCATGTGGGGC<br>GATAATAGCGAGGGCCAGATCGGCCTGAAGAACGTGTC<br>CAATGTGTGCGTGCCTCAGCAGGTGACCATCGGCAAGC<br>CAGTGTCCTGGATCTCTTGTGGCTACTATCACAGCGCCT<br>TCGTGACCACAGATGGCGAGCTGTACGTGTTTGGAGAG<br>CCTGAGAATGGCAAGCTGGGCCTGCCTAACCAGCTGCT<br>GGGCAATCACCGGACACCCCAGCTGGTGTCCGAGATCC<br>CTGAGAAAGTGATCCAGGTGGCATGTGGCGGCGAGCAC<br>ACAGTGGTGCTGACCGAGAATGCCGTGTATACCTTTGGC<br>CTGGGACAGTTTGGCCAGCTGGGCCTGGGCACATTCCTG<br>TTTGAGACATCCGAGCCAAAAGTGATCGAGAACATCCG<br>CGACCAGACAATCAGCTACATCTCCTGCGGCGAGAATC<br>ACACAGCCCTGATCACCGACATCGGCCTGATGTATACCT<br>TTGGCGATGGAAGACACGGCAAGCTGGGCCTGGGCCTG<br>GAGAACTTCACAAATCACTTTATCCCCACCCTGTGTTCT<br>AACTTCCTGCGGTTCATCGTGAAGCTGGTGGCCTGCGGC<br>GGATGTCACATGGTGGTGTTTGCAGCCCCTCACAGGGG<br>CGTGGCCAAGGAGATCGAGTTTGACGAGATCAACGATA<br>CATGCCTGTCCGTGGCCACCTTCCTGCCATACAGCTCCC<br>TGACATCCGGCAATGTGCTGCAGAGAACCCTGTCTGCA<br>AGAATGAGAAGAAGGGAGAGAGAGCGGTCCCCTGACT<br>CTTTCAGCATGAGAAGAACACTGCCCCCTATTGAGGGA | Codon-optimized RPGR ORF15 coding sequence #3 |

-continued

SEQUENCE LISTING

| SEQ ID NO | Sequence | Description |
|---|---|---|
| | ACCCTGGGCCTGTCTGCCTGCTTCCTGCCTAACTCTGTG<br>TTTCCAAGATGTAGCGAGAGGAATCTGCAGGAGTCTGT<br>GCTGAGCGAGCAGGATCTGATGCAGCCAGAGGAGCCCG<br>ACTACCTGCTGGATGAGATGACAAAGGAGGCCGAGATC<br>GACAACTCTAGCACCGTGGAGAGCCTGGGCGAGACAAC<br>AGATATCCTGAATATGACACACATCATGTCCCTGAACTC<br>TAATGAGAAGTCTCTGAAGCTGAGCCCAGTGCAGAAGC<br>AGAAGAAGCAGCAGACCATCGGCGAGCTGACCCAGGA<br>CACAGCCCTGACCGAGAACGACGATTCTGATGAGTATG<br>AGGAGATGAGCGAGATGAAGGAGGGCAAGGCCTGTAA<br>GCAGCACGTGTCCCAGGGCATCTTCATGACCCAGCCAG<br>CCACCACAATCGAGGCCTTTTCTGACGAGGAGGTGGAG<br>ATCCCCGAGGAGAAGGAGGGCGCCGAGGATAGCAAGG<br>GCAATGGCATCGAGGAGCAGGAGGTGGAGGCCAACGA<br>GGAGAATGTGAAGGTGCACGGCGGAAGAAAGGAGAAG<br>ACAGAGATCCTGTCCGACGATCTGACCGACAAGGCCGA<br>GGTGTCCGAGGGCAAGGCCAAGTCTGTGGGAGAGGCAG<br>AGGATGGACCTGAGGGACGCGGCGATGGAACATGTGAG<br>GAGGGCTCCTCTGGAGCAGAGCACTGGCAGGATGAGGA<br>GAGAGAGAAGGGCGAGAAGGATAAGGGCAGAGGCGAG<br>ATGGAGAGGCCTGGAGAGGGAGAGAAGGAGCTGGCAG<br>AGAAGGAGGAGTGGAAGAAGAGGGATGGCGAGGAGCA<br>GGAGCAGAAGGAGAGAGAGCAGGGCCACCAGAAAGAG<br>AGGAACCAGGAGATGGAAGAGGGCGGCGAGGAGGAGC<br>ACGGAGAGGGAGAGGAGGAGGAGGGCGATAGAGAAGA<br>AGAGGAGGAGAAAGAGGGAGAGGGCAAGGAGGAGGG<br>AGAGGGAGAAGAAGTGGAAGGAGAGAGAGAGAAGGA<br>GGAAGGAGAGCGCAAGAAGGAAGAAAGAGCAGGCAAG<br>GAGGAGAAAGGAGAGGAGGAGGGCGATCAGGGAGAAG<br>GAGAGGAGGAGGAGACAGAAGGACGCGGCGAGGAAAA<br>AGAGGAGGGCGGCGAGGTCGAGGGCGGCGAGGTCGAA<br>GAGGGCAAGGGCGAAAGAGAAGAAGAGGAGGAGGAA<br>GGCGAGGGCGAAGAAGAGGAGGGCGAGGGCGAGGAAG<br>AAGAGGGCGAGGGCGAAGAGGAAGAAGGAGAGGGCAA<br>GGGCGAGGAGGAGGGCGAAGAAGGCGAAGGGGAGGAG<br>GAGGGCGAAGAGGGAGAGGGCGAGGGCGAGGAGGAAG<br>AAGGCGAAGGAGAAGGCGAAGAAGAAGGAGAAGGAG<br>AGGGAGAAGAGGAGGAAGGCGAAGGAGAGGGGGAAG<br>AGGAAGGAGAAGGGGAGGGCGAAGAGGAGGAGGGAG<br>AAGGCAAGGGAGAGGAGGAGGGCGAGGAAGGAGAAG<br>GCGAAGGCGAGGAGGAGGAAGGAGAGGGAGAAGGAG<br>AAGATGGAGAAGGAGAGGGCGAGGAAGAGGAAGGAGA<br>GTGGGAGGGCGAGGAAGAGGAGGGAGAAGGAGAAGGA<br>GAAGAAGAAGGAGAAGGCGAGGGAGAAGAAGGAGAG<br>GGAGAAGGGGAAGAAGAGGAGGGGGAAGGAGAGGGC<br>GAGGAGGAAGAGGGAGAAGAAGAAGGCGAAGAAGAG<br>GGAGAAGGCGAGGAAGAAGGAGAGGGAGAGGGGGAA<br>GAGGAGGAAGAGGGCGAGGTGGAAGGAGAGGTGGAGG<br>GCGAAGAGGGGGAAGGGGAAGGAGAAGAAGAAGAAG<br>GAGAGGAGGAGGGAGAGGAGAGAGAGAAAGAAGGCG<br>AGGGCGAGGAGAACAGAAGGAATCGCGAAGAAGAAGA<br>AGAAGAGGAGGGCAAGTACCAGGAGACAGGCGAGGAG<br>GAGAACGAGCGGCAGGATGGCGAGGAGTATAAGAAGG<br>TGTCCAAGATCAAGGGCTCTGTGAAGTACGGCAAGCAC<br>AAGACCTATCAGAAGAAGAGCGTGACCAACACACAGG<br>GCAATGGCAAGGAGCAGCGCAGCAAGATGCCTGTGCAG<br>TCCAAGCGGCTGCTGAAGAATGGCCCAAGCGGGTCTAA<br>AAAATTCTGGAACAATGTCCTGCCACACTATCTGGAACT<br>GAAATAA | |
| SEQ ID NO: 6 | ATGAGAGAACCCGAGGAACTGATGCCTGACTCTGGCGC<br>CGTGTTCACCTTCGGCAAGAGCAAGTTCGCCGAGAACA<br>ACCCCGGCAAGTTCTGGTTCAAGAACGACGTGCCAGTG<br>CACCTGAGCTGTGGCGACGAACATTCTGCCGTGGTCACC<br>GGCAACAACAAGCTGTACATGTTCGGCAGCAACAACTG<br>GGGCCAGCTCGGCCTGGGATCTAAGAGCGCCATCAGCA<br>AGCCTACCTGCGTGAAGGCCCTGAAGCCTGAGAAAGTG<br>AAGCTGGCCGCCTGCGGCAGAAATCACACCCTGGTTTCT<br>ACCGAAGGCGGCAACGTGTACGCCACCGGCGGAAACAA<br>TGAAGGACAGCTTGGACTGGGCGACACCGAGGAAAGA<br>AACACCTTCCACGTGATCAGCTTTTTCACCAGCGAGCAC<br>AAGATCAAGCAGCTGAGCGCCGGCAGCAATACCTCTGC<br>TGCCCTGACAGAAGATGGCCGGCTGTTCATGTGGGGCG<br>ACAATTCTGAGGGCCAGATCGGACTGAAGAACGTGTCC<br>AATGTGTGCGTGCCCCAGCAAGTGACAATCGGCAAGCC | Codon-optimized RPGR ORF15 coding sequence #4 |

-continued

| SEQUENCE LISTING | | |
|---|---|---|
| SEQ ID NO | Sequence | Description |
| | TGTGTCCTGGATCAGCTGCGGCTACTACCACAGCGCCTT<br>CGTGACAACAGACGGCGAGCTGTATGTGTTCGGCGAGC<br>CCGAGAATGGCAAGCTGGGACTGCCTAATCAGCTGCTG<br>GGCAACCACAGAACCCCTCAGCTGGTGTCTGAGATCCC<br>CGAAAAAGTGATCCAGGTGGCCTGTGGCGGAGAGCACA<br>CAGTGGTGCTGACAGAGAATGCCGTGTACACATTTGGC<br>CTGGGCCAGTTTGGCCAACTCGGACTGGGCACCTTCCTG<br>TTCGAGACAAGCGAGCCCAAAGTGATCGAGAACATCCG<br>GGACCAGACCATCAGCTACATCTCTTGCGGCGAGAACC<br>ACACAGCCCTGATCACAGACATCGGCCTGATGTATACCT<br>TCGGCGACGGCAGACACGGCAAACTCGGCCTTGGCCTG<br>GAAAACTTCACCAACCACTTCATCCCTACTCTGTGCAGC<br>AACTTCCTGCGGTTCATCGTGAAACTGGTGGCCTGCGGA<br>GGCTGCCACATGGTGGTTTTTGCCGCTCCTCATAGAGGC<br>GTGGCCAAAGAGATTGAGTTCGACGAGATCAACGATAC<br>CTGCCTGAGCGTGGCCACCTTTCTGCCTTACAGCTCTCT<br>GACCAGCGGCAATGTGCTGCAGAGGACACTGAGCGCCA<br>GAATGCGCAGACGGGAAAGAGAGAGAAGCCCCGACAG<br>CTTCAGCATGCGGAGAACCCTGCCTCCAATCGAGGGAA<br>CACTGGGCCTGAGCGCCTGCTTCCTGCCTAATAGCGTGT<br>TCCCCAGATGCAGCGAGCGGAACCTGCAAGAGTCTGTG<br>CTGAGCGAGCAGGACCTGATGCAGCCTGAGGAACCCGA<br>CTACCTGCTGGACGAGATGACCAAAGAGGCCGAGATCG<br>ACAACAGCAGCACCGTGGAATCTCTGGGCGAGACAACC<br>GACATCCTGAACATGACCCACATCATGAGCCTGAACAG<br>CAACGAGAAGTCTCTGAAGCTGAGCCCCGTGCAGAAGC<br>AGAAGAAGCAGCAGACCATCGGAGAGCTGACCCAGGA<br>TACCGCTCTGACCGAGAACGACGACAGCGACGAGTACG<br>AAGAGATGAGCGAGATGAAGGAAGGCAAGGCCTGCAA<br>GCAGCACGTGTCCCAGGGCATCTTTATGACCCAGCCTGC<br>CACCACCATCGAGGCCTTTTCCGACGAGGAAGTGGAAA<br>TCCCCGAGGAAAAAGAGGGCGCCGAGGACAGCAAAGG<br>CAACGGCATTGAGGAACAAGAGGTGGAAGCCAACGAA<br>GAGAACGTGAAGGTGCACGGCGGACGGAAAGAGAAAA<br>CAGAGATCCTGAGCGACGACCTGACCGACAAGGCCGAA<br>GTGTCTGAGGGCAAAGCCAAGTCTGTGGGCGAAGCCGA<br>GGACGGCCCAGAAGGCAGAGGCGACGGAACATGTGAA<br>GAGGGATCTAGCGGAGCCGAGCACTGGCAGGACGAAG<br>AGAGAGAGAAAGGCGAGAAGGACAAAGGCAGGGGCGA<br>GATGGAAAGACCTGGCGAGGGCGAAAAAGAGCTGGCC<br>GAGAAAGAGGAGTGGAAGAAACGCGACGGCGAAGAAC<br>AAGAGCAGAAAGAACGCGAGCAGGGCCACCAGAAAGA<br>AAGAAATCAAGAGATGGAAGAAGGCGGCGAGGAAGAA<br>CACGGCGAAGGGGAAGAAGAGGAAGGCGACCGAGAGG<br>AAGAAGAAGAAAAAGAAGGCGAAGGCAAAGAGGAAG<br>GCGAGGGCGAAGAGGTGGAAGGCGAGCGGGAAAAAGA<br>AGAGGGCGAGCGCAAGAAAGAAGAAAGAGCCGGCAAA<br>GAAGAGAAGGGCGAAGAAGAAGGCGATCAAGGCGAAG<br>GCGAGGAAGAAGAAACCGAAGGCCGCGGAGAAGAGAA<br>AGAGGAAGGCGGCGAAGTTGAAGGCGGCGAGGTGGAA<br>GAAGGCAAGGGCGAGAGAGAAGAAGAGGAAGAGGAA<br>GGCGAAGGGGAAGAAGAAGAAGGCGAGGGCGAAGAGG<br>AAGAAGGCGAAGGCGAGGAAGAGGAAGGCGAAGGCAA<br>GGGCGAAGAGGAAGGCGAAGAAGGCGAGGGCGAAGAA<br>GAGGGAGAAGAAGGCGAAGGCGAGGGCGAAGAAGAGG<br>AAGGCGAAGGCGAAGGCGAGGAAGAAGGCGAAGGCGA<br>AGGCGAAGAGGAAGAAGGCGAAGGCGAAGGGGAAGAA<br>GAAGGCGAAGGCGAAGGCGAGGAAGAGGAAGGCGAAG<br>GCAAAGGGGAAGAAGAGGGCGAAGAAGGCGAAGGCGA<br>AGGCGAGGAAGAAGAAGGCGAAGGCGAAGGCGAAGAC<br>GGCGAAGGCGAGGGCGAAGAGGAAGAGGGCGAGTGGG<br>AGGGCGAAGAAGAAGAAGGCGAAGGCGAGGGCGAAGA<br>GGAAGGCGAAGGCGAAGGCGAAGAAGGCGAGGGCGAA<br>GGCGAAGAAGAAGAAGGCGAAGGCGAAGGCGAAGAAG<br>AGGAAGGGGAAGAAGAAGGCGAAGAGGAAGGCGAGG<br>GCGAAGAAGAAGGCGAAGGCGAGGGCGAAGAAGAGGA<br>AGAGGGCGAAGTTGAAGGGGAAGTTGAGGGCGAAGAA<br>GGCGAAGGCGAAGGGGAAGAAGAGGAAGGCGAGGAAG<br>AGGGCGAAGAACGCGAGAAAGAAGGCGAAGGGGAAGA<br>GAACCGCCGGAACAGAGAAGAGGAAGAAGAAGAGGAA<br>GGCAAGTACCAAGAGACAGGCGAGGAAGAGAACGAGC<br>GGCAGGATGGCGAAGAGTACAAGAAGGTGTCCAAGATC<br>AAGGGCAGCGTGAAGTACGGCAAGCACAAGACCTACCA<br>GAAAAAGTCCGTGACCAACACACAAGGCAATGGCAAA<br>GAACAGCGGAGCAAGATGCCCGTGCAGTCCAAGAGACT | |

-continued

SEQUENCE LISTING

| SEQ ID NO | Sequence | Description |
|---|---|---|
| | GCTGAAGAATGGCCCCAGCGGCAGCAAAAAGTTCTGGA ACAACGTGCTGCCCCACTACCTGGAACTGAAGTGA | |
| SEQ ID NO: 7 | GGGCCCCAGAAGCCTGGTGGTTGTTTGTCCTTCTCAGGG GAAAAGTGAGGCGGCCCCTTGGAGGAAGGGGCCGGGC AGAATGATCTAATCGGATTCCAAGCAGCTCAGGGGATT GTCTTTTTCTAGCACCTTCTTGCCACTCCTAAGCGTCCTC CGTGACCCCGGCTGGGATTTAGCCTGGTGCTGTGTCAGC CCCGGGCTCCCAGGGGCTTCCCAGTGGTCCCCAGGGAA CCCTCGACAGGGCCAGGGCGTCTCTCTCGTCCAGCAAG GGCAGGGACGGGCCACAGGCAAGGGC | GRK1 long (GRK1L) sequence |
| SEQ ID NO: 8 | GGGCCCCAGAAGCCTGGTGGTTGTTTGTCCTTCTCAGGG GAAAAGTGAGGCGGCCCCTTGGAGGAAGGGGCCGGGC AGAATGATCTAATCGGATTCCAAGCAGCTCAGGGGATT GTCTTTTTCTAGCACCTTCTTGCCACTCCTAAGCGTCCTC CGTGACCCCGGCTGGGATTTAGCCTGGTGCTGTGTCAGC CCCGGG | GRKIS short (GRKIS) sequence |
| SEQ ID NO: 9 | CTGTGCCTTCTAGTTGCCAGCCATCTGTTGTTTGCCCCTC CCCCGTGCCTTCCTTGACCCTGGAAGGTGCCACTCCCAC TGTCCTTTCCTAATAAAATGAGGAAATTGCATCGCATTG TCTGAGTAGGTGTCATTCTATTCTGGGGGGTGGGGTGGG GCAGGACAGCAAGGGGGAGGATTGGGAAGACAATAGC AGGCATGCTGGGGATGCGGTGGGCTCTATGG | bGHpA sequence |
| SEQ ID NO: 10 | GATCCAGACATGATAAGATACATTGATGAGTTTGGACA AACCACAACTAGAATGCAGTGAAAAAAATGCTTTATTT GTGAAATTTGTGATGCTATTGCTTTATTTGTAACCATTAT AAGCTGCAATAAACAAGTT | SV40pA sequence |
| SEQ ID NO: 11 | AATAAAGGAAATTTATTTTCATTGCAATAGTGTGTTGGA ATTTTTTGTGTCTCTCA | rbGlobpA sequence |
| SEQ ID NO: 12 | GGGTGGCATCCCTGTGACCCCTCCCCAGTGCCTCTCCTG GCCCTGGAAGTTGCCACTCCAGTGCCCACCAGCCTTGTC CTAATAAAATTAAGTTGCATCATTTTGTCTGACTAGGTG TCCTTCTATAATATTATGGGGTGGAGGGGGGTGGTATGG AGCAAGGGGCAAGTTGGGAAGACAACCTGTAGGGCCTG CGGGGTCTATTGGGAACCAAGCTGGAGTGCAGTGGCAC AATCTTGGCTCACTGCAATCTCCGCCTCCTGGGTTCAAG CGATTCTCCTGCCTCAGCCTCCCGAGTTGTTGGGATTCC AGGCATGCATGACCAGGCTCAGCTAATTTTTGTTTTTTT GGTAGAGACGGGGTTTCACCATATTGGCCAGGCTGGTC TCCAACTCCTAATCTCAGGTGATCTACCCACCTTGGCCT CCCAAATTGCTGGGATTACAGGCGTGAACCACTGCTCCC TTCCCTGTCCTT | hGHpA sequence |
| SEQ ID NO: 13 | GTAAGTTTAGTCTTTTTGTCTTTTATTTCAGGTCCCGGAT CCGGTGGTGGTGCAAATCAAAGAACTGCTCCTCAGTGG ATGTTGCCTTTACTTCTAG | SV40 intron sequence |

What is claimed is:

1. A composition comprising:

(i) a first polynucleotide, wherein the first polynucleotide comprises a first sequence operably linked to a first promoter and a second sequence operably linked to a second promoter, the first sequence encoding an adeno-associated virus (AAV) capsid protein, the second sequence encoding an AAV rep protein, wherein the first promoter and the second promoter are suitable for expression in insect cells; and (ii) a second polynucleotide, wherein the second polynucleotide comprises a third sequence operably linked to a Rhodopsin kinase (GRK1) promoter comprising a sequence of SEQ ID NO: 7, wherein the third sequence is a codon-optimized sequence encoding an RPGR ORF15 polypeptide, wherein the third sequence comprises SEQ ID NO: 4 or SEQ ID NO: 5, wherein the 3' end of the third sequence comprises a poly A sequence of SEQ ID NO: 10;

wherein the second polynucleotide further comprises an intron sequence of SEQ ID NO: 13 located downstream of the GRK1 promoter;

wherein the insect cells are Sf9 cells; and wherein the AAV capsid protein comprises an AAV5 capsid protein.

2. The composition of claim 1, wherein the first promoter or the second promoter is a p10 promoter or a polh promoter.

3. The composition of claim 1, wherein the second polynucleotide further comprises a stuffer sequence.

4. The composition of claim 1, wherein the second polynucleotide further comprises an inverted terminal repeat (ITR) sequence.

5. The composition of claim 4, wherein the inverted terminal repeat (ITR) sequence is an adeno-associated virus (AAV) serotype 2 ITR sequence.

6. The composition of claim 1, wherein the second polynucleotide further comprises a fourth sequence encoding a therapeutic protein.

7. The composition of claim 6, wherein the therapeutic protein is selected from the group consisting of: RPGRIP1, RPGRIP1L, SMC1, SMC3, Whirlin, PDE5, and RAB8.

8. The composition of claim 6, wherein the third sequence and the fourth sequence are connected by a sequence encoding a linker.

9. The composition of claim 8, wherein the linker is a cleavable linker or wherein the linker comprises a sequence encoding a 2A peptide.

10. A recombinant adeno-associated virus (rAAV) particle prepared by introducing the composition of claim 1 into the Sf9 cells.

11. A system for treating X linked retinitis pigmentosa comprising the recombinant adeno-associated virus (rAAV) particle of claim 10 and a pharmaceutically acceptable carrier, wherein the system is formulated for subretinal injection.

12. A method for treating X linked retinitis pigmentosa in a subject in need thereof comprising administering to an ocular cell of the subject the system of claim 11.

13. A kit comprising the system of claim 11 and instructions.

* * * * *

SEQUENCE LISTING

```
Sequence total quantity: 13
SEQ ID NO: 1           moltype = AA  length = 1152
FEATURE                Location/Qualifiers
source                 1..1152
                       mol_type = protein
                       organism = Homo sapiens
SEQUENCE: 1
MREPEELMPD SGAVFTFGKS KFAENNPGKF WFKNDVPVHL SCGDEHSAVV TGNNKLYMFG  60
SNNWGQLGLG SKSAISKPTC VKALKPEKVK LAACGRNHTL VSTEGGNVYA TGGNNEGQLG  120
LGDTEERNTF HVISFFTSEH KIKQLSAGSN TSAALTEDGR LFMWGDNSEG QIGLKNVSNV  180
CVPQQVTIGK PVSWISCGYY HSAFVTTDGE LYVFGEPENG KLGLPNQLLG NHRTPQLVSE  240
IPEKVIQVAC GGEHTVVLTE NAVYTFGLGQ FGQLGLGTFL FETSEPKVIE NIRDQTISYI  300
SCGENHTALI TDIGLMYTFG DGRHGKLGLG LENFTNHFIP TLCSNFLRFI VKLVACGGCH  360
MVVFAAPHRG VAKEIEFDEI NDTCLSVATF LPYSSLTSGN VLQRTLSARM RRRERERSPD  420
SFSMRRTLPP IEGTLGLSAC FLPNSVFPRC SERNLQESVL SEQDLMQPEE PDYLLDEMTK  480
EAEIDNSSTV ESLGETTDIL NMTHIMSLNS NEKSLKLSPV QKQKKQQTIG ELTQDTALTE  540
NDDSDEYEEM SEMKEGKACK QHVSQGIFMT QPATTIEAFS DEEVEIPEEK EGAEDSKGNG  600
```

```
IEEQEVEANE ENVKVHGGRK EKTEILSDDL TDKAEVSEGK AKSVGEAEDG PEGRGDGTCE  660
EGSSGAEHWQ DEEREKGEKD KGRGEMERPG EGEKELAEKE EWKKRDGEEQ EQKEREQGHQ  720
KERNQEMEEG GEEEHGEGEE EEGDREEEEE KEGEGKEEGE GEEVEGEREK EEGERKKEER  780
AGKEEKGEEE GDQGEGEEEE TEGRGEEKEE GGEVEGGEVE EGKGEREEEE EEGEGEEEEG  840
EGEEEEGEGE EEEGEGKGEE EGEEGEGEEE GEEGEGEGEE EEGEGEGEEE GEGEGEEEEG  900
EGEGEEEGEG EGEEEEGEGK GEEEGEEGEG EGEEEEGEGE GEDGEGEGEE EEGEWEGEEE  960
EGEGEGEEEG EGEGEEGEGE GEEEGEEGEG EEEGEEEEGE EEGEGEEEGE GEGEEEEEGE  1020
VEGEVEGEEG EGEGEEEEGE EEGEEREKEG EGEENRRNRE EEEEEEGKYQ ETGEEENERQ  1080
DGEEYKKVSK IKGSVKYGKH KTYQKKSVTN TQGNGKEQRS KMPVQSKRLL KNGPSGSKKF  1140
WNNVLPHYLE LK                                                      1152

SEQ ID NO: 2            moltype = DNA  length = 3459
FEATURE                 Location/Qualifiers
source                  1..3459
                        mol_type = other DNA
                        organism = Homo sapiens
SEQUENCE: 2
atgagggagc cggaagagct gatgcccgat tcgggtgctg tgtttacatt tgggaaaagt  60
aaatttgctg aaaataatcc cggtaaattc tggtttaaaa atgatgtccc tgtacatctt  120
tcatgtggag atgaacattc tgctgttgtt accggaaata ataaacttta catgtttggc  180
agtaacaact ggggtcagtt aggattagga tcaaagtcag ccatcagcaa gccaacatgt  240
gtcaaagctc taaaacctga aaaagtgaaa ttagctgcct gtggaaggaa ccacaccctg  300
gtgtcaacag aaggaggcaa tgtatatgca actggtggaa ataatgaagg acagttgggg  360
cttggtgaca ccgaagaaag aaacactttt catgtaatta gctttttttac atccgagcat  420
aagattaagc agctgtctgc tggatctaat acttcagctg ccctaactga ggatggaaga  480
ctttttatgt ggggtgacaa ttccgaaggg caaattggtt taaaaaatgt aagtaatgtc  540
tgtgtccctc agcaagtgac cattgggaaa cctgtctcct ggatctcttg tggatattac  600
cattcagctt ttgtaacaac agatggtgag ctatatgtgt ttggagaacc tgagaatggg  660
aagttaggtc ttcccaatca gctcctgggc aatcacagaa cacccccagct ggtgtctgaa  720
attccggaga aggtgatcca agtagcctgt ggtggagagc atactgtggt tctcacggag  780
aatgctgtgt ataccctttgg gctgggacaa tttggtcagc tgggtcttgg cacttttcctt  840
tttgaaactt cagaacccaa agtcattgag aatattaggg atcaaacaat aagttatatt  900
tcttgtggag aaaatcacac agctttgata acagatatcg gccttatgta tactttttgga  960
gatggtcgcc acggaaaatt aggacttgga ctggagaatt ttaccaatca cttcattcct  1020
actttgtgct ctaatttttt gaggtttata gttaaatttgg ttgcttgtgg tggatgtcac  1080
atggtagttt ttgctgctcc tcatcgtggt gtggcaaaag aaattgaatt cgatgaaata  1140
aatgatactt gcttatctgt ggcgactttt ctgccgtata gcagtttaac ctcaggaaat  1200
gtactgcaga ggactctatc agcacgtatg cggcgaagag agagggagag gtctccagat  1260
tctttttcaa tgaggagaac actacctcca atagaaggga ctcttggcct ttctgcttgt  1320
tttctcccca attcagtctt tccacgatgt tctgagagaa acctccaaga gagtgtctta  1380
tctgaacagg acctcatgca gccagaggaa ccagattatt tgctagatga aatgaccaaa  1440
gaagcagaga tagataattc ttcaactgta gaaagccttg gagaaactac tgatatctta  1500
aacatgacac acatcatgag cctgaattcc aatgaaaagt cattaaaatt atcaccagtt  1560
cagaaacaaa agaaacaaca aacaattggg gaactgacgc aggatacagc tcttactgaa  1620
aacgatgata gtgatgaata tgaagaaatg tcagaaatga aagaagggaa agcatgtaaa  1680
caacatgtgt cacaagggat tttcatgacg cagccagcta cgactatcga agcattttca  1740
gatgaggaag tagagatccc agaggagaag gaaggagcag aggattcaaa aggaaatgga  1800
atagaggagc aagaggtaga agcaaatgag gaaaatgtga aggtgcatgg aggaagaaag  1860
gagaaaacag agatcctatc agatgacctt acagacaaag cagaggtgag tgaaggcaag  1920
gcaaaatcag tgggagaagc agaggatggg cctgaaggta gaggggatgg aacctgtgag  1980
gaaggtagtt caggagcaga acactggcaa gatgaggaga gggagaaggg ggagaaagac  2040
aagggtagag gagaaatgga gaggccagga gagggagaga aggaactagc agagaaggaa  2100
gaatggaaga agagggatgg ggaagagcag gagcaaaagg agagggagca gggccatcag  2160
aaggaaagaa accaagagat ggaggaggga ggggaggagg agcatggaga aggagaagaa  2220
gaggagggag acagagaaga ggaagaagag aaggagggag aagggaaaga ggaaggagaa  2280
ggggaagaag tggagggaga acgtgaaaag gaggaaggag agaggaaaaa ggaggaaaga  2340
gcggggaagg aggagaaagg agaggaagaa ggagaccaag gagaggggga agaggaggaa  2400
acagagggga gaggggagga aaaagaggag ggaggggaag tagagggagg ggaagtagag  2460
gaggggaaag gagagaggga agaggaagag gaggagggtg aggggggaaga ggaggaaggg  2520
gagggggaag aggaggaagg ggagggggaa gaggaggaag gagaagggaa aggggaggaa  2580
gaaggggaag aaggagaagg ggaggaagaa ggggaggaag gagaagggga gggggaagag  2640
gaggaaggag aaggggaggg agaagaggaa ggagaagggg agggagaaga ggaggaagga  2700
gaaggggagg gagaagagga aggagaaggg gagggagaag aggaggaagg agaagggaaa  2760
ggggaggagg aaggagagga aggagaaggg gagggggaag aggaggaagg agaaggggaa  2820
ggggaggatg gagaaggggga gggggaagag gaggaaggag aatgggaggg ggaagaggag  2880
gaaggagaag gggagggggga agaggaagga gaaggggaag gggaggaagg agaaggggag  2940
ggggaagagg aggaaggaga aggggagggg gaagaggagg aaggggaaga agaaggggag  3000
gaagaaggag agggagagga agaaggggag ggagaagggg aggaagaaga ggaaggggaa  3060
gtggaagggg aggtggaagg ggaggaagga gagggggaag gagaggaaga ggaaggagag  3120
gaggaaggag aagaaaggga aaaggagggg gaaggagaag aaaacaggag gaacagagaa  3180
gaggaggagg aagaagaggg gaagtatcag gagacaggcg aagaagagaa tgaaaggcag  3240
gatggagagg agtacaaaaa agtgagcaaa ataaaaggat ctgtgaaata tggcaaacat  3300
aaaacatatc aaaaaaagtc agttactaac acacagggaa atgggaaaga gcagaggtcc  3360
aaaatgccag tccagtcaaa acgacttttta aaaaacgggc catcaggttc caaaaagttc  3420
tggaataatg tattaccaca ttacttggaa ttgaagtaa                         3459

SEQ ID NO: 3            moltype = DNA  length = 3459
FEATURE                 Location/Qualifiers
misc_feature            1..3459
```

```
                          note = Description of Artificial Sequence: Synthetic
                           polynucleotide
source                    1..3459
                          mol_type = other DNA
                          organism = synthetic construct
SEQUENCE: 3
atgagagagc cagaggagct gatgccagac agtggagcag tgtttacatt cggaaaatct  60
aagttcgctg aaaataaccc aggaaagttc tggtttaaaa acgacgtgcc cgtccacctg  120
tcttgtggcg atgagcatag tgccgtggtc actgggaaca ataagctgta catgttcggg  180
tccaacaact ggggacagct ggggctggga tccaaatctg ctatctctaa gccaacctgc  240
gtgaaggcac tgaaacccga gaaggtcaaa ctggccgctt gtggcagaaa ccacactctg  300
gtgagcaccg agggcgggaa tgtctatgcc accggaggca acaatgaggg acagctggga  360
ctgggggaca ctgaggaaag gaataccttt cacgtgatct ccttctttac atctgagcat  420
aagatcaagc agctgagcgc tggctccaac acatctgcag ccctgactga ggacgggcgc  480
ctgttcatgt ggggagataa ttcagagggc cagattgggc tgaaaaacgt gagcaatgtg  540
tgcgtccctc agcaggtgac catcggaaag ccagtcagtt ggatttcatg tggctactat  600
catagcgcct tcgtgaccac agatggcgag ctgtacgtct ttggggagcc cgaaaacgga  660
aaactgggcc tgcctaacca gctgctgggc aatcaccgga caccccagct ggtgtccgag  720
atccctgaaa aagtgatcca ggtcgcctgc gggggagagc atacagtggt cctgactgag  780
aatgctgtgt ataccttcgg actgggccag tttggccagc tggggctggg aaccttcctg  840
tttgagacat ccgaaccaaa agtgatcgag aacattcgcg accagactat cagctacatt  900
tcctgcggag agaatcacac cgcactgatc acagacattg gcctgatgta tacctttggc  960
gatggacgac acgggaagct gggactggga ctggagaact tcactaatca ttttatcccc  1020
accctgtgtt ctaacttcct gcggttcatc gtgaaactgg tcgcttgcgg cgggtgtcac  1080
atggtggtct tcgctgcacc tcatagggc gtggctaagg agatcgaatt tgacgagatt  1140
aacgatacat gcctgagcgt ggcaactttc ctgccataca gctccctgac ttctggcaat  1200
gtgctgcaga gaaccctgag tgcaaggatg cggagaaggg agagggaacg ctctcctgac  1260
agtttctcaa tgcgacgaac cctgccacct atcgagggaa cactgggact gagtgcctgc  1320
ttcctgccta actcagtgtt tccacgatgt agcgagcgga atctgcagga gtctgtcctg  1380
agtgagcagg atctgatgca gccagaggaa cccgactacc tgctggatga gatgaccaag  1440
gaggccgaaa tcgacaactc tagtacagtg gagtccctgg gcgagactac cgatatcctg  1500
aatatgacac acattatgtc actgaacagc aatgagaaga gtctgaaact gtcaccagtg  1560
cagaagcaga agaaacagca gactattggc gagctgactc aggacaccgc cctgacagag  1620
aacgacgata gcgatgagta tgaggaaatg tccgagatga aggaaggcaa agcttgtaag  1680
cagcatgtca gtcaggggat cttcatgaca cagccagcca caactattga ggctttttca  1740
gacgaggaag tggagatccc cgaggaaaaa gagggcgcag aagattccaa ggggaatgga  1800
attgaggaac aggaggtgga agccaacgag gaaaatgtga aagtccacgg aggcaggaag  1860
gagaaaacag aaatcctgtc tgacgatctg actgacaagg ccgaggtgtc cgaaggcaag  1920
gcaaaatctg tcggagaggc agaagacgga ccagagggac gaggggatgg aacctgcgag  1980
gaaggctcaa gcggggctga gcattggcag gacgaggaac gagagaaggg cgaaaaggat  2040
aaaggccgcg gggagatgga acgacctgga gagggcgaaa aagagctggc agagaaggag  2100
gaatggaaga aaagggacgg cgaggaacag gagcagaaag aaagggagca gggccaccag  2160
aaggagcgca accaggagat ggaagagggc ggcgaggaag agcatggcga gggagaagag  2220
gaagagggcg atagagaaga ggaagaggaa aaagaaggcg aagggaagga ggaaggagag  2280
ggcgaggaag tggaaggcga gagggaaaag gaggaaggag aacggaagaa agaggaaaga  2340
gccggcaaag aggaaaaggg cgaggaagag ggcgatcagg gcgaaggcga ggaggaagag  2400
accgagggcc gcggggaaga gaaagaggag ggaggagagg tggagggcgg agaggtcgaa  2460
gagggaaagg gcgagcgcga agaggaagag gaagagggcg agggcgagga agaagagggc  2520
gagggggaag aagaggaggg agagggcgaa gaggaagagg gggagggaaa gggcgaagag  2580
gaaggagagg aaggggaggg agaggaagag ggggaggagg gcgaggggga aggcgaggag  2640
gaagaaggag agggggaagg cgaagaggaa ggcgaggggg aaggagagga ggaagaaggg  2700
gaaggcgaag gcgaagagga gggagaagga gagggggagg aagaggaagg agaagggaag  2760
ggcgaggagg aaggcgaaga gggagagggg gaaggcgagg aagaggaagg cgagggcgaa  2820
ggagaggacg gcgagggcga gggagaagag gaggaagggg aatgggaagg cgaagaagag  2880
gaaggcgaag gcgaaggcga agaagagggc gaaggggagg gcgaggaggg cgaaggcgaa  2940
ggggaggaag aggaaggcga aggagaaggc gaggaagaag agggagagga ggaaggcgag  3000
gaggaaggag agggggagga ggagggagaa ggcgagggcg aagaagaaga agagggagaa  3060
gtggagggcg aagtcgaggg ggaggaggga gaaggggaag gggaggaaga agagggcgaa  3120
gaagaaggcg aggaaagaga aaaagaggga gaaggcgagg aaaaccggag aaatagggaa  3180
gaggaggaag aggaagaggg aaagtaccag gagacaggcg aagaggaaaa cgagcggcag  3240
gatggcgagg aatataagaa agtgagcaag atcaaaggat ccgtcaagta cggcaagcac  3300
aaaacctatc agaagaaaag cgtgaccaac acacagggga atggaaaaga gcagaggagt  3360
aagatgcctg tgcagtcaaa acggctgctg aagaatggcc catctggaag taaaaaattc  3420
tggaacaatg tgctgcccca ctatctggaa ctgaaataa                        3459

SEQ ID NO: 4              moltype = DNA  length = 3459
FEATURE                   Location/Qualifiers
misc_feature              1..3459
                          note = Description of Artificial Sequence: Synthetic
                           polynucleotide
source                    1..3459
                          mol_type = other DNA
                          organism = synthetic construct
SEQUENCE: 4
atgagagagc cagaggagct gatgccagat agcggagcag tgtttacctt cggaaagtcc  60
aagttcgcag agaataaccc aggaaagttc tggtttaaaa acgacgtgcc cgtccacctg  120
tcttgtggcg atgagcatag tgccgtggtc actgggaaca ataagctgta tatgttcggg  180
tccaacaatt ggggacagct ggggctggga tccaaatctg ctatctctaa gccaacctgc  240
gtgaaggcac tgaaacccga gaaggtcaaa ctggccgctt gtggcagaaa ccacactctg  300
```

```
gtgagcaccg agggcgggaa tgtctatgcc accggaggca acaatgaggg acagctggga  360
ctgggggaca ctgaggaaag gaataccttt cacgtgatct ccttctttac atctgagcat  420
aagatcaagc agctgagcgc cggctccaac acatctgcag ccctgactga ggacgggcgc  480
ctgttcatgt ggggagataa ttcagagggc cagattgggc tgaaaaacgt gagcaacgtg  540
tgcgtgcctc agcaggtgac catcggaaag ccagtcagtt ggatttcatg tggctactat  600
catagcgcct tcgtgaccac agatggcgag ctgtacgtct ttggggagcc cgaaaacgga  660
aaactgggcc tgcctaacca gctgctgggc aatcaccgga caccccagct ggtgtccgag  720
atccctgaaa aagtgatcca ggtcgcctgc gggggagagc atacagtggt cctgactgag  780
aatgccgtgt acaccttcgg actgggccag tttggccagc tggggctggg aaccttcctg  840
tttgagacat ccgaaccaaa agtgatcgag aacattcgcg accagactat cagctacatt  900
tcctgcggag agaatcacac cgcactgatc acagacattg gcctgatgta tacctttggc  960
gatgggcggc acgggaagct gggactgggc ctggagaact tcactaatca cttcatcccc  1020
accctgtgct ctaacttcct gcggttcatc gtgaaactgg tcgcttgcgg cgggtgtcac  1080
atggtggtct tcgctgcacc tcatagggc gtggctaagg agatcgaatt tgacgagatt  1140
aacgatacat gcctgagcgt ggcaactttc ctgccataca gctccctgac ttctggcaat  1200
gtgctgcaga gaaccctgag tgcaaggatg cggagaaggg agagggaacg ctctcctgac  1260
agtttctcaa tgcgacgaac cctgccacct atcgagggga cactgggact gagtgcctgc  1320
ttcctgccta actcagtgtt tccacgatgt agcgagcgga atctgcagga gtctgtcctg  1380
agtgagcagg atctgatgca gccagaggaa cccgactacc tgctggatga gatgaccaag  1440
gaggccgaaa tcgacaactc tagtacagtg gagtccctgg gcgagactac cgatatcctg  1500
aatatgacac acattatgtc actgaacagc aatgagaaga gtctgaaact gtcaccagtg  1560
cagaagcaga agaaacagca gactattggc gagctgactc aggacaccgc cctgacagag  1620
aacgacgata gcgatgagta tgaggaaatg tccgagatga aggaaggcaa agcttgtaag  1680
cagcatgtga gtcaggggat cttcatgaca cagccagcca caactattga ggcttttca  1740
gacgaggaag tggagatccc cgaggaaaaa gagggcgcag aagattccaa ggggaatgga  1800
attgaggaac aggaggtgga agccaacgag gaaaatgtga aagtccacgg aggcaggaag  1860
gagaaaacag aaatcctgtc tgacgatctg actgacaagg ccgaggtgtc cgaaggcaag  1920
gcaaaatctg tcggagaggc agaagacgga ccagagggac gaggggatgg aacctgcgag  1980
gaaggctcaa gcggggctga gcattggcag gacgaggaac gagagaaggg cgaaaaggat  2040
aaaggccgcg gggagatgga acgacctgga gagggcgaaa aagagctggc agagaaggag  2100
gaatggaaga aaagggacgg cgaggaacag gagcagaaag aaagggagca gggccaccag  2160
aaggagcgca accaggagat ggaagagggc ggcgaggaag agcatggcga gggagaagag  2220
gaagagggcg atagagaaga ggaagaggaa aaagaaggcg aagggaagga ggaaggagag  2280
ggcgaggaag tggaaggcga gagggaaaag gaggaaggag aacggaagaa agaggaaaga  2340
gccggcaaag aggaaaaggg cgaggaagag ggcgatcagg gcgaaggcga ggaggaagag  2400
accgagggcc gcggggaaga gaaagaggag ggaggagagg tggagggcgg agaggtcgaa  2460
gagggaaagg gcgagcgcga agaggaagag gaagagggcg agggcgagga agaagagggc  2520
gagggggaag aagaggaggg agagggcgaa gaggaagagg gggagggaaa gggcgaagag  2580
gaaggagagg aaggggaggg agaggaagag ggggaggagg gcgaggggga aggcgaggag  2640
gaagaaggag agggggaagg cgaagaggaa ggcgaggggg aaggagagga ggaagaaggg  2700
gaaggcgaag gcgaagagga gggagaagga gagggggagg aagaggaagg agaagggaag  2760
ggcgaggagg aaggcgaaga gggagagggg gaaggcgagg aagaggaagg cgagggcgaa  2820
ggagaggacg gcgagggcga gggagaagag gaggaagggg aatgggaagg cgaagaagag  2880
gaaggcgaag gcgaaggcga agaagagggc gaaggggagg gcgaggaggg cgaaggcgaa  2940
ggggaggaag aggaaggcga aggagaaggc gaggaagaag agggagagga ggaaggcgag  3000
gaggaaggag agggggagga ggagggagaa ggcgagggcg aagaagaaga agagggagaa  3060
gtggagggcg aagtcgaggg ggaggaggga gaaggggaag gggaggaaga agagggcgaa  3120
gaagaaggcg aggaaagaga aaaagaggga gaaggcgagg aaaaccggag aaatagggaa  3180
gaggaggaag aggaagaggg aaagtaccag gagacaggcg aagaggaaaa cgagcggcag  3240
gatggcgagg aatataagaa agtgagcaag atcaaaggat ccgtcaagta cggcaagcac  3300
aaaacctatc agaagaaaag cgtgaccaac acacagggga atggaaaaga gcagcgaagt  3360
aaaatgcctg tgcagtcaaa acggctgctg aagaatggcc caagcgggtc taaaaaattc  3420
tggaacaatg tcctgccaca ctatctggaa ctgaagtga                         3459

SEQ ID NO: 5            moltype = DNA  length = 3459
FEATURE                 Location/Qualifiers
misc_feature            1..3459
                        note = Description of Artificial Sequence: Synthetic
                         polynucleotide
source                  1..3459
                        mol_type = other DNA
                        organism = synthetic construct
SEQUENCE: 5
atgagagagc ccgaggaact gatgcccgat agcggagccg tcttcacctt tgggaaatct  60
aaattcgcag agaacaaccc tggaaaattc tggtttaaga acgacgtgcc cgtgcacctg  120
agctgtggcg atgagcactc cgccgtggtg acaggcaaca ataagctgta catgttcggc  180
tctaacaatt ggggacagct gggcctggga agcaagtccg ccatcagcaa gccaacctgc  240
gtgaaggccc tgaagcccga gaaggtgaag ctggccgcct gtggcagaaa ccacacactg  300
gtgagcaccg agggcggcaa tgtgtatgcc acaggcggca acaatgaagg acagctgggc  360
ctgggcgaca cagaggagag gaataccttt cacgtgatca gcttctttac ctccgagcac  420
aagatcaagc agctgtccgc cggctctaac acatctgcag cactgacaga ggatggaaga  480
ctgttcatgt ggggcgataa tagcgagggc cagatcggcc tgaagaacgt gtccaatgtg  540
tgcgtgcctc agcaggtgac catcggcaag ccagtgtcct ggatctcttg tggctactat  600
cacagcgcct tcgtgaccac agatggcgag ctgtacgtgt ttggagagcc tgagaatggc  660
aagctgggcc tgcctaacca gctgctgggc aatcaccgga caccccagct ggtgtccgag  720
atccctgaga aagtgatcca ggtggcatgt ggcggcgagc acacagtggt gctgaccgag  780
aatgccgtgt ataccttttgg cctgggacag tttggccagc tgggcctggg cacattcctg  840
tttgagacat ccgagccaaa agtgatcgag aacatccgcg accagacaat cagctacatc  900
tcctgcggcg agaatcacac agccctgatc accgacatcg gcctgatgta tacctttggc  960
```

```
gatggaagac acggcaagct gggcctgggc ctggagaact tcacaaatca ctttatcccc  1020
accctgtgtt ctaacttcct gcggttcatc gtgaagctgg tggcctgcgg cggatgtcac  1080
atggtggtgt ttgcagcccc tcacaggggc gtggccaagg agatcgagtt tgacgagatc  1140
aacgatacat gcctgtccgt ggccaccttc ctgccataca gctccctgac atccggcaat  1200
gtgctgcaga gaaccctgtc tgcaagaatg agaagaaggg agagagagcg gtcccctgac  1260
tctttcagca tgagaagaac actgccccct attgagggaa ccctgggcct gtctgcctgc  1320
ttcctgccta actctgtgtt tccaagatgt agcgagagga atctgcagga gtctgtgctg  1380
agcgagcagg atctgatgca gccagaggag cccgactacc tgctggatga gatgacaaag  1440
gaggccgaga tcgacaactc tagcaccgtg gagagcctgg gcgagacaac agatatcctg  1500
aatatgacac acatcatgtc cctgaactct aatgagaagt ctctgaagct gagcccagtg  1560
cagaagcaga agaagcagca gaccatcggc gagctgaccc aggacacagc cctgaccgag  1620
aacgacgatt ctgatgagta tgaggagatg agcgagatga aggagggcaa ggcctgtaag  1680
cagcacgtgt cccagggcat cttcatgacc cagccagcca ccacaatcga ggccttttct  1740
gacgaggagg tggagatccc cgaggagaag gagggcgccg aggatagcaa gggcaatggc  1800
atcgaggagc aggaggtgga ggccaacgag gagaatgtga aggtgcacgg cggaagaaag  1860
gagaagacag agatcctgtc cgacgatctg accgacaagg ccgaggtgtc cgagggcaag  1920
gccaagtctg tgggagaggc agaggatgga cctgagggac gcggcgatgg aacatgtgag  1980
gagggctcct ctggagcaga gcactggcag gatgaggaga gagagaaggg cgagaaggat  2040
aagggcagag gcgagatgga gaggcctgga gagggagaga aggagctggc agagaaggag  2100
gagtggaaga agagggatgg cgaggagcag gagcagaagg agagagagca gggccaccag  2160
aaagagagga accaggagat ggaagagggc ggcgaggagg agcacggaga gggagaggag  2220
gaggagggcg atagagaaga agaggaggag aaagagggag agggcaagga ggagggagag  2280
ggagaagaag tggaaggaga gagagagaag gaggaaggag agcgcaagaa ggaagaaaga  2340
gcaggcaagg aggagaaagg agaggaggag ggcgatcagg gagaaggaga ggaggaggag  2400
acagaaggac gcggcgagga aaaagaggag ggcggcgagg tcgagggcgg cgaggtcgaa  2460
gagggcaagg gcgaaagaga agaagaggag gaggaaggcg agggcgaaga agaggagggc  2520
gagggcgagg aagaagaggg cgagggcgaa gaggaagaag gagagggcaa gggcgaggag  2580
gagggcgaag aaggcgaagg ggaggaggag ggcgaagagg gagagggcga gggcgaggag  2640
gaagaaggcg aaggagaagg cgaagaagaa ggagaaggag agggagaaga ggaggaaggc  2700
gaaggagagg gggaagagga aggagaaggg gagggcgaag aggaggaggg agaaggcaag  2760
ggagaggagg agggcgagga aggagaaggc gaaggcgagg aggaggaagg agagggagaa  2820
ggagaagatg gagaaggaga gggcgaggaa gaggaaggag agtgggaggg cgaggaagag  2880
gagggagaag gagaaggaga agaagaagga gaaggcgagg gagaagaagg agagggagaa  2940
ggggaagaag aggaggggga aggagagggc gaggaggaag agggagaaga agaaggcgaa  3000
gaagagggag aaggcgagga agaaggagag ggagaggggg aagaggagga agagggcgag  3060
gtggaaggag aggtggaggg cgaagagggg gaaggggaag gagaagaaga agaaggagag  3120
gaggagggag aggagagaga gaaagaaggc gagggcgagg agaacagaag gaatcgcgaa  3180
gaagaagaag aagaggaggg caagtaccag gagacaggcg aggaggagaa cgagcggcag  3240
gatggcgagg agtataagaa ggtgtccaag atcaagggct ctgtgaagta cggcaagcac  3300
aagacctatc agaagaagag cgtgaccaac acacagggca atggcaagga gcagcgcagc  3360
aagatgcctg tgcagtccaa gcggctgctg aagaatggcc caagcgggtc taaaaaattc  3420
tggaacaatg tcctgccaca ctatctggaa ctgaaataa                         3459

SEQ ID NO: 6            moltype = DNA  length = 3459
FEATURE                 Location/Qualifiers
misc_feature            1..3459
                        note = Description of Artificial Sequence: Synthetic
                         polynucleotide
source                  1..3459
                        mol_type = other DNA
                        organism = synthetic construct
SEQUENCE: 6
atgagagaac ccgaggaact gatgcctgac tctggcgccg tgttcacctt cggcaagagc  60
aagttcgccg agaacaaccc cggcaagttc tggttcaaga acgacgtgcc agtgcacctg  120
agctgtggcg acgaacattc tgccgtggtc accggcaaca acaagctgta catgttcggc  180
agcaacaact ggggccagct cggcctggga tctaagagcg ccatcagcaa gcctacctgc  240
gtgaaggccc tgaagcctga gaaagtgaag ctggccgcct gcggcagaaa tcacaccctg  300
gtttctaccg aaggcggcaa cgtgtacgcc accggcggaa acaatgaagg acagcttgga  360
ctgggcgaca ccgaggaaag aaacaccttc cacgtgatca gctttttcac cagcgagcac  420
aagatcaagc agctgagcgc cggcagcaat acctctgctg ccctgacaga agatggccgg  480
ctgttcatgt ggggcgacaa ttctgagggc cagatcggac tgaagaacgt gtccaatgtg  540
tgcgtgcccc agcaagtgac aatcggcaag cctgtgtcct ggatcagctg cggctactac  600
cacagcgcct tcgtgacaac agacggcgag ctgtatgtgt tcggcgagcc cgagaatggc  660
aagctgggac tgcctaatca gctgctgggc aaccacagaa cccctcagct ggtgtctgag  720
atccccgaaa aagtgatcca ggtggcctgt ggcggagagc acacagtggt gctgacagag  780
aatgccgtgt acacatttgg cctgggccag tttggccaac tcggactggg caccttcctg  840
ttcgagacaa gcgagcccaa agtgatcgag aacatccggg accagaccat cagctacatc  900
tcttgcggcg agaaccacac agccctgatc acagacatcg gcctgatgta taccttcggc  960
gacggcagac acggcaaact cggccttggc ctggaaaact tcaccaacca cttcatccct  1020
actctgtgca gcaacttcct gcggttcatc gtgaaactgg tggcctgcgg aggctgccac  1080
atggtggttt ttgccgctcc tcatagaggc gtggccaaag agattgagtt cgacgagatc  1140
aacgatacct gcctgagcgt ggccaccttt ctgccttaca gctctctgac cagcggcaat  1200
gtgctgcaga ggacactgag cgccagaatg cgcagacggg aaagagagag aagccccgac  1260
agcttcagca tgcggagaac cctgcctcca atcgagggaa cactgggcct gagcgcctgc  1320
ttcctgccta atagcgtgtt ccccagatgc agcgagcgga acctgcaaga gtctgtgctg  1380
agcgagcagg acctgatgca gcctgaggaa cccgactacc tgctggacga gatgaccaaa  1440
gaggccgaga tcgacaacag cagcaccgtg gaatctctgg gcgagacaac cgacatcctg  1500
aacatgaccc acatcatgag cctgaacagc aacgagaagt ctctgaagct gagccccgtg  1560
cagaagcaga agaagcagca gaccatcgga gagctgaccc aggataccgc tctgaccgag  1620
```

```
aacgacgaca gcgacgagta cgaagagatg agcgagatga aggaaggcaa ggcctgcaag  1680
cagcacgtgt cccagggcat ctttatgacc cagcctgcca ccaccatcga ggccttttcc  1740
gacgaggaag tggaaatccc cgaggaaaaa gagggcgccg aggacagcaa aggcaacggc  1800
attgaggaac aagaggtgga agccaacgaa gagaacgtga aggtgcacgg cggacggaaa  1860
gagaaaacag agatcctgag cgacgacctg accgacaagg ccgaagtgtc tgagggcaaa  1920
gccaagtctg tgggcgaagc cgaggacggc ccagaaggca gaggcgacgg aacatgtgaa  1980
gagggatcta gcggagccga gcactggcag gacgaagaga gagagaaagg cgagaaggac  2040
aaaggcaggg gcgagatgga aagacctggc gagggcgaaa aagagctggc cgagaaagag  2100
gagtggaaga aacgcgacgg cgaagaacaa gagcagaaag aacgcgagca gggccaccag  2160
aaagaaagaa atcaagagat ggaagaaggc ggcgaggaag aacacggcga aggggaagaa  2220
gaggaaggcg accgagagga agaagaagaa aaagaaggcg aaggcaaaga ggaaggcgag  2280
ggcgaagagg tggaaggcga gcgggaaaaa gaagagggcg agcgcaagaa agaagaaaga  2340
gccggcaaag aagagaaggg cgaagaagaa ggcgatcaag gcgaaggcga ggaagaagaa  2400
accgaaggcc gcggagaaga gaaagaggaa ggcggcgaag ttgaaggcgg cgaggtggaa  2460
gaaggcaagg gcgagagaga agaagaggaa gaggaaggcg aaggggaaga agaagaaggc  2520
gagggcgaag aggaagaagg cgaaggcgag gaagaggaag gcgaaggcaa gggcgaagag  2580
gaaggcgaag aaggcgaggg cgaagaagag ggagaagaag gcgaaggcga gggcgaagaa  2640
gaggaaggcg aaggcgaagg cgaggaagaa ggcgaaggcg aaggcgaaga ggaagaaggc  2700
gaaggcgaag gggaagaaga aggcgaaggc gaaggcgagg aagaggaagg cgaaggcaaa  2760
ggggaagaag agggcgaaga aggcgaaggc gaaggcgagg aagaagaagg cgaaggcgaa  2820
ggcgaagacg gcgaaggcga gggcgaagag gaagagggcg agtgggaggg cgaagaagaa  2880
gaaggcgaag gcgagggcga agaggaaggc gaaggcgaag gcgaagaagg cgagggcgaa  2940
ggcgaagaag aagaaggcga aggcgaaggc gaagaagagg aaggggaaga agaaggcgaa  3000
gaggaaggcg agggcgaaga agaaggcgaa ggcgagggcg aagaagagga agagggcgaa  3060
gttgaagggg aagttgaggg cgaagaaggc gaaggcgaag gggaagaaga ggaaggcgag  3120
gaagagggcg aagaacgcga gaaagaaggc gaaggggaag agaaccgccg gaacagagaa  3180
gaggaagaag aagaggaagg caagtaccaa gagacaggcg aggaagagaa cgagcggcag  3240
gatggcgaag agtacaagaa ggtgtccaag atcaagggca gcgtgaagta cggcaagcac  3300
aagacctacc agaaaaagtc cgtgaccaac acacaaggca atggcaaaga acagcggagc  3360
aagatgcccg tgcagtccaa gagactgctg aagaatggcc ccagcggcag caaaaagttc  3420
tggaacaacg tgctgcccca ctacctggaa ctgaagtga                        3459
```

```
SEQ ID NO: 7           moltype = DNA  length = 295
FEATURE                Location/Qualifiers
misc_feature           1..295
                       note = Description of Unknown: GRK1 long (GRK1L) sequence
source                 1..295
                       mol_type = other DNA
                       organism = unidentified
SEQUENCE: 7
gggccccaga agcctggtgg ttgtttgtcc ttctcagggg aaaagtgagg cggccccttg  60
gaggaagggg ccgggcagaa tgatctaatc ggattccaag cagctcaggg gattgtcttt  120
ttctagcacc ttcttgccac tcctaagcgt cctccgtgac cccggctggg atttagcctg  180
gtgctgtgtc agccccgggc tcccaggggc ttcccagtgg tccccaggga accctcgaca  240
gggccagggc gtctctctcg tccagcaagg gcagggacgg gccacaggca agggc       295

SEQ ID NO: 8           moltype = DNA  length = 199
FEATURE                Location/Qualifiers
misc_feature           1..199
                       note = Description of Unknown: GRK1S short (GRK1S) sequence
source                 1..199
                       mol_type = other DNA
                       organism = unidentified
SEQUENCE: 8
gggccccaga agcctggtgg ttgtttgtcc ttctcagggg aaaagtgagg cggccccttg  60
gaggaagggg ccgggcagaa tgatctaatc ggattccaag cagctcaggg gattgtcttt  120
ttctagcacc ttcttgccac tcctaagcgt cctccgtgac cccggctggg atttagcctg  180
gtgctgtgtc agccccggg                                               199

SEQ ID NO: 9           moltype = DNA  length = 225
FEATURE                Location/Qualifiers
misc_feature           1..225
                       note = Description of Unknown: bGHpA sequence
source                 1..225
                       mol_type = other DNA
                       organism = unidentified
SEQUENCE: 9
ctgtgccttc tagttgccag ccatctgttg tttgcccctc ccccgtgcct tccttgaccc  60
tggaaggtgc cactcccact gtcctttcct aataaaatga ggaaattgca tcgcattgtc  120
tgagtaggtg tcattctatt ctggggggtg gggtggggca ggacagcaag ggggaggatt  180
gggaagacaa tagcaggcat gctggggatg cggtgggctc tatgg                  225

SEQ ID NO: 10          moltype = DNA  length = 135
FEATURE                Location/Qualifiers
misc_feature           1..135
                       note = Description of Unknown: SV40pA sequence
source                 1..135
                       mol_type = other DNA
                       organism = unidentified
```

-continued

```
SEQUENCE: 10
gatccagaca tgataagata cattgatgag tttggacaaa ccacaactag aatgcagtga  60
aaaaaatgct ttatttgtga aatttgtgat gctattgctt tatttgtaac cattataagc  120
tgcaataaac aagtt                                                   135

SEQ ID NO: 11          moltype = DNA  length = 56
FEATURE                Location/Qualifiers
misc_feature           1..56
                       note = Description of Unknown: rbGlobpA sequence
source                 1..56
                       mol_type = other DNA
                       organism = unidentified
SEQUENCE: 11
aataaaggaa atttattttc attgcaatag tgtgttggaa ttttttgtgt ctctca      56

SEQ ID NO: 12          moltype = DNA  length = 477
FEATURE                Location/Qualifiers
misc_feature           1..477
                       note = Description of Unknown: hGHpA sequence
source                 1..477
                       mol_type = other DNA
                       organism = unidentified
SEQUENCE: 12
gggtggcatc cctgtgaccc ctccccagtg cctctcctgg ccctggaagt tgccactcca  60
gtgcccacca gccttgtcct aataaaatta agttgcatca ttttgtctga ctaggtgtcc  120
ttctataata ttatggggtg gaggggggtg gtatggagca aggggcaagt tgggaagaca  180
acctgtaggg cctgcggggt ctattgggaa ccaagctgga gtgcagtggc acaatcttgg  240
ctcactgcaa tctccgcctc ctgggttcaa gcgattctcc tgcctcagcc tcccgagttg  300
ttgggattcc aggcatgcat gaccaggctc agctaatttt tgtttttttg gtagagacgg  360
ggtttcacca tattggccag gctggtctcc aactcctaat ctcaggtgat ctacccacct  420
tggcctccca aattgctggg attacaggcg tgaaccactg ctcccttccc tgtcctt     477

SEQ ID NO: 13          moltype = DNA  length = 97
FEATURE                Location/Qualifiers
misc_feature           1..97
                       note = Description of Unknown: SV40 intron sequence
source                 1..97
                       mol_type = other DNA
                       organism = unidentified
SEQUENCE: 13
gtaagtttag tctttttgtc ttttatttca ggtcccggat ccggtggtgg tgcaaatcaa  60
agaactgctc ctcagtggat gttgccttta cttctag                           97
```